· US009676712B2

United States Patent
Barrett et al.

(10) Patent No.: US 9,676,712 B2
(45) Date of Patent: Jun. 13, 2017

(54) LACTAM COMPOUNDS AS EP$_4$ RECEPTOR-SELECTIVE AGONISTS FOR USE IN THE TREATMENT OF EP$_4$-MEDIATED DISEASES AND CONDITIONS

(71) Applicants: Cayman Chemical Company, Inc., Ann Arbor, MI (US); Myometrics, LLC, New London, CT (US)

(72) Inventors: Stephen Douglas Barrett, Hartland, MI (US); Bradlee David Germain, Ann Arbor, MI (US); Adam Uzieblo, Farmington Hills, MI (US); Fred Lawrence Ciske, Dexter, MI (US); Gregory William Endres, Saline, MI (US); Andriy Kornilov, Ypsilanti, MI (US); Kirk M. Maxey, Ann Arbor, MI (US); James Paul O'Malley, Dunedin (NZ); Thomas Allen Owen, Pompton Plains, NJ (US)

(73) Assignee: CAYMAN CHEMICAL COMPANY, INC., Ann Arbor, MI (US)

( * ) Notice: Subject to any disclaimer, the term of this patent is extended or adjusted under 35 U.S.C. 154(b) by 0 days.

(21) Appl. No.: 14/775,512

(22) PCT Filed: Mar. 14, 2014

(86) PCT No.: PCT/US2014/029093
§ 371 (c)(1),
(2) Date: Sep. 11, 2015

(87) PCT Pub. No.: WO2014/144610
PCT Pub. Date: Sep. 18, 2014

(65) Prior Publication Data
US 2016/0031811 A1    Feb. 4, 2016

Related U.S. Application Data

(60) Provisional application No. 61/799,251, filed on Mar. 15, 2013.

(51) Int. Cl.
| | | |
|---|---|---|
| *C07D 207/27* | (2006.01) | |
| *C07D 417/06* | (2006.01) | |
| *C07D 207/12* | (2006.01) | |
| *C07D 409/06* | (2006.01) | |

(52) U.S. Cl.
CPC ......... *C07D 207/27* (2013.01); *C07D 207/12* (2013.01); *C07D 409/06* (2013.01); *C07D 417/06* (2013.01)

(58) Field of Classification Search
CPC .................................................. C07D 207/27
See application file for complete search history.

(56) References Cited

U.S. PATENT DOCUMENTS

| | | | |
|---|---|---|---|
| 3,975,399 | A | 8/1976 | DeFranco et al. |
| 4,177,346 | A | 12/1979 | Nelson |
| 4,268,522 | A | 5/1981 | Eggler et al. |
| 4,456,613 | A | 6/1984 | Wang |
| 6,043,275 | A | 3/2000 | Maruyama et al. |
| 6,462,081 | B1 | 10/2002 | Maruyama et al. |
| 6,573,294 | B1 | 6/2003 | Old et al. |
| 6,642,266 | B2 | 11/2003 | Cameron et al. |
| 6,737,437 | B2 | 5/2004 | Cameron et al. |
| 6,849,657 | B2 | 2/2005 | Elworthy et al. |
| 6,891,062 | B2 | 5/2005 | Oida et al. |
| 6,894,175 | B1 | 5/2005 | DeLong |
| 7,169,807 | B2 | 1/2007 | Donde |
| 7,256,211 | B1 | 8/2007 | Kambe et al. |

(Continued)

FOREIGN PATENT DOCUMENTS

| | | |
|---|---|---|
| CA | 1085859 | 9/1980 |
| EP | 0046082 B1 | 6/1985 |

(Continued)

OTHER PUBLICATIONS

Partial Translation of International Publication No. WO 2002/024647 A1 (A44 above).

(Continued)

*Primary Examiner* — Rebecca Anderson
*Assistant Examiner* — Karen Cheng
(74) *Attorney, Agent, or Firm* — Brinks Gilson & Lione

(57) ABSTRACT

Disclosed herein are compounds of formula (I)

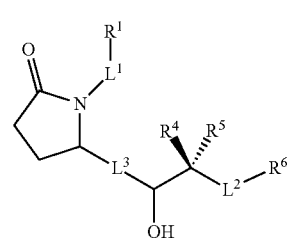

wherein $L^1$, $L^2$, $L^3$, $R^1$, $R^4$, $R^5$, and $R^6$ are as defined in the specification. Compounds of formula (I) are EP$_4$ agonists useful in the treatment of glaucoma, osteoporosis, bone fracture, periodontal bone loss, orthopedic implant, alopecia, neuropathic pain, and related disorders. Pharmaceutical compositions and methods of treating conditions or disorders are also described.

24 Claims, No Drawings

(56) References Cited

U.S. PATENT DOCUMENTS

| | | |
|---|---|---|
| 7,276,531 B2 | 10/2007 | Araldi et al. |
| 7,402,605 B2 | 7/2008 | Tani et al. |
| 7,410,991 B2 | 8/2008 | Araldi et al. |
| 7,419,999 B2 | 9/2008 | Araldi et al. |
| 7,652,063 B2 | 1/2010 | Donde |
| 7,683,094 B2 | 3/2010 | Tani et al. |
| 9,180,116 B2 | 11/2015 | Barrett et al. |
| 2001/0047105 A1 | 11/2001 | Cameron et al. |
| 2002/0040149 A1 | 4/2002 | Cameron et al. |
| 2003/0176479 A1 | 9/2003 | Cameron et al. |
| 2005/0020686 A1 | 1/2005 | Maruyama et al. |
| 2005/0124577 A1 | 6/2005 | Tani et al. |
| 2006/0167081 A1 | 7/2006 | Billot et al. |
| 2007/0191319 A1 | 8/2007 | Ke et al. |
| 2008/0021021 A1 | 1/2008 | Okada et al. |
| 2008/0234337 A1 | 9/2008 | Kuwahara et al. |
| 2010/0216689 A1 | 8/2010 | Takigawa et al. |
| 2010/0280250 A1 | 11/2010 | Im et al. |
| 2012/0283293 A1 | 11/2012 | Andreasson |
| 2014/0179606 A1 | 6/2014 | Kanaji et al. |
| 2015/0174099 A1 | 6/2015 | Barrett et al. |
| 2015/0175538 A1 | 6/2015 | Barrett et al. |

FOREIGN PATENT DOCUMENTS

| | | |
|---|---|---|
| EP | 1121939 A2 | 8/2001 |
| EP | 0878465 B1 | 7/2003 |
| GB | 1553595 A1 | 10/1979 |
| GB | 1583163 A1 | 1/1981 |
| WO | WO 01/46140 A1 | 6/2001 |
| WO | WO 02/24647 A1 | 3/2002 |
| WO | WO 02/42268 A2 | 5/2002 |
| WO | WO 03/007941 A1 | 1/2003 |
| WO | WO 03/008377 A1 | 1/2003 |
| WO | WO 03/047417 A2 | 6/2003 |
| WO | WO 03/047513 A2 | 6/2003 |
| WO | WO 03/077910 A1 | 9/2003 |
| WO | WO 03/103604 A2 | 12/2003 |
| WO | WO 2004/037786 A2 | 5/2004 |
| WO | WO 2009/055289 A2 | 4/2009 |
| WO | WO 2011/003058 A1 | 1/2011 |
| WO | WO 2012/063207 A1 | 5/2012 |
| WO | WO 2013/018837 A1 | 2/2013 |
| WO | WO 2014/015246 A1 | 1/2014 |
| WO | WO 2014/015247 A1 | 1/2014 |

OTHER PUBLICATIONS

Billot, X. et al. "Discovery of a Potent and Selective Agonist of the Prostaglandin $EP_4$ Receptor," Biorganic & Medicinal Chemistry Letters, 2003, 13, 1129-1132.

Brochure: "Comprehensive Bone Regeneration Solutions," BioHorizons Science Innovation Service, 2009, www.biohorizons.com, 12 pgs.

Brochure: "JRF STIMUBLAST™ Demineralized Bone Matrix," Arthrex Inc., 2011, http://biologics.arthrex.com, 6 pgs.

Cameron, K.O. et al. "Discovery of Highly Selective EP4 Receptor Agonists That Stimulate New Bone Formation and Restore Bone Mass in Ovariectomized Rats," Biorganic & Medicinal Chemistry Letters, 2006, 16, 1799-1802.

Dorozhkin, S.V. et al. "Calcium Orthophsphate Cements and Concretes," Materials, 2009, 2, 221-291.

Elworthy, T.R. et al. "Lactams as $EP_4$ Prostanoid Receptor Agonists. 3. Discovery of N-Ethylbenzoic Acid 2-Pyrrolidinones as Subtype Selective Agents," J. Med. Chem., 2004, 20, 6124-6127.

Elworthy, T.R. et al. "Lactams as $EP_4$ Prostanoid Receptor Subtype Selective Agonists. Part 1: 2-Pyrrolidinones-Stereochemical and Lower Side-Chain Optimization," Biorganic & Medicinal Chemistry Letters, 2004, 14, 1655-1659.

Elworthy, T.R. et al. "Lactams as Prostanoid Receptor Ligands. Part 4: 2-Piperidones as Selective $EP_4$ Receptor Agonists," Biorganic & Medicinal Chemistry Letters, 2005, 15, 2523-2526.

Espanol, M. et al. "Intrinsic Porosity of Calcium Phosphate Cements and Its Significance for Drug Delivery and Tissue Engineering Applications," Acta Biomaterialia, 2009, 5, 2752-2762.

Ginebra, M.P. et al. "Calcium Phosphate Cements as Bone Drug Delivery Systems: A Review," J. Controlled Release, 2006, 113, 102-110.

Ginebra, M-P. et al. "Calcium Phosphate Cements: Competitive Drug Carriers for the Musculoskeletal System?" Biomaterials, 2006, 27, 2171-2177.

Hayashi, K. et al. "Effect of a Prostaglandin EP4 Receptor Agonist on Early Fixation of Hydroxyapatite/Titanium Composite- and Titanium-Coated Rough-Surfaced Implants in Ovariectomized Rats," J. Biomedical Materials Research Part A, 2009, 1202-1209.

Hayashi, K. et al. "Prostaglandin EP4 Receptor Agonist Augments Fixation of Hydroxyapatite-Coated Implants in a Rat Model of Osteoporosis," J. Bone and Joint Surgery, 2005, 87-8, 1150-1156.

Hu, K-Z et al., "$SmI_2$-Mediated Intermolecular Coupling of γ-Lactam N-α-Radicals with Activated Alkenes: Asymmetric Synthesis of 11-Hydroxylated Analogues of the Lead Compounds CP-734432 and PF-04475270," J. Org. Chem., 2013, 78, 1790-1801.

Iwaniec, U.T. et al. "A Comparative Study of the Bone-Restorative Efficacy of Anabolic Agents in Aged Ovariectomized Rats," Osteoporos. Int., 2007, 18, 351-362.

Kambe, T. et al. "Synthesis and Evaluation of γ-lactam Analogs of $PGE_2$ as EP4 and EP2/EP4 Agonists," Bioorganic & Medicinal Chemistry, 2012, 20, 3502-3522.

Li, M. et al. "Prostaglandin $E_2$ Receptors in Bone Formation," International Orthopaedics, 2007, 31, 767-772.

Maruyama, T. et al. "Design and Synthesis of a Highly Selective EP4-Receptor Agonist. Part 1: 3,7-DithiaPG Derivatives With High Selectivity," Bioorganic & Medicinal Chemistry Letters, 2001, 11, 2029-2031.

Maruyama, T. et al. "Design and Synthesis of a Highly Selective EP4-Receptor Agonist. Part 2: 5-Thia and 9β-HaloPG Derivatives With Improved Stability," Bioorganic & Medicinal Chemistry Letters, 2001, 11, 2033-2035.

Maruyama, T. et al. "Design and Synthesis of a Selective EP4-Receptor Agonist. Part 1: Discovery of 3,7-$DithiaPGE_1$ Derivatives and Identification of Their ω Chains," Bioorganic & Medicinal Chemistry, 2002, 10, 975-988.

Maruyama, T. et al. "Design and Synthesis of a Selective EP4-Receptor Agonist. Part 2: 3,7-$DithiaPGE_1$ Derivatives With High Selectivity," Bioorganic & Medicinal Chemistry, 2002, 10, 989-1008.

Maruyama, T. et al. "Design and Synthesis of a Selective EP4-Receptor Agonist. Part 3: 16-Phenyl-$5thiaPGE_1$ and 9-β-Halo Derivatives With Improved Stability," Bioorganic & Medicinal Chemistry, 2002, 10, 1743-1759.

Maruyama, T. et al. "Design and Synthesis of a Selective EP4-Receptor Agonist. Part 4: Practical Synthesis and Biological Evaluation of a Novel Highly Selective EP4-Receptor Agonist," Bioorganic & Medicinal Chemistry, 2002, 10, 2103-2110.

Nair S.K. et al. "Novel Synthesis of CP-734432, an EP4 Agonist, Using Sharpless Asymmetric Dihydroxylation," Tetrahedron Letters, 2010, 51, 1451-1454.

Nakagawa, K. et al. "Prostaglandin $E_2$ EP4 Agonist (ONO-4819) Accelerates BMP-induced Osteoblastic Differentiation," Bone, 2007, 41, 543-548.

Orlovskii, V.P. et al. "Hydroxyapatite and Hydroxyapatite-Based Ceramics," Inorganic Materials, 2002, 38, 973-984.

International Search Report and Written Opinion for corresponding International Patent Application No. PCT/US2013/051263, dated Oct. 2, 2013 (10 pages).

International Search Report and Written Opinion for corresponding International Patent Application No. PCT/US2014/029093, dated Jun. 30, 2014 (9 pages).

Prasanna, G. et al. "Ocular Pharmacokinetics and Hypotensive Activity of PF-04475270, an EP4 Prostaglandin Agonist in Preclinical Models," Experimental Eye Research, 2009, 89, 608-617.

Saeki, T. et al. "Effects of Prostanoid EP Agonists on Mouse Intraocular Pressure," IOVS, 2009, 50, 2201-2208.

(56) References Cited

OTHER PUBLICATIONS

Smith, R.L. et al. "Prostaglandin Isosteres. 1. (8-Aza-, 8,10-Diaza-, and 8-Aza-11-thia)-9-oxoprostanoic Acids and Their Derivatives," *J. Med. Chem.*, 1977, 20, 1292-1299.
Toyoda, H. et al. "Augmentation of Bone Morphogenetic Protein-Induced Bone Mass by Local Delivery of a Prostaglandin E EP4 Receptor Agonist," *Bone*, 2005, 555-562.
Wang, C-L.J. et al. "Azaprostanoids I. Synthesis of (RAC)-8-Aza-11-Deoxy-15-Deoxy-16-Hydroxy-16-Methylprostaglandins," *Tetrahedron Letters*, 1982, 10, 1067-1070.
Xiao, Y. et al. "Discovery of Novel Prostaglandin Analogs of $PGE_2$ as Potent and Selective $EP_2$ and $EP_4$ Receptor Agonists," *Biorganic & Medicinal Chemistry Letters*, 2007, 17, 4323-4327.
Xiao, Y. et al. "Synthesis and Evaluation of a γ-lactam as a Highly Selective $EP_2$ and $EP_4$ Receptor Agonist," *Biorganic & Medicinal Chemistry Letters*, 2008, 18, 821-824.
Yokoyama, U. et al. "Chronic Activation of the Prostaglandin Receptor EP4 Promotes Hyaluronan-Medicated Neointimal Formation in the Ductus Arteriosus," *J. Clin. Inves.*, 2006, 116, 3026-3034.
Yoshida, K. et al., "Stimulation of bone formation and prevention of bone loss by prostaglandin E EP4 receptor activation," *PNAS*, 2014, 99(7) 4580-4585.

LACTAM COMPOUNDS AS EP₄ RECEPTOR-SELECTIVE AGONISTS FOR USE IN THE TREATMENT OF EP₄-MEDIATED DISEASES AND CONDITIONS

RELATED APPLICATIONS

This application is the U.S. National Phase under 35 U.S.C. §371 of International Patent Application No. PCT/US2014/029093, filed Mar. 14, 2014, which claims priority to and the benefit of U.S. Provisional Application Ser. No. 61/799,251, filed Mar. 15, 2013.

FIELD OF THE INVENTION

The subject matter disclosed and claimed herein centers on novel EP$_4$ receptor-selective pyrrolidin-2-one (γ-lactam) derivatives and their uses as therapies for EP$_4$ receptor-mediated diseases and conditions.

BACKGROUND OF THE INVENTION

All references, including patents and patent applications, are hereby incorporated by reference in their entireties.

Arachidonic acid (abbreviated as AA herein) is a ubiquitous polyunsaturated fatty acid (PUFA) that is found esterified to phospholipids at the secondary alcohol of glycerol in all mammalian cellular membranes. Enzymatic hydrolysis of esterified AA by calcium ($Ca^{2+}$)-induced cytosolic phospholipase 2 (cPLA2) releases free AA, which may be further catalytically converted by the cyclooxygenase (COX) into the intermediate prostaglandin H2 followed by subsequent enzymatic isomerization into the naturally occurring prostaglandins (PGs) and thromboxanes. The five primary prostanoids include prostaglandin F$_{2\alpha}$ (PGF$_{2\alpha}$, prostaglandin D$_2$ (PGD$_2$), prostaglandin I$_2$ (PGI$_2$), thromboxane A$_2$(TxA$_2$), and prostaglandin E$_2$ (PGE$_2$), (Jahn, U. et al., *Angew. Chem. Int. Ed.* 2008, 47, 5894-5955; Wymann, M. P. et al., *Nat. Rev. Mot. Cell. Biol.* 2008, 9, 162-176; Samuelsson, B. et al., *Ann. Rev. Biochem.* 1978, 47, 997-1029). These five prostaglandins are lipid mediators that interact with nine specific members of a distinct prostanoid subfamily of G-protein-coupled receptors (GPCRs), designated FP, DP$_{1-2}$, IP, TP, and EP$_{1-4}$, respectively (Breyer, R. M. et al., *Annu. Rev. Pharmacol. Toxicol.* 2001, 41, 661-690). Prostaglandin and PG receptor pharmacology, signaling, and physiology have been studied and well documented (Hata, A. N. et al., *Pharmacol. Ther.* 2004, 103(2), 147-166; ElAttar, T. M. A., *J. Oral Pathol. Med.* 1978, 7(5), 239-252; Poyser, N. L., *Clinics in Endocrinology and Metabolism* 1973, 2(3), 393-410). Prostaglandins are short-lived local signaling molecules that are not stored in cells or tissues but are produced as needed by specific cells of virtually all body tissues. Their target cells reside in the immediate vicinity of their secretion sites. Well-known PG functions include regulation of cell stimulation, growth, and differentiation, immune response and inflammation, allergy, asthma, pain, vasomotor action, neuromodulation, intraocular pressure, and platelet aggregation, as well as mediation of fever, managing of renal blood flow, and induction of labor (Negishi, M. et al., *Prog. Lipid Res.* 1993, 32(4), 417-434).

As is the case for most prostaglandins, the biosynthesis of PGE$_2$ commences with liberation of free AA from its esterified form in the cell membrane. One key enzyme involved in PGE$_2$ biosynthesis is prostaglandin H synthase (PGHS). PGHS possesses both a COX and a peroxidase function. The COX activity promotes conversion of free AA to the unstable endoperoxide prostaglandin G$_2$ (PGG$_2$) via double oxygen insertion. One inserted oxygen molecule is subsequently reduced by the peroxidase activity of PGHS to provide the versatile biosynthetic cascade intermediate PGH$_2$. The glutathione-dependent enzyme prostaglandin E synthase (PGES) promotes isomerization of PGH$_2$ to PGE$_2$ via peroxide ring opening of PGH$_2$ to provide the highly functionalized hydroxypentanone scaffold of PGE$_2$.

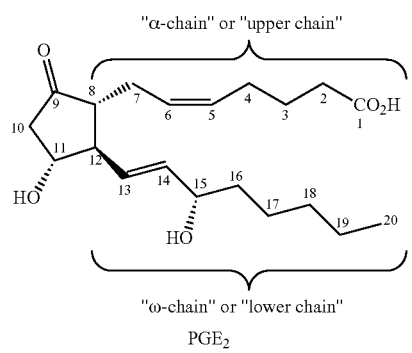

PGE$_2$

The physiology of PGE$_2$ and the pharmacology of its four known complementary receptor subtypes designated EP$_1$, EP$_2$, EP$_3$, and EP$_4$ are among the most widely studied and published fields of PG research (Sugimoto, Y. et al., *J. Biol. Chem.* 2007, 282(16), 11613-11617; Suzuki, J. et al., *Prostaglandins* 2010, 127-133; Regan, J. et al., *Life Sciences* 2003, 74(2-3), 143-153; Bouayad, A. et al., *Current Ther. Res.* 2002, 63(10), 669-681; Breyer, M. et al., *Kidney Int., Suppl.* 1998, 67, S88-S94; Breyer, M. et al., *Amer. J. Physiol.* 2000, 279(1, Part 2), F12-F23; Negishi, M. et al., *Recent Res. Dev. Endocrinol.* 2000, 1(1), 133-143; Ma, W. et al., *Prog. Inflamm. Res.* 2006, 39-93; Mutoh, M. et al., *Current Pharmaceutical Design* 2006, 12(19), 2375-2382; Hebert, R. et al., *Current Topics in Pharmacology* 2002, 6, 129-137; Coleman, R. et al., *Pharm. Rev.* 1994, 46(2), 205-229). PGE$_2$ binds to each of the four EP receptors with high affinity (Anderson, L. et al., *Journal of Reproduction and Fertility,* 1999, 116, 133-141). The prostaglandin PGE$_1$ (saturated α-chain analog of PGE$_2$), the major eicosanoid synthesized biologically from dihomo-γ-linolenic acid (DGLA) in response to various stimuli, also binds efficiently to all four EP receptor subtypes.

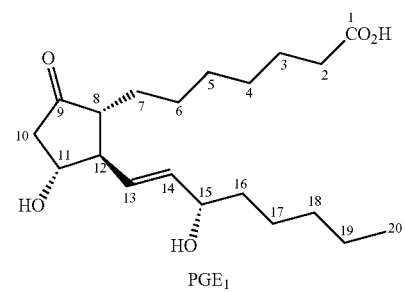 [SMILES: CCCCC[C@H](O)/C=C/[C@H]1[C@H](O)CC(=O)[C@@H]1CCCCCCC(=O)O]

PGE$_1$

The EP$_4$ receptor is expressed in a wide variety of tissues including those of the skeletal, muscular, central and peripheral nervous, immune, respiratory, cardiovascular, digestive, excretory, and reproductive tissues and is known to be involved in such processes and conditions as bone growth and remodeling, osteoporosis, relaxation of smooth muscle, neuroprotection, ocular inflammation, immune response, and cancer. Modulation of the $EP_4$ receptor may also be involved in the neonatal development of the circulatory system (Fan, F. et al., *Clinical and Experimental Pharmacology and Physiology*, 2010, 37, 574-580; Bouayad, A. et al., *Current Ther. Res.* 2002, 63(10), 669-681; Bouayad, A. et al., *Am. J. Physiol. Heart Circ. Physiol.* 2001, 280, H2342-H2349). Activation of the $EP_4$ receptor by $PGE_2$ increases intracellular cAMP levels, leading to downstream effects associated with antiapoptotic activity and cytoprotection (Fujino, H. and Regan, J., *Trends in Pharmacological Sciences*, 2003, 24(7), 335-340; Hoshino, T. et al., *J. Biol. Chem.*, 2003, 278(15), 12752-12758; Takahashi, S. et al., *Biochem. Pharmacol.*, 1999, 58(12), 1997-2002; Quiroga, J. et al., *Pharmacol. Ther.*, 1993, 58(1), 67-91).

$EP_4$ receptor agonists are reported to be useful in lowering intraocular pressure and to have application in treating glaucoma. Prasanna, G. et al., *Exp. Eye Res.*, 2009, 89 (5), 608-17; Luu, K. et al., *J. Pharmacol. Exp. Ther.* 2009, 331(2), 627-635; Saeki, T. et al, *Invest. Ophthalmol. Vis. Sci.*, 2009, 50 (5) 2201-2208.

$EP_4$ receptor agonists are also reported to induce bone remodeling and to have use in the treatment of osteoporosis. Iwaniec, U. et al., *Osteoporosis International*, 2007, 18 (3), 351-362; Aguirre, J. et al., *J. Bone and Min. Res.*, 2007, 22(6), 877-888; Yoshida, K. et al., *Proc. Natl. Acad. Sci. USA*, 2002, 99 (7), 4580-4585. Hayashi, K. et al., *J. Bone Joint Surg. Br.*, 2005, 87-B (8), 1150-6.

SUMMARY OF THE INVENTION

In one aspect, the present invention provides compounds of formula (I)

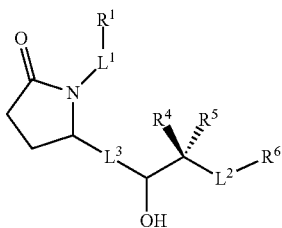

(I)

or a pharmaceutically acceptable salt thereof, wherein:
$L^1$ is
a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene is optionally substituted with 1, 2, 3, or 4 fluoro substituents;
b) —$(CH_2)_t$-G-$(CH_2)_p$—; wherein t is 0, 1, or 2, p is 0, 1, 2, or 3, and t+p=0, 1, 2, 3, or 4; or
c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{12}$)=C($R^{12}$)-$G^2$-, wherein n is 1, 2, 3, 4, or 5, p is 0, 1, 2, or 3, and n+p=1, 2, 3, 4, 5, or 6;
G is

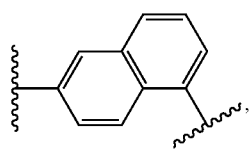

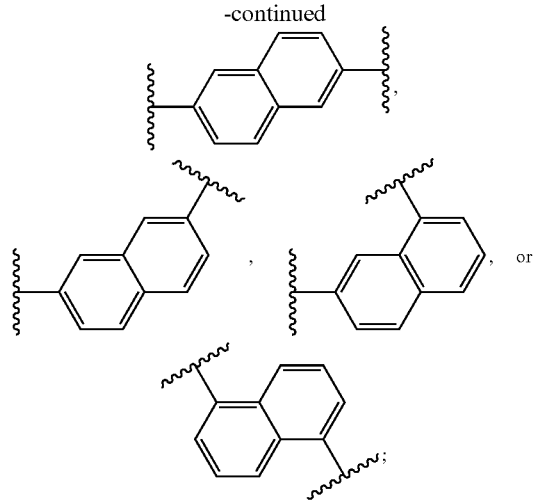

$G^1$ is O, C(O), S, S(O), S(O)$_2$, or $NR^7$; wherein $R^7$ is H, $C_1$-$C_4$ alkyl, or $C_1$-$C_4$alkylcarbonyl;
$G^2$ is

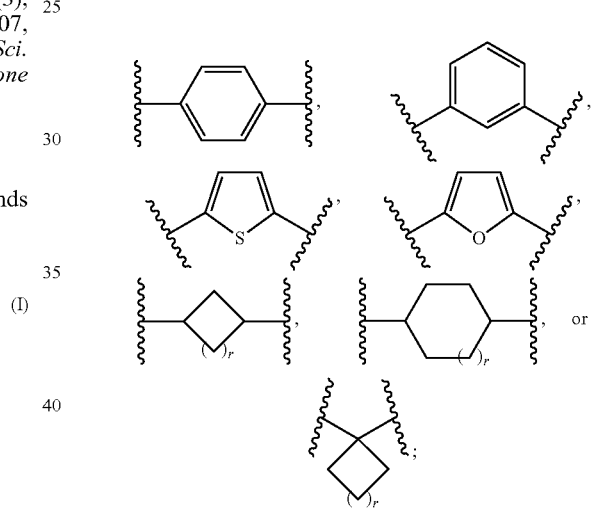

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;
$R^1$ is $COOR^9$, $CONR^9R^{10}$, $CH_2OR^9$, $SO_3R^9$, $SO_2NR^9R^{10}$, $PO(OR^9)_2$, or tetrazol-5-yl;
$R^9$ is H, $C_1$-$C_4$ alkyl, or aryl;
$R^{10}$ is H, $C_1$-$C_4$ alkyl, $COR^{11}$, $OR^9$, or $SO_2R^{11}$;
$R^{11}$ is $C_1$-$C_4$ alkyl;
$R^{12}$, at each occurrence, is independently H or $C_1$-$C_4$alkyl;
$L^3$ is —$C(R^2)_2$—$C(R^3)_2$—, —$C(R^2)$=$C(R^3)$—, —C≡C—, or

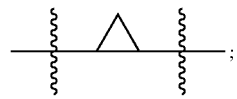

wherein $R^2$ and $R^3$ are each H, $CH_3$, fluoro, or chloro;

$R^4$ and $R^5$ are each independently H or $C_1$-$C_4$ alkyl, wherein no more than one of $R^4$ and $R^5$ is H; or $R^4$ and $R^5$ together with the carbon to which they are attached form a $C_3$-$C_5$ cycloalkyl;

$L^2$ is $C_2$-$C_6$alkylene, or $C_2$-$C_6$alkenylene; wherein the alkylene and alkenylene are optionally substituted with 1, 2, 3, or 4 fluoro substituents;

$R^6$ is aryl or heteroaryl wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy; and r is 0 or 1.

In another aspect, the present invention provides compounds of formula (Ia)

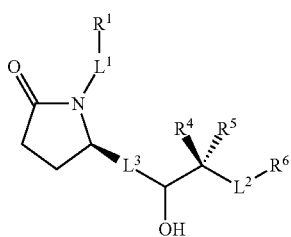

(Ia)

or a pharmaceutically acceptable salt thereof, wherein $R^1$, $R^4$, $R^5$, $R^6$, $L^1$, $L^2$, and $L^3$ are as defined herein.

In another aspect of the invention are compounds of formula (II)

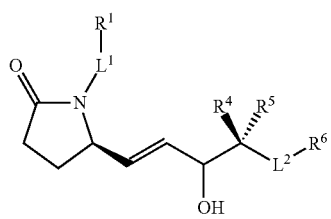

(II)

wherein $R^1$, $R^4$, $R^5$, $R^6$, $L^1$ and $L^2$ are as defined herein.

Another aspect of the present invention relates to pharmaceutical compositions comprising therapeutically effective amounts of a compound described herein or a pharmaceutically acceptable salt, solvate, salt of a solvate, or solvate of a salt thereof, in combination with a pharmaceutically acceptable carrier.

In another aspect, the invention provides compounds that bind to the $EP_4$ receptor with high affinity and agonist activity. In certain embodiments, compounds of the invention may possess selectivity for the $EP_4$ receptor over other EP receptors. In other certain embodiments, compounds of the invention may possess selectivity for the $EP_4$ receptor versus other EP receptors and other prostaglandin receptors.

In another aspect, the present invention provides a method of treating a disease or disorder related to the $EP_4$ receptor by administering to a patient a therapeutically effective amount of a compound or composition of formula (I), (Ia), or (II). Such diseases or disorders include those related to elevated intraocular pressure such as glaucoma. Other diseases or conditions treatable by the compounds and compositions of the invention include those associated with excessive bone loss, such as osteoporosis.

The present invention also provides methods of preparing compounds of formula (I), (Ia), or (II).

In another aspect, the invention provides intermediates useful in the preparation of $EP_4$ agonists. In still another aspect, the invention provides methods of preparing the intermediates.

Further provided herein are the use of the present compounds or pharmaceutically acceptable salts, solvates, salts of solvates, or solvates of salts thereof, in the manufacture of a medicament for the treatment of the diseases or conditions described herein, alone or in combination with one or more pharmaceutically acceptable carrier(s).

DETAILED DESCRIPTION

Definition of Terms

The term "agonist" as used herein refers to a compound, the biological effect of which is to mimic the action of the natural agonist $PGE_2$. An agonist may have full efficacy (i.e., equivalent to $PGE_2$), partial efficacy (lower maximal efficacy compared to $PGE_2$), or super maximal efficacy (higher maximal efficacy compared to $PGE_2$). An agonist with partial efficacy is referred to as a "partial agonist." An agonist with super maximal efficacy is referred to as a "super agonist."

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, means a straight or branched chain hydrocarbon containing at least one carbon-carbon triple bond. Representative examples include propynyl, butynyl, pentynyl, and the like.

The term "alkylene," as used herein, means a divalent group derived from a straight or branched chain saturated hydrocarbon. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

The term "alkenylene," as used herein, means a divalent group derived from a straight or branched chain hydrocarbon containing at least one carbon-carbon double bond. Representative examples of alkenylene include, but are not limited to —CH=CH—, —$CH_2$CH=CH—, and —$CH_2$CH=CH($CH_3$)—.

The term "alkynylene," as used herein, means a divalent group derived from a straight or branched chain hydrocarbon containing at least one carbon-carbon triple bond. Representative examples of alkynylene include, but are not limited to —$CH_2$—C≡C—, —$CH_2CH_2$—C≡C—, and —C≡C—$CH_2$CH($CH_3$)$CH_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkylcarbonyl" as used herein, means an alkyl group, as defined herein, appended to the parent molecular moiety through a C(O) group.

The terms "haloalkyl," "haloalkenyl," and "haloalkynyl" as used herein, mean, respectively an alkyl, alkenyl, or alkynyl group, as defined herein, in which one, two, three, four, five, six, or seven hydrogen atoms are replaced by halogen. For example, representative examples of haloalkyl include, but are not limited to, 2-fluoroethyl, 2,2-difluoroethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "heteroaryl," as used herein, means a monocyclic heteroaryl or a fused bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is an 8- to 12-membered ring system having a monocyclic heteroaryl fused to an additional ring; wherein the additional ring may be aromatic or partially saturated, and may contain additional heteroatoms. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, furopyridinyl, indolyl, indazolyl, isoquinolinyl, naphthyridinyl, oxazolopyridine, quinolinyl, thienopyridinyl, 5,6,7,8-tetrahydroquinolinyl, 6,7-dihydro-5H-cyclopenta[b]pyridinyl, and 2,3-dihydrofuro[3,2-b]pyridinyl. The monocyclic and the bicyclic heteroaryl groups are connected to the parent molecular moiety through any substitutable carbon atom or any substitutable nitrogen atom contained within the groups.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

The term "heterocycle" or "heterocyclic" as used herein, refers to a monocyclic heterocycle, a bicyclic heterocycle, or a spirocyclic heterocycle. The monocyclic heterocycle is a 3, 4, 5, 6, 7, or 8-membered ring containing at least one heteroatom selected from O, N, or S. The 3 or 4 membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The bicyclic heterocycle is a 5-12-membered ring system having a monocyclic heterocycle fused to a phenyl, a saturated or partially saturated carbocyclic ring, or another monocyclic heterocyclic ring. Representative examples of bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4-, 5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. Examples of a spiroheterocycle include, but are not limited to, 5-oxaspiro[3,4]octane and 8-azaspiro[4.5]decane. The monocyclic and bicyclic heterocycle groups of the present invention may contain an alkylene bridge of 1, 2, 3, or 4 carbon atoms, linking two non-adjacent atoms of the group. Examples of such a bridged heterocycle include, but are not limited to, 2-azabicyclo[2.2.1]heptanyl, 2-azabicyclo[2.2.2]octanyl, 1,2,3,4-tetrahydro-1,4-methanoisoquinolinyl, and oxabicyclo[2.2.1]heptanyl. The monocyclic, bicyclic, and spirocyclic heterocycle groups are connected to the parent molecular moiety through any substitutable carbon atom or any substitutable nitrogen atom contained within the group.

Terms such as "alkyl," "cycloalkyl," "alkylene," etc. may be preceded by a designation indicating the number of atoms present in the group in a particular instance (e.g., "$C_3$-$C_{10}$alkyl," "$C_3$-$C_{10}$cycloalkyl," "$C_2$-$C_6$alkynylene," "$C_2$-$C_6$alkenylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_3$-$C_{10}$," the members of the group that follows may have any number of carbon atoms falling within the recited range. A "$C_3$-$C_{10}$alkyl," for example, is an alkyl group having from 3 to 10 carbon atoms, however arranged.

A "patient" as used herein refers to a mammal (e.g., a human) or a bird having a condition that may be treated with compounds of the invention.

Compounds

According to a general aspect of the present invention, there are provided compounds useful as $EP_4$ receptor agonists, as well as compositions and methods relating thereto. Compounds of the invention have the structure set forth in formula (I), (Ia), or (II).

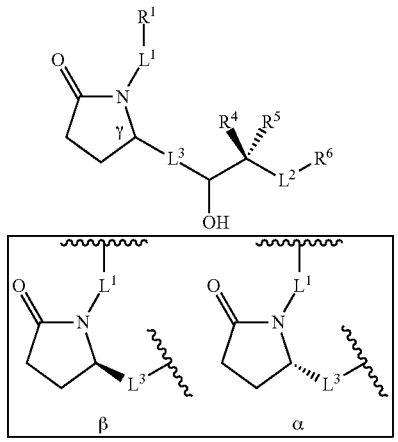

(I)

Formula (I) refers to compounds having either β stereochemistry or a substantially equal mixture of β and α stereochemistries at the γ-position of the lactam ring. Excluded are compounds having pure or substantially pure α stereochemistry at the γ-position.

In some embodiments of the invention, $L^1$ is $C_3$-$C_7$alkylene, $C_3$-$C_7$alkenylene, or $C_3$-$C_7$alkynylene, wherein the $C_3$-$C_7$alkylene, $C_3$-$C_7$alkenylene, and $C_3$-$C_7$alkynylene is optionally substituted with 1, 2, 3, or 4 fluoro substituents. In other embodiments, $L^1$ is $C_3$-$C_7$alkylene, optionally substituted. In some groups of compounds, $L^1$ is n-pentylene, n-hexylene, or n-heptylene each optionally substituted with 1, 2, 3, or 4 fluoro substituents. In subgroups of compounds, $L^1$ is n-hexylene.

In other embodiments, $L^1$ is —$(CH_2)_t$-G-$(CH_2)_p$—; wherein t, p, and G are as defined herein. In some groups of compounds, t and p are both 0. In other groups of compounds, t is 0 and p is 0, 1, 2, or 3. In still other groups of compounds, p is 0 and t is 0, 1, or 2.

In other embodiments, $L^1$ is —$(CH_2)_n$-$G^1$-$(CH_2)_p$—, wherein $G^1$ is as defined herein, n is 1, 2, 3, 4, or 5 and p is 1, 2, or 3.

In still other embodiments, $L^1$ is —$(CH_2)_n$-$G^2$-$(CH_2)_p$—, —$(CH_2)_n$—C≡C-$G^2$-, or —$(CH_2)_n$C(H)=C(H)-$G^2$- wherein $G^2$, n and p are as defined herein.

In still other embodiments, $L^1$ is —$(CH_2)_3$-$G^2$-$(CH_2)_p$—, —$CH_2$—C≡C-$G^2$-, or —$CH_2$—C(H)=C(H)-$G^2$-.

In still other embodiments, $L^1$ is —$(CH_2)_3$-$G^2$-, —$CH_2$—C≡C-$G^2$-, or —$CH_2$—C(H)=C(H)-$G^2$-.

In still other embodiments, $L^1$ is —$(CH_2)_n$-$G^2$-$(CH_2)_p$— wherein $G^2$, n and p are as defined herein. For example, in some groups of compounds, $G^2$ is

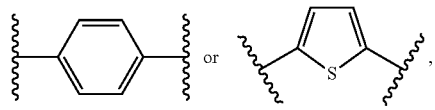

in is 2 and p is 0. In other groups, $G^2$ is

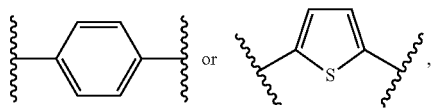 [SMILES: *c1ccc(*)cc1 ; *c1ccc(*)s1]

n is 3 and p is 0. In still other groups, $G^2$ is

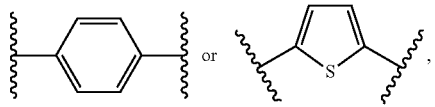 [SMILES: *c1ccc(*)cc1 ; *c1ccc(*)s1]

n is 2 and p is 0, 1, 2, or 3. In yet other groups, $G^2$ is

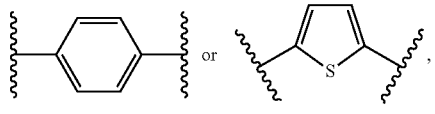

p is 0, and n is 2, 3, 4, or 5. In some subgroups, $G^2$ is

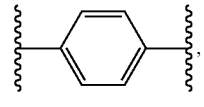

n is 2 and p is 0. In other subgroups, $G^2$ is

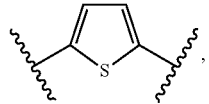

n is 3 and p is 0. In other subgroups, $G^2$ is

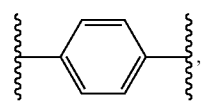

n is 1 and p is 1.

In still other embodiments, $L^1$ is —$(CH_2)_3$-$G^2$-, —$CH_2$—C≡C-$G^2$-, or —$CH_2$—C(H)=C(H)-$G^2$- and $G^2$ is

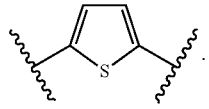

In still other embodiments, $L^1$ is —$(CH_2)_n$—C≡C-$G^2$- or —$(CH_2)_n$—C(H)=C(H)-$G^2$-. For example, in some groups of compounds $G^2$ is

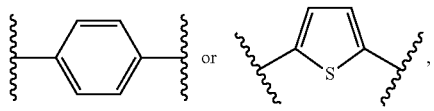 [SMILES: *c1ccc(*)cc1 ; *c1ccc(*)s1]

and n is 1. In certain subgroups of compounds $G^2$ is

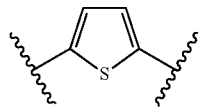 [SMILES: *c1ccc(*)s1]

and n is 1. In other subgroups, $L^1$ is —$(CH_2)_n$—C≡C-$G^2$-, $G^2$ is

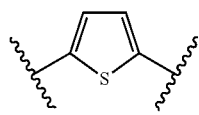

and n is 1. In still other subgroups, $L^1$ is —$(CH_2)_n$—C(H)=C(H)-$G^2$-, $G^2$ is

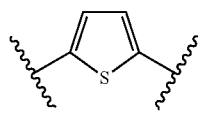 [SMILES: *c1ccc(*)s1]

and n is 1.

In compounds of formula (I), (Ia), or (II), $R^1$ is $COOR^9$, $CONR^9R^{10}$, $CH_2OR^9$, $SO_3R^9$, $SO_2NR^9R^{10}$, $PO(OR^9)_2$, or tetrazol-5-yl; wherein $R^9$ is H, $C_1$-$C_4$ alkyl (e.g., methyl, ethyl) or aryl (e.g., phenyl) and $R^{10}$ is H, $C_1$-$C_4$ alkyl (e.g., methyl, ethyl), $COR^{11}$, $OR^9$, or $SO_2R^{11}$; wherein $R^{11}$ is $C_1$-$C_4$ alkyl (e.g., methyl, ethyl). In one group of compounds, $R^1$ is COOH or $COOCH_3$. In another group of compounds, $R^1$ is COOH.

In compounds of formula (I) or (Ia), $L^3$ is —$C(R^2)_2$—$C(R^3)_2$—, —$C(R^2)$=$C(R^3)$—, —C≡C—, or

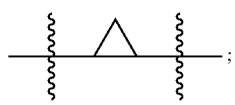

wherein $R^2$ and $R^3$ are each H, $CH_3$, fluoro, or chloro. In some embodiments, $L^3$ is —$C(R^2)_2$—$C(R^3)_2$— and $R^2$ and $R^3$ are each hydrogen. In other embodiments, $L^3$ is —$C(R^2)$=$C(R^3)$— and $R^2$ and $R^3$ are each independently H, $CH_3$, fluoro or chloro. In some groups of compounds, $L^3$ is —$C(R^2)$=$C(R^3)$— and $R^2$ and $R^3$ are hydrogen. In certain subgroups, $L^3$ is

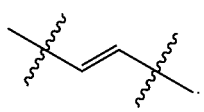 [SMILES: */C=C/* ; "."]

In other embodiments, $L^3$ is —C≡C—. In yet other embodiments, $L^3$ is

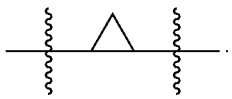

In compounds of formula (I), (Ia), or (II), $R^4$ and $R^5$ are each independently H or $C_1$-$C_4$ alkyl (e.g., methyl, ethyl, etc.), wherein no more than one of $R^4$ and $R^5$ is H; or $R^4$ and $R^5$ together with the carbon to which they are attached form a $C_3$-$C_5$ cycloalkyl (e.g., cyclopropyl). In some embodiments $R^4$ is $C_1$-$C_4$ alkyl (e.g., methyl, ethyl, etc.) and $R^5$ is hydrogen. In yet other embodiments, $R^4$ is hydrogen and $R^5$ is $C_1$-$C_4$ alkyl (e.g., methyl, ethyl, etc.). In some embodiments, $R^4$ is methyl and $R^5$ is hydrogen. In other embodiments, $R^4$ is hydrogen and $R^5$ is methyl.

In the compounds of formula (I), (Ia), or (II), the stereochemistry of the hydroxyl group adjacent the carbon bearing the $R^4$ and $R^5$ groups may be either α or β or a mixture of α and β.

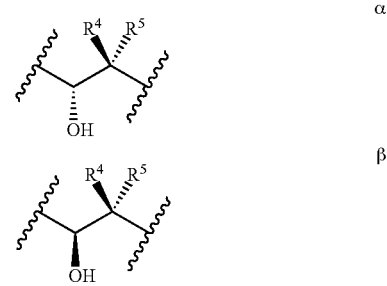

In some embodiments, $L^2$ is $C_2$-$C_6$alkylene or $C_2$-$C_6$alkenylene. The alkylene and alkenylene are optionally substituted with 1, 2, 3, or 4 fluoro substituents. In further embodiments, $L^2$ is $C_2$-$C_6$alkylene (e.g., ethylene, propylene, butylene, pentylene, etc.), optionally substituted. In some groups of compounds, $L^2$ is n-propylene. In some groups of compounds, $L^2$ is n-butylene. In some groups of compounds, $L^2$ is n-pentylene (or amylene). In still other embodiments, $L^2$ is $C_2$-$C_6$alkenylene (e.g., ethenylene, propenylene, butenylene, etc.).

In some embodiments of the invention, $R^6$ is aryl or heteroaryl, each optionally substituted as described herein. In some groups of compounds, $R^6$ is aryl, optionally substituted as described herein. In some groups of compounds, $R^6$ is phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$).

In one aspect of the invention, $L^1$-$R^1$ is $C_3$-$C_7$alkylene-$R^1$, wherein the $C_3$-$C_7$alkylene is optionally substituted with 1, 2, 3, or 4 fluoro substituents; or $L^1$-$R^1$ is —$(CH_2)_n$-$G^2$-$(CH_2)_p$—$R^1$, —$(CH_2)_n$—C≡C-$G^2$-$R^1$, or —$(CH_2)_n$—C(H)=C(H)-$G^2$-$R^1$, wherein n is 1, 2, 3, 4, or 5, p is 0, 1, 2, or 3, and n+p=1, 2, 3, 4, 5, or 6; $G^2$ is

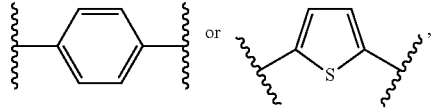

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy; $R^1$ is COOR$^9$; and $R^9$ is H or $C_1$-$C_4$ alkyl. In one embodiment of this aspect of the invention $L^1$-$R^1$ is n-hexylene-COOR$^9$, —(CH$_2$)$_n$-G$^2$-(CH$_2$)$_p$—COOR$^9$, —(CH$_2$)$_n$—C≡C-G$^2$-COOR$^9$, or —(CH$_2$)$_n$—C(H)═C(H)-G$^2$-COOR$^9$; wherein n is 1, 2 or 3, p is 0 or 1; $G^2$ is

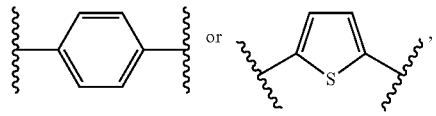

and $R^9$ is H or CH$_3$. In another embodiment of this aspect of the invention $L^1$-$R^1$ is n-hexylene-COOR$^9$, —(CH$_2$)$_n$-G$^2$-(CH$_2$)$_p$—COOR$^9$, —CH$_2$—C≡C-G$^2$-COOR$^9$, or —CH$_2$—C(H)═C(H)-G$^2$-COOR$^9$; wherein n is 2 or 3, p is 0; $G^2$ is

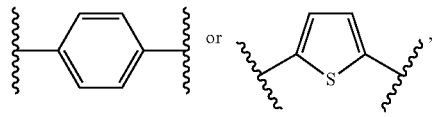

and $R^9$ is H or CH$_3$. In another embodiment of this aspect of the invention $L^1$-$R^1$ is n-hexylene-COOR$^9$, —(CH$_2$)$_3$-G$^2$-COOR$^9$, —CH$_2$—C≡C-G$^2$-COOR$^9$, or —CH$_2$—C(H)═C(H)-G$^2$-COOR$^9$; wherein; $G^2$ is

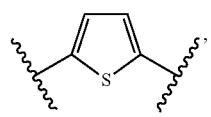

and $R^9$ is H or CH$_3$.

In another embodiment of this aspect of the invention, $L^1$-$R^1$ is $C_3$-$C_7$alkylene-$R^1$ and the alkylene is optionally substituted with 1-4 fluoro substituents. In one group of compounds, for example, $L^1$-$R^1$ is n-pentylene-COOR$^9$, n-hexylene-COOR$^9$, n-heptylene-COOR$^9$, etc., and $R^9$ is H, CH$_3$, or —CH$_2$CH$_3$. In one embodiment, $L^1$-$R^1$ is n-hexylene-COOH, n-hexylene-COOCH$_3$, or n-hexylene-COOCH$_2$CH$_3$.

In another embodiment of this aspect of the invention, $L^1$-$R^1$ is —(CH$_2$)$_n$-G$^2$-(CH$_2$)$_p$—$R^1$; and $G^2$ is

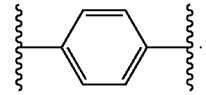

In another embodiment, $L^1$-$R^1$ is —(CH$_2$)$_n$-G$^2$-COOR$^9$ (i.e., p is 0), $G^2$ is

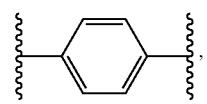

n is 2 or 3, and $R^9$ is H or CH$_3$. In one embodiment, $L^1$-$R^1$ is

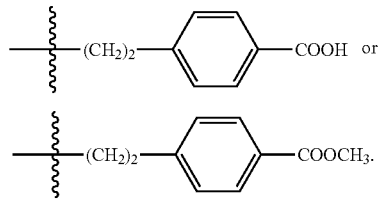

In another embodiment, $L^1$-$R^1$ is

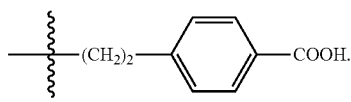

In another embodiment of this aspect of the invention $L^1$-$R^1$ is —(CH$_2$)$_n$-G$^2$-(CH$_2$)$_p$—$R^1$ and $G^2$ is

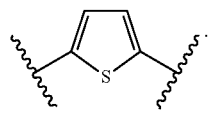

In another embodiment, $L^1$-$R^1$ is —(CH$_2$)$_n$-G$^2$-COOR$^9$ (i.e., p is 0), $G^2$ is

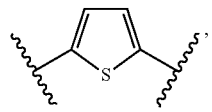

in is 2 or 3; and $R^9$ is H or CH$_3$. In still another embodiment, $L^1$-$R^1$ is

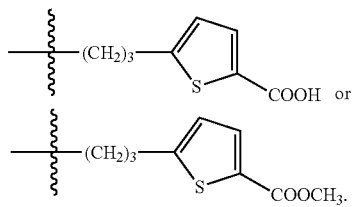

In yet another embodiment, $L^1$-$R^1$ is

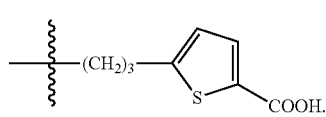

In yet another embodiment, $L^1$-$R^1$ is —(CH$_2$)$_n$—C≡C-G$^2$-COOR$^9$, $G^2$ is

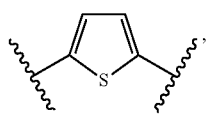

n is 1, and $R^9$ is H or $CH_3$. In another embodiment, $L^1$-$R^1$ is —$(CH_2)_n$—C≡C-$G^2$-$COOR^9$, $G^2$ is

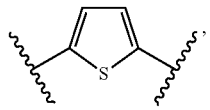

n is 1, and $R^9$ is H.

In another embodiment, $L^1$-$R^1$ is —$(CH_2)_n$—C(H)=C(H)-$G^2$-$COOR^9$, $G^2$ is

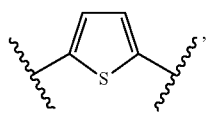

n is 1, and $R^9$ is H or $CH_3$. In another embodiment, $L^1$-$R^1$ is —$(CH_2)_n$—C(H)=C(H)-$G^2$-$COOR^9$, $G^2$ is

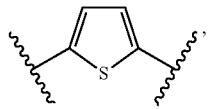

n is 1, and $R^9$ is H.

In another aspect of the invention, $L^2$ is $C_2$-$C_6$alkylene, wherein the alkylene is optionally substituted with 1, 2, 3, or 4 fluoro substituents; $L^3$ is —C($R^2$)=C($R^3$)—; $R^2$ and $R^3$ are each hydrogen; $R^4$ and $R^5$ are independently H or $C_1$-$C_4$ alkyl, wherein no more than one of $R^4$ and $R^5$ is H; and $R^6$ is aryl or heteroaryl, wherein the aryl and heteroaryl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$ alkoxy.

In another aspect of the invention,

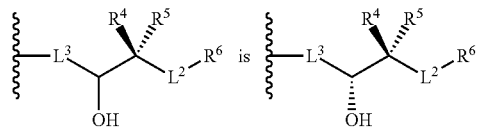

(i.e., the hydroxyl group stereochemistry is o), $L^2$ is $C_2$-$C_6$alkylene, $R^6$ is aryl or heteroaryl, (each optionally substituted as described herein) and $L^3$, $R^4$, and $R^5$ are as defined herein. In a first embodiment of this aspect of the invention, $L^3$ is

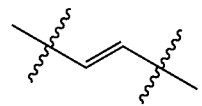 [SMILES: */C=C/*]

and one of $R^4$ and $R^5$ is H and the other is $CH_3$. In one group of compounds according to the first embodiment, $L^2$ is ethylene, n-propylene, n-butylene, or n-pentylene. In a subgroup of compounds $R^6$ is aryl optionally substituted as described herein. In another subgroup, $R^6$ is phenyl optionally substituted as described herein. In another subgroup, $R^4$ is methyl and $R^5$ is hydrogen. In a second embodiment of this aspect of the invention, $L^3$ is —$CH_2$—$CH_2$— and one of $R^4$ and $R^5$ is H and the other is $CH_3$. In a third embodiment of this aspect of the invention $L^3$ is —C≡C— and one of $R^4$ and $R^5$ is H and the other is $CH_3$. In a fourth embodiment of this aspect of the invention, $L^3$ is

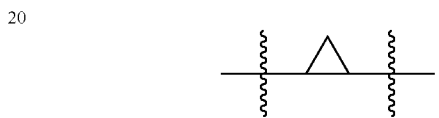

and one of $R^4$ and $R^5$ is H and the other is $CH_3$. Groups of compounds according to the second, third, and fourth embodiments include those where $L^2$ is ethylene, n-propylene, n-butylene, or n-pentylene and $R^6$ is phenyl optionally substituted as described herein.

In another aspect of the invention are compounds of formula (I) or (Ia) wherein:

$L^1$-$R^1$ is $C_3$-$C_7$alkylene-$R^1$, wherein the $C_3$-$C_7$alkylene is optionally substituted with 1, 2, 3, or 4 fluoro substituents; or $L^1$-$R^1$ is —$(CH_2)_n$-$G^2$-$(CH_2)_p$-$R^1$, —$(CH_2)_n$—C≡C-$G^2$-$R^1$, or —$(CH_2)_n$—C(H)=C(H)-$G^2$-$R^1$, wherein n is 1, 2, 3, 4, or 5, p is 0, 1, 2, or 3, and n+p=1, 2, 3, 4, 5, or 6; $G^2$ is

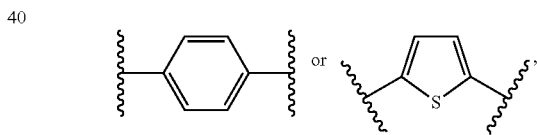

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy; $R^1$ is $COOR^9$; $R^9$ is H or $C_1$-$C_4$ alkyl; and

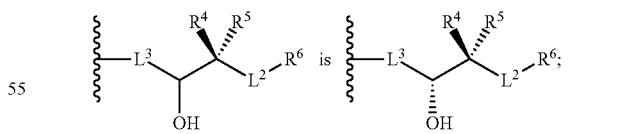

$L^3$ is —C($R^2$)$_2$—C($R^3$)$_2$—, —C($R^2$)=C($R^3$)—, —C≡C—, or

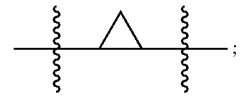

wherein $R^2$ and $R^3$ are each H, $CH_3$, fluoro, or chloro; $R^4$ and $R^5$ are each independently H or $C_1$-$C_4$ alkyl wherein no more than one of $R^4$ and $R^5$ is H; or $R^4$ and $R^5$ together with the carbon to which they are attached form a $C_3$-$C_5$ cycloalkyl; $L^2$ is $C_2$-$C_6$alkylene or $C_2$-$C_6$alkenylene wherein the $C_2$-$C_6$alkylene and $C_2$-$C_6$alkenylene are optionally substituted with 1, 2, 3, or 4 fluoro substituents; $R^6$ is aryl or heteroaryl, wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In one embodiment according to the foregoing aspect of the invention, $L^3$ is

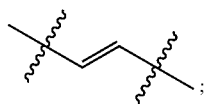 [SMILES: */C=C/*]

$R^4$ and $R^5$ are independently H or $C_1$-$C_4$ alkyl, wherein no more than one of $R^4$ and $R^5$ is H; $L^2$ is $C_2$-$C_6$alkylene; and $R^6$ is aryl; wherein the aryl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and $C_1$-$C_3$alkylene $C_1$-$C_3$alkoxy.

In one group of compounds according to the foregoing embodiment, $L^2$ is n-propylene; whereas in another group of compounds $L^2$ is n-butylene.

In one group of compounds according to the foregoing embodiment, $L^1$-$R^1$ is $C_3$-$C_7$alkylene-$R^1$; or $L^1$-$R^1$ is —$(CH_2)_n$-$G^2$-$(CH_2)_p$-$R^1$, —$(CH_2)_n$—C_C-$G^2$-$R^1$, or —$(CH_2)_n$—C(H)=C(H)-$G^2$-$R^1$, wherein n is 1, 2 or 3 and p is 0, 1, or 2, and n+p=1, 2, 3, or 4; $G^2$ is

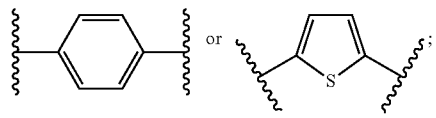

$R^1$ is COOR$^9$; $R^9$ is H or $C_1$-$C_4$ alkyl; one of $R^4$ and R is $CH_3$ and the other is H; $L^2$ is ethylene, n-propylene, n-butylene, or n-pentylene; and $R^6$ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

In another group of compounds according to the foregoing embodiment, $L^1$-$R^1$ is $C_3$-$C_7$alkylene $R^1$; or $L^1$-$R^1$ is —$(CH_2)_n$-$G^2$-$(CH_2)_p$—$R^1$, —$(CH_2)_n$—C≡C-$G^2$-$R^1$, or $(CH_2)_n$—C(H)=C(H)-$G^2$-$R^1$, wherein n is 1, 2 or 3 and p is 0; $G^2$ is

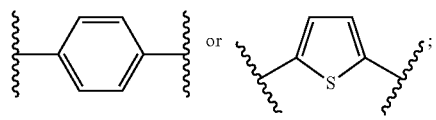

$R^1$ is COOR$^9$; $R^9$ is H or $C_1$-$C_4$ alkyl; one of $R^4$ and $R^5$ is $CH_3$ and the other is H; $L^2$ is ethylene, n-propylene, n-butylene, or n-pentylene; and $R^6$ is phenyl or $C_1$-$C_6$alkyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and $C_1$-$C_3$alkylene-$C_1$-$C_3$alkoxy.

In another group of compounds according to the foregoing embodiment, $L^1$-$R^1$ is $C_3$-$C_7$alkylene-$R^1$; or $L^1$-$R^1$ is —$(CH_2)_3$-$G^2$-$R^1$, —$CH_2$—C≡C-$G^2$-$R^1$, or —$CH_2$—C(H)=C(H)-$G^2$-$R^1$, wherein $G^2$ is

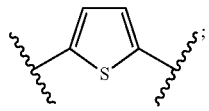

$L^2$ is ethylene, n-propylene, n-butylene, or n-pentylene; and $R^6$ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

In another group of compounds according to the foregoing embodiment, $L^1$-$R^1$ is $C_3$-$C_7$alkylene-$R^1$; or $L^1$-$R^1$ is —$(CH_2)_3$-$G^2$-$R^1$, —$CH_2$—C≡C-$G^2$-$R^1$, or —$CH_2$—C(H)=C(H)-$G^2$-$R^1$, wherein $G^2$ is

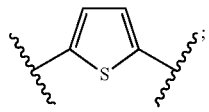

$R^1$ is COOR$^9$; $R^9$ is H or $C_1$-$C_4$ alkyl; one of $R^4$ and $R^5$ is $CH_3$ and the other is H; $L^2$ is ethylene, n-propylene, n-butylene, or n-pentylene; and $R^6$ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

In another group of compounds according to the foregoing embodiment, $R^4$ and $R^5$ are independently H or $CH_3$, wherein no more than one of $R^4$ and $R^5$ is H; $R^6$ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy. In one subgroup of compounds, $L^1$ is $C_3$-$C_7$alkylene or —$(CH_2)_n$-$G^2$-$(CH_2)_p$—, wherein n is 2 or 3 and p is 0; and $G^2$ is

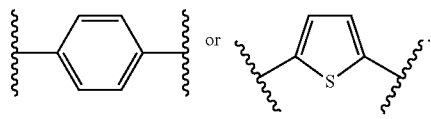

In another subgroup of compounds, $L^1$ is $C_3$-$C_7$alkylene or —$(CH_2)_n$-$G^2$-; n is 2 or 3; $G^2$ is

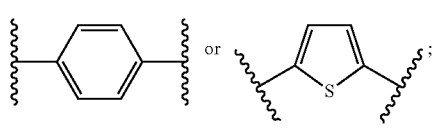 [SMILES: *c1ccc(*)cc1 ; "or" ; *c1ccc(*)s1 ; ";"]

$R^4$ is methyl; $R^5$ is hydrogen; $L^2$ is ethylene, propylene, n-butylene, or n-pentylene; and $R^6$ is phenyl or phenyl optionally substituted. In another subgroup of compounds, $L^1$ is $C_3$-$C_7$alkylene; $R^4$ is methyl; $R^5$ is hydrogen; $L^2$ is ethylene, propylene, n-butylene, or n-pentylene; and $R^6$ is phenyl or phenyl optionally substituted. In another subgroup of compounds, $L^1$ is —$(CH_2)_n$-$G^2$-, wherein n is 2 or 3; $G^2$ is

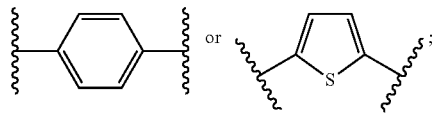 [SMILES: *c1ccc(*)cc1 ; "or" ; *c1ccc(*)s1 ; ";"]

$R^4$ is methyl; $R^5$ is hydrogen; $L^2$ is ethylene, propylene, n-butylene, or n-pentylene; and $R^6$ is phenyl or phenyl optionally substituted.

In another subgroup of compounds, $L^1$ is n-hexylene, —$(CH_2)_n$-$G^2$-$(CH_2)_p$—, —$CH_2$—C≡C-$G^2$-, or —$CH_2$—C(H)=C(H)-$G^2$-, wherein n is 1, 2 or 3; p is 0 or 1, and n+p=2 or 3; $G^2$ is

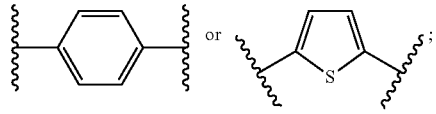 [SMILES: *c1ccc(*)cc1 ; "or" ; *c1ccc(*)s1 ; ";"]

$R^1$ is $COOR^9$; $R^9$ is H or $CH_3$; $L^2$ is propylene or butylene; and $R^6$ is phenyl.

In another subgroup of compounds, $L^1$ is $C_3$-$C_7$alkylene, —$(CH_2)_3$-$G^2$-, —$CH_2$—C≡C-$G^2$-, or —$CH_2$—C(H)=C(H)-$G^2$-; $G^2$ is

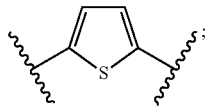

$R^4$ is methyl; $R^5$ is hydrogen; $L^2$ is ethylene, propylene, n-butylene, or n-pentylene; and $R^6$ is phenyl or phenyl optionally substituted. In another subgroup of compounds, $L^1$ is n-hexylene, —$(CH_2)_3$-$G^2$-, —$CH_2$—C≡C-$G^2$-, or —$CH_2$—C(H)=C(H)-$G^2$-; $G^2$ is

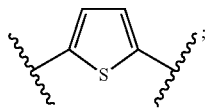

$R^1$ is $COOR^9$; $R^9$ is H or $CH_3$; $L^2$ is propylene or butylene; and $R^6$ is phenyl.

In another group of compounds according to the foregoing embodiment $L^1$ is $C_3$-$C_7$alkylene, wherein the $C_3$-$C_7$alkylene is optionally substituted with 1, 2, 3, or 4 fluoro substituents.

In another subgroup of compounds according to the foregoing embodiment $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

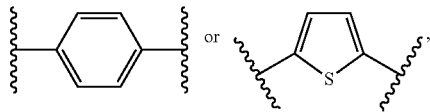

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

In a subgroup of compounds $L^2$ is n-propylene; and $L^1$ is $C_3$-$C_7$alkylene, wherein the $C_3$-$C_7$alkylene is optionally substituted with 1, 2, 3, or 4 fluoro substituents. In another subgroup of compounds according to the foregoing embodiment $L^2$ is n-propylene; $L^1$ is —$(CH_2)_n$-$G^2$-$(CH_2)_p$—, —$(CH_2)_n$—C≡C-$G^2$-, or —$(CH_2)$—C(H)=C(H)-$G^2$-, wherein n is 1, 2, 3, 4, or 5, p is 0, 1, 2, or 3, and n+p=1, 2, 3, 4, 5, or 6; and $G^2$ is

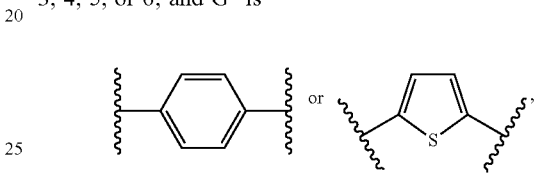

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

In another subgroup of compounds $L^2$ is n-butylene; and $L^1$ is $C_3$-$C_7$alkylene, wherein the $C_3$-$C_7$alkylene is optionally substituted with 1, 2, 3, or 4 fluoro substituents. In another subgroup of compounds according to the foregoing embodiment $L^2$ is n-butylene; and $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

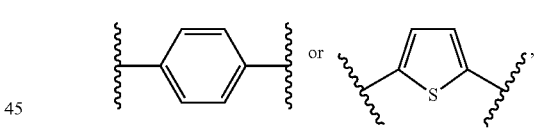

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

In another subgroup of compounds $L^2$ is n-pentylene; and $L^1$ is $C_3$-$C_7$alkylene, wherein the $C_3$-$C_7$alkylene is optionally substituted with 1, 2, 3, or 4 fluoro substituents. In another subgroup of compounds according to the foregoing embodiment $L^2$ is n-pentylene; and $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

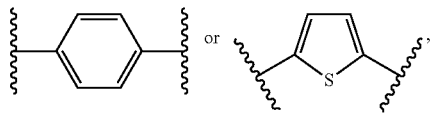

wherein G² is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

In another aspect, the invention provides a compound selected from the group consisting of:

methyl 7-((R)-2-((3S,4S,E)-3-hydroxy-4-methyl-6-phenylhex-1-en-1-yl)-5-oxopyrrolidin-1-yl)heptanoate;
(Z)-methyl 7-((R)-2-((3S,4S,E)-3-hydroxy-4-methyl-6-phenylhex-1-en-1-yl)-5-oxopyrrolidin-1-yl)hept-5-enoate;
methyl 4-((2-((R)-2-((3S,4S,E)-3-hydroxy-4-methyl-6-phenylhex-1-en-1-yl)-5-oxopyrrolidin-1-yl)ethyl)thio)butanoate;
methyl 5-(3-((R)-2-((3S,4S,E)-3-hydroxy-4-methyl-6-phenylhex-1-en-1-yl)-5-oxopyrrolidin-1-yl)propyl)thiophene-2-carboxylate;
methyl 5-(3-((R)-2-((3S,4S,E)-3-hydroxy-4-methyl-6-phenylhex-1-en-1-yl)-5-oxopyrrolidin-1-yl)prop-1-yn-1-yl)thiophene-2-carboxylate;
methyl 5-((Z)-3-((R)-2-((3S,4S,E)-3-hydroxy-4-methyl-6-phenylhex-1-en-1-yl)-5-oxopyrrolidin-1-yl)prop-1-en-1-yl)thiophene-2-carboxylate;
methyl 4-(2-((R)-2-((3S,4S,E)-3-hydroxy-4-methyl-6-phenylhex-1-en-1-yl)-5-oxopyrrolidin-1-yl)ethyl)benzoate;
methyl 3-(3-((R)-2-((3S,4S,E)-3-hydroxy-4-methyl-6-phenylhex-1-en-1-yl)-5-oxopyrrolidin-1-yl)propyl)benzoate;
7-((R)-2-((3S,4S,E)-3-hydroxy-4-methyl-6-phenylhex-1-en-1-yl)-5-oxopyrrolidin-1-yl)heptanoic acid;
(Z)-7-((R)-2-((3S,4S,E)-3-hydroxy-4-methyl-6-phenylhex-1-en-1-yl)-5-oxopyrrolidin-1-yl)hept-5-enoic acid;
4-((2-((R)-2-((3S,4S,E)-3-hydroxy-4-methyl-6-phenylhex-1-en-1-yl)-5-oxopyrrolidin-1-yl)ethyl)thio)butanoic acid;
5-(3-((R)-2-((3S,4S,E)-3-hydroxy-4-methyl-6-phenylhex-1-en-1-yl)-5-oxopyrrolidin-1-yl)propyl)thiophene-2-carboxylic acid;
5-(3-((R)-2-((3S,4S,E)-3-hydroxy-4-methyl-6-phenylhex-1-en-1-yl)-5-oxopyrrolidin-1-yl)prop-1-yn-1-yl)thiophene-2-carboxylic acid;
5-((Z)-3-((R)-2-((3S,4S,E)-3-hydroxy-4-methyl-6-phenylhex-1-en-1-yl)-5-oxopyrrolidin-1-yl)prop-1-en-1-yl)thiophene-2-carboxylic acid;
4-(2-((R)-2-((3S,4S,E)-3-hydroxy-4-methyl-6-phenylhex-1-en-1-yl)-5-oxopyrrolidin-1-yl)ethyl)benzoic acid;
3-(3-((R)-2-((3S,4S,E)-3-hydroxy-4-methyl-6-phenylhex-1-en-1-yl)-5-oxopyrrolidin-1-yl)propyl)benzoic acid;
methyl 7-((S)-2-((3R,4S)-3-hydroxy-4-methyl-6-phenylhexyl)-5-oxopyrrolidin-1-yl)heptanoate;
(Z)-methyl 7-((S)-2-((3R,4S)-3-hydroxy-4-methyl-6-phenylhexyl)-5-oxopyrrolidin-1-yl)hept-5-enoate;
methyl 4-((2-((S)-2-((3R,4S)-3-hydroxy-4-methyl-6-phenylhexyl)-5-oxopyrrolidin-1-yl)ethyl)thio)butanoate;
methyl 5-(3-((S)-2-((3R,4S)-3-hydroxy-4-methyl-6-phenylhexyl)-5-oxopyrrolidin-1-yl)propyl)thiophene-2-carboxylate;
methyl 5-(3-((S)-2-((3R,4S)-3-hydroxy-4-methyl-6-phenylhexyl)-5-oxopyrrolidin-1-yl)prop-1-yn-1-yl)thiophene-2-carboxylate;
methyl 5-((Z)-3-((S)-2-((3R,4S)-3-hydroxy-4-methyl-6-phenylhexyl)-5-oxopyrrolidin-1-yl)prop-1-en-1-yl)thiophene-2-carboxylate;
methyl 4-(2-((S)-2-((3R,4S)-3-hydroxy-4-methyl-6-phenylhexyl)-5-oxopyrrolidin-1-yl)ethyl)benzoate;
methyl 3-(3-((S)-2-((3R,4S)-3-hydroxy-4-methyl-6-phenylhexyl)-5-oxopyrrolidin-1-yl)propyl)benzoate;
7-((S)-2-((3R,4S)-3-hydroxy-4-methyl-6-phenylhexyl)-5-oxopyrrolidin-1-yl)heptanoic acid;
(Z)-7-((S)-2-((3R,4S)-3-hydroxy-4-methyl-6-phenylhexyl)-5-oxopyrrolidin-1-yl)hept-5-enoic acid;
4-((2-((S)-2-((3R,4S)-3-hydroxy-4-methyl-6-phenylhexyl)-5-oxopyrrolidin-1-yl)ethyl)thio)butanoic acid;
5-(3-((S)-2-((3R,4S)-3-hydroxy-4-methyl-6-phenylhexyl)-5-oxopyrrolidin-1-yl)propyl)thiophene-2-carboxylic acid;
5-(3-((S)-2-((3R,4S)-3-hydroxy-4-methyl-6-phenylhexyl)-5-oxopyrrolidin-1-yl)prop-1-yn-1-yl)thiophene-2-carboxylic acid;
5-((Z)-3-((S)-2-((3R,4S)-3-hydroxy-4-methyl-6-phenylhexyl)-5-oxopyrrolidin-1-yl)prop-1-en-1-yl)thiophene-2-carboxylic acid;
4-(2-((S)-2-((3R,4S)-3-hydroxy-4-methyl-6-phenylhexyl)-5-oxopyrrolidin-1-yl)ethyl)benzoic acid;
3-(3-((S)-2-((3R,4S)-3-hydroxy-4-methyl-6-phenylhexyl)-5-oxopyrrolidin-1-yl)propyl)benzoic acid;
methyl 7-((R)-2-((3S,4S,E)-3-hydroxy-4-methyl-7-phenylhept-1-en-1-yl)-5-oxopyrrolidin-1-yl)heptanoate;
methyl 7-((R)-2-((3S,4R,E)-3-hydroxy-4-methyl-7-phenylhept-1-en-1-yl)-5-oxopyrrolidin-1-yl)heptanoate;
(Z)-methyl 7-((R)-2-((3S,4S,E)-3-hydroxy-4-methyl-7-phenylhept-1-en-1-yl)-5-oxopyrrolidin-1-yl)hept-5-enoate;
methyl 4-((2-((R)-2-((3S,4S,E)-3-hydroxy-4-methyl-7-phenylhept-1-en-1-yl)-5-oxopyrrolidin-1-yl)ethyl)thio)butanoate;
methyl 5-(3-((R)-2-((3S,4S,E)-3-hydroxy-4-methyl-7-phenylhept-1-en-1-yl)-5-oxopyrrolidin-1-yl)propyl)thiophene-2-carboxylate;
methyl 5-(3-((R)-2-((3S,4R,E)-3-hydroxy-4-methyl-7-phenylhept-1-en-1-yl)-5-oxopyrrolidin-1-yl)propyl)thiophene-2-carboxylate;
methyl 5-(3-((R)-2-((3S,4S,E)-3-hydroxy-4-methyl-7-phenylhept-1-en-1-yl)-5-oxopyrrolidin-1-yl)prop-1-yn-1-yl)thiophene-2-carboxylate;
methyl 5-((Z)-3-((R)-2-((3S,4S,E)-3-hydroxy-4-methyl-7-phenylhept-1-en-1-yl)-5-oxopyrrolidin-1-yl)prop-1-en-1-yl)thiophene-2-carboxylate;
methyl 4-(2-((R)-2-((3S,4S,E)-3-hydroxy-4-methyl-7-phenylhept-1-en-1-yl)-5-oxopyrrolidin-1-yl)ethyl)benzoate;
methyl 3-(3-((R)-2-((3S,4S,E)-3-hydroxy-4-methyl-7-phenylhept-1-en-1-yl)-5-oxopyrrolidin-1-yl)propyl)benzoate;
7-((R)-2-((3S,4S,E)-3-hydroxy-4-methyl-7-phenylhept-1-en-1-yl)-5-oxopyrrolidin-1-yl)heptanoic acid;
7-((R)-2-((3S,4R,E)-3-hydroxy-4-methyl-7-phenylhept-1-en-1-yl)-5-oxopyrrolidin-1-yl)heptanoic acid;
(Z)-7-((R)-2-((3S,4S,E)-3-hydroxy-4-methyl-7-phenylhept-1-en-1-yl)-5-oxopyrrolidin-1-yl)hept-5-enoic acid;
4-((2-((R)-2-((3S,4S,E)-3-hydroxy-4-methyl-7-phenylhept-1-en-1-yl)-5-oxopyrrolidin-1-yl)ethyl)thio)butanoic acid;
5-(3-((R)-2-((3S,4S,E)-3-hydroxy-4-methyl-7-phenylhept-1-en-1-yl)-5-oxopyrrolidin-1-yl)propyl)thiophene-2-carboxylic acid;
5-(3-((R)-2-((3S,4R,E)-3-hydroxy-4-methyl-7-phenylhept-1-en-1-yl)-5-oxopyrrolidin-1-yl)propyl)thiophene-2-carboxylic acid;
5-(3-((R)-2-((3S,4S,E)-3-hydroxy-4-methyl-7-phenylhept-1-en-1-yl)-5-oxopyrrolidin-1-yl)prop-1-yn-1-yl)thiophene-2-carboxylic acid;
5-((Z)-3-((R)-2-((3S,4S,E)-3-hydroxy-4-methyl-7-phenylhept-1-en-1-yl)-5-oxopyrrolidin-1-yl)prop-1-en-1-yl)thiophene-2-carboxylic acid;
4-(2-((R)-2-((3S,4S,E)-3-hydroxy-4-methyl-7-phenylhept-1-en-1-yl)-5-oxopyrrolidin-1-yl)ethyl)benzoic acid;
3-(3-((R)-2-((3S,4S,E)-3-hydroxy-4-methyl-7-phenylhept-1-en-1-yl)-5-oxopyrrolidin-1-yl)propyl)benzoic acid;

methyl 7-((S)-2-((3R,4S)-3-hydroxy-4-methyl-7-phenylheptyl)-5-oxopyrrolidin-1-yl)heptanoate;
methyl 7-((S)-2-((3R,4R)-3-hydroxy-4-methyl-7-phenylheptyl)-5-oxopyrrolidin-1-yl)heptanoate;
(Z)-methyl 7-((S)-2-((3R,4S)-3-hydroxy-4-methyl-7-phenylheptyl)-5-oxopyrrolidin-1-yl)hept-5-enoate;
methyl 4-((2-((S)-2-((3R,4S)-3-hydroxy-4-methyl-7-phenylheptyl)-5-oxopyrrolidin-1-yl)ethyl)thio)butanoate;
methyl 5-(3-((S)-2-((3R,4S)-3-hydroxy-4-methyl-7-phenylheptyl)-5-oxopyrrolidin-1-yl)propyl)thiophene-2-carboxylate;
methyl 5-(3-((S)-2-((3R,4R)-3-hydroxy-4-methyl-7-phenylheptyl)-5-oxopyrrolidin-1-yl)propyl)thiophene-2-carboxylate;
methyl 5-(3-((S)-2-((3R,4S)-3-hydroxy-4-methyl-7-phenylheptyl)-5-oxopyrrolidin-1-yl)prop-1-yn-1-yl)thiophene-2-carboxylate;
methyl 5-((Z)-3-((S)-2-((3R,4S)-3-hydroxy-4-methyl-7-phenylheptyl)-5-oxopyrrolidin-1-yl)prop-1-en-1-yl)thiophene-2-carboxylate;
methyl 4-(2-((S)-2-((3R,4S)-3-hydroxy-4-methyl-7-phenylheptyl)-5-oxopyrrolidin-1-yl)ethyl)benzoate;
methyl 3-(3-((S)-2-((3R,4S)-3-hydroxy-4-methyl-7-phenylheptyl)-5-oxopyrrolidin-1-yl)propyl)benzoate;
7-((S)-2-((3R,4S)-3-hydroxy-4-methyl-7-phenylheptyl)-5-oxopyrrolidin-1-yl)heptanoic acid;
7-((S)-2-((3R,4R)-3-hydroxy-4-methyl-7-phenylheptyl)-5-oxopyrrolidin-1-yl)heptanoic acid;
(Z)-7-((S)-2-((3R,4S)-3-hydroxy-4-methyl-7-phenylheptyl)-5-oxopyrrolidin-1-yl)hept-5-enoic acid;
4-((2-((S)-2-((3R,4S)-3-hydroxy-4-methyl-7-phenylheptyl)-5-oxopyrrolidin-1-yl)ethyl)thio)butanoic acid;
5-(3-((S)-2-((3R,4S)-3-hydroxy-4-methyl-7-phenylheptyl)-5-oxopyrrolidin-1-yl)propyl)thiophene-2-carboxylic acid;
5-(3-((S)-2-((3R,4S)-3-hydroxy-4-methyl-7-phenylheptyl)-5-oxopyrrolidin-1-yl)propyl)thiophene-2-carboxylic acid;
5-(3-((S)-2-((3R,4S)-3-hydroxy-4-methyl-7-phenylheptyl)-5-oxopyrrolidin-1-yl)prop-1-yn-1-yl)thiophene-2-carboxylic acid;
5-((Z)-3-((S)-2-((3R,4S)-3-hydroxy-4-methyl-7-phenylheptyl)-5-oxopyrrolidin-1-yl)prop-1-en-1-yl)thiophene-2-carboxylic acid;
4-(2-((S)-2-((3R,4S)-3-hydroxy-4-methyl-7-phenylheptyl)-5-oxopyrrolidin-1-yl)ethyl)benzoic acid;
3-(3-((S)-2-((3R,4S)-3-hydroxy-4-methyl-7-phenylheptyl)-5-oxopyrrolidin-1-yl)propyl)benzoic acid;
methyl 7-((R)-2-((3S,4S,E)-3-hydroxy-4-methyl-8-phenyloct-1-en-1-yl)-5-oxopyrrolidin-1-yl)heptanoate;
methyl 7-((R)-2-((3S,4R,E)-3-hydroxy-4-methyl-8-phenyloct-1-en-1-yl)-5-oxopyrrolidin-1-yl)heptanoate;
(Z)-methyl 7-((R)-2-((3S,4S,E)-3-hydroxy-4-methyl-8-phenyloct-1-en-1-yl)-5-oxopyrrolidin-1-yl)hept-5-enoate;
methyl 4-((2-((R)-2-((3S,4S,E)-3-hydroxy-4-methyl-8-phenyloct-1-en-1-yl)-5-oxopyrrolidin-1-yl)ethyl)thio)butanoate;
methyl 5-(3-((R)-2-((3S,4S,E)-3-hydroxy-4-methyl-8-phenyloct-1-en-1-yl)-5-oxopyrrolidin-1-yl)propyl)thiophene-2-carboxylate;
methyl 5-(3-((R)-2-((3S,4R,E)-3-hydroxy-4-methyl-8-phenyloct-1-en-1-yl)-5-oxopyrrolidin-1-yl)propyl)thiophene-2-carboxylate;
methyl 5-(3-((R)-2-((3S,4S,E)-3-hydroxy-4-methyl-8-phenyloct-1-en-1-yl)-5-oxopyrrolidin-1-yl)prop-1-yn-1-yl)thiophene-2-carboxylate;
methyl 5-((Z)-3-((R)-2-((3S,4S,E)-3-hydroxy-4-methyl-8-phenyloct-1-en-1-yl)-5-oxopyrrolidin-1-yl)prop-1-en-1-yl)thiophene-2-carboxylate;
methyl 4-(2-((R)-2-((3S,4S,E)-3-hydroxy-4-methyl-8-phenyloct-1-en-1-yl)-5-oxopyrrolidin-1-yl)ethyl)benzoate;
methyl 3-(3-((R)-2-((3S,4S,E)-3-hydroxy-4-methyl-8-phenyloct-1-en-1-yl)-5-oxopyrrolidin-1-yl)propyl)benzoate;
7-((R)-2-((3S,4S,E)-3-hydroxy-4-methyl-8-phenyloct-1-en-1-yl)-5-oxopyrrolidin-1-yl)heptanoic acid;
7-((R)-2-((3S,4R,E)-3-hydroxy-4-methyl-8-phenyloct-1-en-1-yl)-5-oxopyrrolidin-1-yl)heptanoic acid;
(Z)-7-((R)-2-((3S,4S,E)-3-hydroxy-4-methyl-8-phenyloct-1-en-1-yl)-5-oxopyrrolidin-1-yl)hept-5-enoic acid;
4-((2-((R)-2-((3S,4S,E)-3-hydroxy-4-methyl-8-phenyloct-1-en-1-yl)-5-oxopyrrolidin-1-yl)ethyl)thio)butanoic acid;
5-(3-((R)-2-((3S,4S,E)-3-hydroxy-4-methyl-8-phenyloct-1-en-1-yl)-5-oxopyrrolidin-1-yl)propyl)thiophene-2-carboxylic acid;
5-(3-((R)-2-((3S,4R,E)-3-hydroxy-4-methyl-8-phenyloct-1-en-1-yl)-5-oxopyrrolidin-1-yl)propyl)thiophene-2-carboxylic acid;
5-(3-((R)-2-((3S,4S,E)-3-hydroxy-4-methyl-8-phenyloct-1-en-1-yl)-5-oxopyrrolidin-1-yl)prop-1-yn-1-yl)thiophene-2-carboxylic acid;
5-((Z)-3-((R)-2-((3S,4S,E)-3-hydroxy-4-methyl-8-phenyloct-1-en-1-yl)-5-oxopyrrolidin-1-yl)prop-1-en-1-yl)thiophene-2-carboxylic acid;
4-(2-((R)-2-((3S,4S,E)-3-hydroxy-4-methyl-8-phenyloct-1-en-1-yl)-5-oxopyrrolidin-1-yl)ethyl)benzoic acid;
3-(3-((R)-2-((3S,4S,E)-3-hydroxy-4-methyl-8-phenyloct-1-en-1-yl)-5-oxopyrrolidin-1-yl)propyl)benzoic acid;
methyl 7-((S)-2-((3R,4S)-3-hydroxy-4-methyl-8-phenyloctyl)-5-oxopyrrolidin-1-yl)heptanoate;
methyl 7-((S)-2-((3R,4R)-3-hydroxy-4-methyl-8-phenyloctyl)-5-oxopyrrolidin-1-yl)heptanoate;
(Z)-methyl 7-((S)-2-((3R,4S)-3-hydroxy-4-methyl-8-phenyloctyl)-5-oxopyrrolidin-1-yl)hept-5-enoate;
methyl 4-((2-((S)-2-((3R,4S)-3-hydroxy-4-methyl-8-phenyloctyl)-5-oxopyrrolidin-1-yl)ethyl)thio)butanoate;
methyl 5-(3-((S)-2-((3R,4S)-3-hydroxy-4-methyl-8-phenyloctyl)-5-oxopyrrolidin-1-yl)propyl)thiophene-2-carboxylate;
methyl 5-(3-((S)-2-((3R,4R)-3-hydroxy-4-methyl-8-phenyloctyl)-5-oxopyrrolidin-1-yl)propyl)thiophene-2-carboxylate;
methyl 5-(3-((S)-2-((3R,4S)-3-hydroxy-4-methyl-8-phenyloctyl)-5-oxopyrrolidin-1-yl)prop-1-yn-1-yl)thiophene-2-carboxylate;
methyl 5-((Z)-3-((S)-2-((3R,4S)-3-hydroxy-4-methyl-8-phenyloctyl)-5-oxopyrrolidin-1-yl)prop-1-en-1-yl)thiophene-2-carboxylate;
methyl 4-(2-((S)-2-((3R,4S)-3-hydroxy-4-methyl-8-phenyloctyl)-5-oxopyrrolidin-1-yl)ethyl)benzoate;
methyl 3-(3-((S)-2-((3R,4S)-3-hydroxy-4-methyl-8-phenyloctyl)-5-oxopyrrolidin-1-yl)propyl)benzoate;
7-((S)-2-((3R,4S)-3-hydroxy-4-methyl-8-phenyloctyl)-5-oxopyrrolidin-1-yl)heptanoic acid;
7-((S)-2-((3R,4R)-3-hydroxy-4-methyl-8-phenyloctyl)-5-oxopyrrolidin-1-yl)heptanoic acid;
(Z)-7-((S)-2-((3R,4S)-3-hydroxy-4-methyl-8-phenyloctyl)-5-oxopyrrolidin-1-yl)hept-5-enoic acid;
4-((2-((S)-2-((3R,4S)-3-hydroxy-4-methyl-8-phenyloctyl)-5-oxopyrrolidin-1-yl)ethyl)thio)butanoic acid;
5-(3-((S)-2-((3R,4S)-3-hydroxy-4-methyl-8-phenyloctyl)-5-oxopyrrolidin-1-yl)propyl)thiophene-2-carboxylic acid;

5-(3-((S)-2-((3R,4R)-3-hydroxy-4-methyl-8-phenyloctyl)-5-oxopyrrolidin-1-yl)propyl)thiophene-2-carboxylic acid;

5-(3-((S)-2-((3R,4S)-3-hydroxy-4-methyl-8-phenyloctyl)-5-oxopyrrolidin-1-yl)prop-1-yn-1-yl)thiophene-2-carboxylic acid;

5-((Z)-3-((S)-2-((3R,4S)-3-hydroxy-4-methyl-8-phenyloctyl)-5-oxopyrrolidin-1-yl)prop-1-en-1-yl)thiophene-2-carboxylic acid;

4-(2-((S)-2-((3R,4S)-3-hydroxy-4-methyl-8-phenyloctyl)-5-oxopyrrolidin-1-yl)ethyl)benzoic acid;

3-(3-((S)-2-((3R,4S)-3-hydroxy-4-methyl-8-phenyloctyl)-5-oxopyrrolidin-1-yl)propyl)benzoic acid;

methyl 7-((R)-2-((3S,4S,E)-3-hydroxy-4-methyl-9-phenyl-non-1-en-1-yl)-5-oxopyrrolidin-1-yl)heptanoate;

methyl 7-((R)-2-((3S,4R,E)-3-hydroxy-4-methyl-9-phenyl-non-1-en-1-yl)-5-oxopyrrolidin-1-yl)heptanoate;

(Z)-methyl 7-((R)-2-((3S,4S,E)-3-hydroxy-4-methyl-9-phenylnon-1-en-1-yl)-5-oxopyrrolidin-1-yl)hept-5-enoate;

methyl 4-((2-((R)-2-((3S,4S,E)-3-hydroxy-4-methyl-9-phenylnon-1-en-1-yl)-5-oxopyrrolidin-1-yl)ethyl)thio)butanoate;

methyl 5-(3-((R)-2-((3S,4S,E)-3-hydroxy-4-methyl-9-phenylnon-1-en-1-yl)-5-oxopyrrolidin-1-yl)propyl)thiophene-2-carboxylate;

methyl 5-(3-((R)-2-((3S,4R,E)-3-hydroxy-4-methyl-9-phenylnon-1-en-1-yl)-5-oxopyrrolidin-1-yl)propyl)thiophene-2-carboxylate;

methyl 5-(3-((R)-2-((3S,4S,E)-3-hydroxy-4-methyl-9-phenylnon-1-en-1-yl)-5-oxopyrrolidin-1-yl)prop-1-yn-1-yl)thiophene-2-carboxylate;

methyl 5-((Z)-3-((R)-2-((3S,4S,E)-3-hydroxy-4-methyl-9-phenylnon-1-en-1-yl)-5-oxopyrrolidin-1-yl)prop-1-en-1-yl)thiophene-2-carboxylate;

methyl 4-(2-((R)-2-((3S,4S,E)-3-hydroxy-4-methyl-9-phenylnon-1-en-1-yl)-5-oxopyrrolidin-1-yl)ethyl)benzoate;

methyl 3-(3-((R)-2-((3S,4S,E)-3-hydroxy-4-methyl-9-phenylnon-1-en-1-yl)-5-oxopyrrolidin-1-yl)propyl)benzoate;

7-((R)-2-((3S,4S,E)-3-hydroxy-4-methyl-9-phenylnon-1-en-1-yl)-5-oxopyrrolidin-1-yl)heptanoic acid;

7-((R)-2-((3S,4R,E)-3-hydroxy-4-methyl-9-phenylnon-1-en-1-yl)-5-oxopyrrolidin-1-yl)heptanoic acid;

(Z)-7-((R)-2-((3S,4S,E)-3-hydroxy-4-methyl-9-phenylnon-1-en-1-yl)-5-oxopyrrolidin-1-yl)hept-5-enoic acid;

4-((2-((R)-2-((3S,4S,E)-3-hydroxy-4-methyl-9-phenylnon-1-en-1-yl)-5-oxopyrrolidin-1-yl)ethyl)thio)butanoic acid;

5-(3-((R)-2-((3S,4S,E)-3-hydroxy-4-methyl-9-phenylnon-1-en-1-yl)-5-oxopyrrolidin-1-yl)propyl)thiophene-2-carboxylic acid;

5-(3-((R)-2-((3S,4R,E)-3-hydroxy-4-methyl-9-phenylnon-1-en-1-yl)-5-oxopyrrolidin-1-yl)propyl)thiophene-2-carboxylic acid;

5-(3-((R)-2-((3S,4S,E)-3-hydroxy-4-methyl-9-phenylnon-1-en-1-yl)-5-oxopyrrolidin-1-yl)prop-1-yn-1-yl)thiophene-2-carboxylic acid;

5-((Z)-3-((R)-2-((3S,4S,E)-3-hydroxy-4-methyl-9-phenylnon-1-en-1-yl)-5-oxopyrrolidin-1-yl)prop-1-en-1-yl)thiophene-2-carboxylic acid;

4-(2-((R)-2-((3S,4S,E)-3-hydroxy-4-methyl-9-phenylnon-1-en-1-yl)-5-oxopyrrolidin-1-yl)ethyl)benzoic acid;

3-(3-((R)-2-((3S,4S,E)-3-hydroxy-4-methyl-9-phenylnon-1-en-1-yl)-5-oxopyrrolidin-1-yl)propyl)benzoic acid;

methyl 7-((S)-2-((3R,4S)-3-hydroxy-4-methyl-9-phenylnonyl)-5-oxopyrrolidin-1-yl)heptanoate;

methyl 7-((S)-2-((3R,4R)-3-hydroxy-4-methyl-9-phenylnonyl)-5-oxopyrrolidin-1-yl)heptanoate;

(Z)-methyl 7-((S)-2-((3R,4S)-3-hydroxy-4-methyl-9-phenylnonyl)-5-oxopyrrolidin-1-yl)hept-5-enoate;

methyl 4-((2-((S)-2-((3R,4S)-3-hydroxy-4-methyl-9-phenylnonyl)-5-oxopyrrolidin-1-yl)ethyl)thio)butanoate;

methyl 5-(3-((S)-2-((3R,4S)-3-hydroxy-4-methyl-9-phenylnonyl)-5-oxopyrrolidin-1-yl)propyl)thiophene-2-carboxylate;

methyl 5-(3-((S)-2-((3R,4R)-3-hydroxy-4-methyl-9-phenylnonyl)-5-oxopyrrolidin-1-yl)propyl)thiophene-2-carboxylate;

methyl 5-(3-((S)-2-((3R,4S)-3-hydroxy-4-methyl-9-phenylnonyl)-5-oxopyrrolidin-1-yl)prop-1-yn-1-yl)thiophene-2-carboxylate;

methyl 5-((Z)-3-((S)-2-((3R,4S)-3-hydroxy-4-methyl-9-phenylnonyl)-5-oxopyrrolidin-1-yl)prop-1-en-1-yl)thiophene-2-carboxylate;

methyl 4-(2-((S)-2-((3R,4S)-3-hydroxy-4-methyl-9-phenylnonyl)-5-oxopyrrolidin-1-yl)ethyl)benzoate;

methyl 3-(3-((S)-2-((3R,4S)-3-hydroxy-4-methyl-9-phenylnonyl)-5-oxopyrrolidin-1-yl)propyl)benzoate;

7-((S)-2-((3R,4S)-3-hydroxy-4-methyl-9-phenylnonyl)-5-oxopyrrolidin-1-yl)heptanoic acid;

7-((S)-2-((3R,4R)-3-hydroxy-4-methyl-9-phenylnonyl)-5-oxopyrrolidin-1-yl)heptanoic acid;

(Z)-7-((S)-2-((3R,4S)-3-hydroxy-4-methyl-9-phenylnonyl)-5-oxopyrrolidin-1-yl)hept-5-enoic acid;

[0239] 4-((2-((S)-2-((3R,4S)-3-hydroxy-4-methyl-9-phenylnonyl)-5-oxopyrrolidin-1-yl)ethyl)thio)butanoic acid;

5-(3-((S)-2-((3R,4S)-3-hydroxy-4-methyl-9-phenylnonyl)-5-oxopyrrolidin-1-yl)propyl)thiophene-2-carboxylic acid;

5-(3-((S)-2-((3R,4R)-3-hydroxy-4-methyl-9-phenylnonyl)-5-oxopyrrolidin-1-yl)propyl)thiophene-2-carboxylic acid;

5-(3-((S)-2-((3R,4S)-3-hydroxy-4-methyl-9-phenylnonyl)-5-oxopyrrolidin-1-yl)prop-1-yn-1-yl)thiophene-2-carboxylic acid;

5-((Z)-3-((S)-2-((3R,4S)-3-hydroxy-4-methyl-9-phenylnonyl)-5-oxopyrrolidin-1-yl)prop-1-en-1-yl)thiophene-2-carboxylic acid;

4-(2-((S)-2-((3R,4S)-3-hydroxy-4-methyl-9-phenylnonyl)-5-oxopyrrolidin-1-yl)ethyl)benzoic acid;

3-(3-((S)-2-((3R,4S)-3-hydroxy-4-methyl-9-phenylnonyl)-5-oxopyrrolidin-1-yl)propyl)benzoic acid;

methyl 7-((R)-2-((3S,4S,E)-3-hydroxy-4-methyl-7-phenylhept-1-en-1-yl)-5-oxopyrrolidin-1-yl)hept-5-ynoate; and 7-((R)-2-((3S,4S,E)-3-hydroxy-4-methyl-7-phenylhept-1-en-1-yl)-5-oxopyrrolidin-1-yl)hept-5-ynoic acid; or a pharmaceutically acceptable salt thereof.

Compounds described herein may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The various stereoisomers (including enantiomers and diastereomers) and mixtures thereof of the compounds described are also contemplated. Individual stereoisomers of compounds described may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. All various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae within this specification can represent only one of the possible tautomeric forms. It is to be understood that encompassed herein are any tautomeric form, and mixtures thereof, and is not to be limited merely to any one tautomeric form utilized within the naming of the compounds or formulae.

Additionally, unless otherwise stated, the structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in a biological assay, or as $EP_4$ receptor agonists.

Also contemplated as part of the invention are compounds formed by synthetic means or formed in vivo by biotransformation or by chemical means. For example, certain compounds of the invention may function as prodrugs that are converted to other compounds of the invention upon administration to a subject.

Methods of Treatment

The compounds of the invention are $EP_4$ receptor agonists and are useful in treating or preventing conditions or diseases responsive to an $EP_4$ receptor agonist. Conditions or diseases treatable with compounds of the invention include elevated intraocular pressure, glaucoma, ocular hypertension, dry eye, macular edema, macular degeneration, alopecia (alone or in combination with, for example, an L-PGDS inhibitor or an H-PGDS inhibitor or in combination with both an L-PGDS inhibitor and H-PGDS inhibitor; Garza, L. A. et al, *Science Translational Medicine*, 2012, 4(126), 126ra34), cerebralvascular accident (Liang, X. et al, *Journal of Clinical Investigation*, 2011, 121(11), 4362-4371), brain damage due to trauma, neuropathic pain (e.g., diabetic neuropathy, sciatica, post-herpetic neuralgia, HIV-related neuropathy, trigeminal neuralgia, ductus arteriosis, chemotherapy-induced pain), low bone density due to osteoporosis (Cameron, K. O. et al, *Bioorganic and Medicinal Chemistry Letters*, 2006, 16, 1799-1802) or glucocorticoid treatment, bone fracture, and bone loss due to periodontal disease, surgical procedures, cancer, or trauma. Further uses of the compounds of the invention include use in increasing bone density in preparation of bone for receiving dental or orthopedic implants, coating of implants for enhanced osseointegration, and use in all forms of spinal fusion.

The present invention provides methods of treatment comprising administering to a patient in need thereof: (i) a therapeutically effective amount of a compound of formula (I), (Ia), or (II), or a pharmaceutically acceptable salt thereof, or a solvate of either; or (ii) a composition comprising any of the foregoing compound, salt, or solvate and a pharmaceutically acceptable carrier.

In one aspect, the invention provides a method of treating glaucoma, osteoporosis, bone fracture, low bone density due to periodontal disease, or neuropathic pain.

In another aspect, the invention provides a method of stimulating bone formation. According to this aspect of the invention, one embodiment provides a method of treating osteoporosis, bone fracture, and periodontal disease. In another embodiment, the compound or composition of the invention is administered alone. In still another embodiment, the compound or composition is administered in combination with one or more additional therapeutic agents to treat bone loss or osteoporosis. Compounds of the invention can be used in combination other agents useful in treating or preventing bone loss such as an organic bisphosphonate (e.g., alendronic acid or sodium alendronate); a cathepsin K inhibitor; an estrogen or an estrogen receptor modulator; calcitonin; an inhibitor of osteoclast proton ATPase; an inhibitor of HMG-CoA reductase; an integrin receptor antagonist; a RANKL inhibitor such as denosumab; a bone anabolic agent, such as PTH; a bone morphogenetic agent such as BMP-2, BMP-4, and BMP-7; Vitamin D or a synthetic Vitamin D analogue such as ED-70; an androgen or an androgen receptor modulator, a SOST inhibitor; and the pharmaceutically acceptable salts and mixtures thereof. A preferred combination is a compound of the present invention and an organic bisphosphonate.

In another aspect, the invention provides a method of lowering intraocular pressure. According to this aspect of the invention, one embodiment provides a method of treating glaucoma. In another embodiment, the compound or composition of the invention is administered alone. In still another embodiment, the compound or composition is administered in combination with one or more additional therapeutic agents that lower intraocular pressure such as a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, or para-aminoclonidine, a carbonic anhydrase inhibitor such as dorzolamide, acetazolamide, metazolamide or brinzolamide; and a prostaglandin such as latanoprost, travaprost, or unoprostone, and the pharmaceutically acceptable salts and mixtures thereof.

In still another aspect, the invention provides a method of treating neuropathic pain. According to this aspect of the invention, one embodiment provides a method of treating diabetic neuropathy, sciatica, post-herpetic neuralgia, HIV-related neuropathy, trigeminal neuralgia, or chemotherapy-induced pain. In another embodiment, the compound or composition of the invention is administered alone. In still another embodiment, the compound or composition is administered in combination with one or more additional therapeutic agents that treat neuropathic pain such as gabapentin, pregabalin, duloxetine, and lamotrigine, and the pharmaceutically acceptable salts and mixtures thereof.

Compounds described herein can be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions may require such repeated or chronic administration of the compounds. Compounds described herein may become more effective upon repeated or chronic administration such that the therapeutically effective doses on repeated or chronic administration can be lower than the therapeutically effective dose from a single administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

In one aspect of the invention, compounds of the invention, or a pharmaceutically acceptable salt thereof, or a solvate of either; or (ii) a composition comprising any of the foregoing compound, salt, or solvate and a pharmaceutically acceptable carrier are administered as the active pharmaceutical agent. In another aspect, compounds of the invention or a pharmaceutically acceptable salt thereof, or a solvate of either; or (ii) a composition comprising any of the foregoing compound, salt, or solvate and a pharmaceutically acceptable carrier are administered to a subject and the administered compounds are converted to the active pharmaceutical agent in the subject by chemical or biotransformation.

Ophthalmic formulations of this compound may contain from 0.001 to 5% and especially 0.001 to 0.1% of active agent. Higher dosages as, for example, up to about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

Compounds may be administered orally once or several times per day each in an amount of from 0.001 mg to 100 mg per adult, preferably about 0.01 to about 10 mg per adult. Compounds may also be administered parenterally once or several times per day each in an amount of from 0.1 ng to 10 mg per adult or continuously administered into a vein for 1 hour to 24 hours per day. Compounds may also be administered locally to stimulate bone formation in an amount from 0.0001 µg to 500 µg.

Pharmaceutical Compositions

Pharmaceutical compositions comprise compounds described herein, pharmaceutically acceptable salts thereof, or solvates of either. The pharmaceutical compositions comprising the compound, salt, or solvate described herein can be formulated together with one or more non-toxic pharmaceutically acceptable carriers, either alone or in combination with one or more other medicaments as described hereinabove.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The pharmaceutical compositions can be administered to humans, other mammals, and birds orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The pharmaceutical compositions can further be administered to humans, other mammals, and birds locally to the desired site of action; for example, into a bone void such as a tooth socket defect, adjacent to an alveolar bone, or a bone defect caused by surgery, trauma, or disease.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, poly(lactic-co-glycolic acid), microcrystalline cellulose, aluminum metahydroxide, bentonite, agar-agar, tragacanth, collagen sponge, demineralized bone matrix, and mixtures thereof.

The compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to compounds described herein, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., Methods in Cell Biology, Volume XIV, Academic Press, New York, N.Y. (1976), p. 33 et seq.

Dosage forms for topical administration of compounds described herein include powders, sprays, ointments and inhalants. The active compounds can be mixed under sterile conditions with a pharmaceutically acceptable carrier and any needed preservatives, buffers or propellants which can be required. Opthalmic formulations, eye ointments, powders and solutions are also contemplated as being within the scope.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Compounds described herein can exist in unsolvated as well as solvated forms, including hydrated forms, such as hemi-hydrates. In general, the solvated forms, with pharmaceutically acceptable solvents such as water and ethanol, among others, are equivalent to the unsolvated forms.

CHEMISTRY AND EXAMPLES

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well-known and commonly used in the art.

It will be appreciated that the synthetic schemes and specific examples are illustrative and are not to be read as limiting the scope of the invention. Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. The skilled artisan will also appreciate that not all of the substituents in the compounds of formula (I), (Ia), or (II) will tolerate certain reaction conditions employed to synthesize the compounds. Routine experimentation, including appropriate manipulation of the reaction conditions, reagents and sequence of the synthetic route, protection and deprotection may be required in the case of particular compounds. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3 d ed.), John Wiley & Sons, NY (1999), which is incorporated herein by reference in its entirety.

Furthermore, the skilled artisan will appreciate that in some cases, the order in which moieties are introduced may vary. The particular order of steps required to produce the compounds of formula (I), (Ia), (II) is dependent upon the particular compounds being synthesized, the starting compound, and the relative stability of the substituted moieties. Thus, synthesis of the present compounds may be accomplished by methods analogous to those described in the synthetic schemes described herein and in the specific examples, with routine experimentation (e.g., manipulation of the reaction conditions, reagents, and sequence of the synthetic steps).

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Systematic names of compound structures have been generated by the Convert-Structure-to-Name function of Chem & Bio Draw 12.0 Ultra by CambridgeSoft®, which uses the Cahn-Ingold-Prelog rules for stereochemistry. When discussing individual atomic positions of compound structures, an alternative continuous numbering scheme for the lactams as described below may be used.

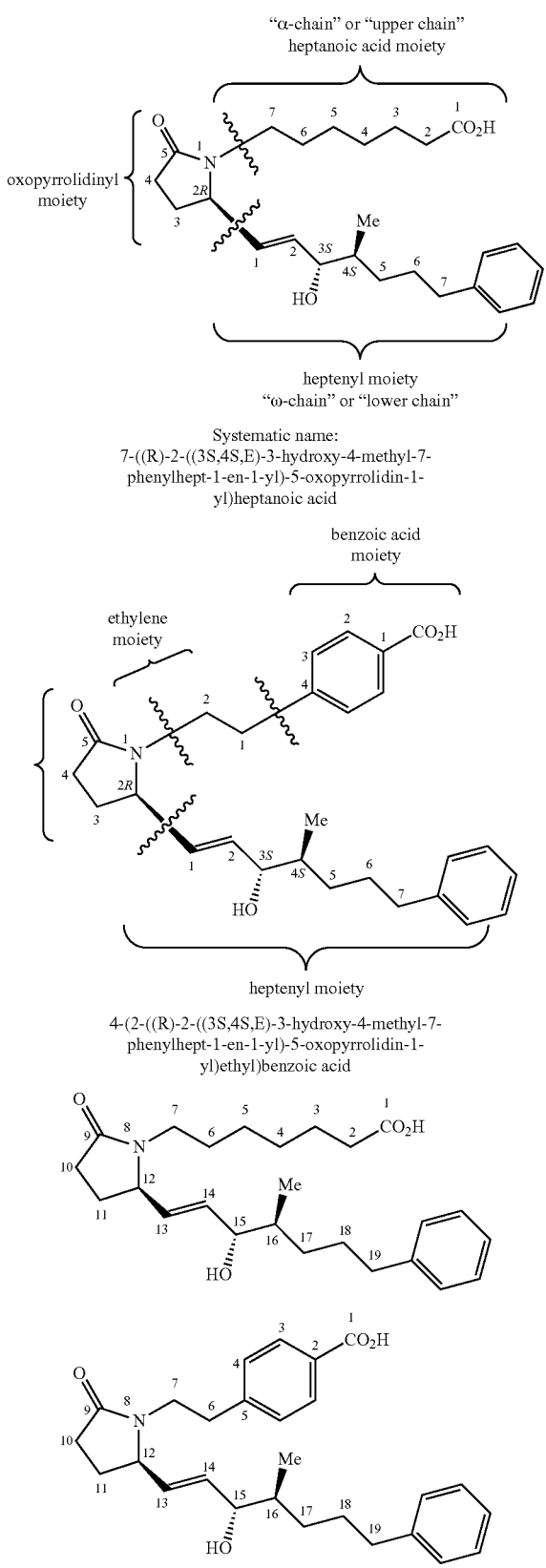

Systematic name:
7-((R)-2-((3S,4S,E)-3-hydroxy-4-methyl-7-phenylhept-1-en-1-yl)-5-oxopyrrolidin-1-yl)heptanoic acid 4-(2-((R)-2-((3S,4S,E)-3-hydroxy-4-methyl-7-phenylhept-1-en-1-yl)-5-oxopyrrolidin-1-yl)ethyl)benzoic acid Alternative atom-position numbering schemes for γ-lactams (also known as oxopyrrolidines or pyrrolidinones)

Liquid chromatography—mass spectra (LC/MS) were obtained using an Agilent LC/MSD G1946D or an Agilent 1100 Series LC/MSD Trap G2435A. Quantifications were obtained on a Cary 50 Bio UV-visible spectrophotometer.

$^1$H, $^{13}$C, and $^{19}$F Nuclear magnetic resonance (NMR) spectra were obtained using a Varian INOVA nuclear magnetic resonance spectrometer at 400, 100, and 376 MHz, respectively.

High performance liquid chromatography (HPLC) analytical separations were performed on an Agilent 1100 or Agilent 1200 HPLC analytical system and followed by an Agilent Technologies G1315B Diode Array Detector set at or near the UV$_{max}$ 260 nm.

High performance liquid chromatography (HPLC) preparatory separations were performed on a Gilson preparative HPLC system or an Agilent 1100 preparative HPLC system and followed by an Agilent Technologies G1315B Diode Array Detector set at or near the UV$_{max}$ 260 nm.

Analytical chiral HPLC separations were performed on an Agilent 1100 analytical system and followed by an Agilent Technologies G1315B Diode Array Detector set at or near the UV$_{max}$ 260 nm.

Thin layer chromatography (TLC) analyses were performed on Uniplate™ 250 silica gel plates (Analtech, Inc. Catalog No. 02521) and were typically developed for visualization using a diluted sulfuric acid spray like 50 volume % in water or 10 volume % in methanol.

When used in the present application, the following abbreviations have the meaning set out below:
Ac is acetyl;
ACN is acetonitrile;
BBr$_3$ is boron tribromide;
Bn is benzyl;
BnNH$_2$ is benzylamine;
BSA is bovine serum albumin;
CH$_2$Cl$_2$ is dichloromethane;
CHCl$_3$ is chloroform;
CDCl$_3$ is deuterochloroform;
CSA is camphorsulfonic acid;
DCC is N,N'-dicyclohexylcarbodiimide;
DME is 1,2-dimethoxyethane;
DMF is N,N-dimethylformamide;
DMSO is dimethyl sulfoxide;
DBU is 1,8-diazabicyclo[5.4.0]undec-7-ene;
DIA is diisopropylamine;
DMAP is 4-dimethylaminopyridine;
EDC/EDAC is N-(3-dimethylaminopropyl)-N'-ethylcarbodiimide hydrochloride;
EDTA is ethylenediaminetetraacetic acid;
EE is ethoxyeth-1-yl;
ee is enantiomeric excess;
EIA is enzyme immunoassay;
Et is ethyl;
EtOAc is ethyl acetate;
EtOH is ethanol;
Et$_3$N is triethylamine;
HCl is hydrogen chloride;
HOBt is 1-hydroxybenzotriazole;
Me is methyl;
MeOH is methanol;
MTBE is methyl tert-butyl ether;
NaOMe is sodium methoxide;
nBuLi or n-BuLi is n-butyllithium;
NHS is N-hydroxysuccinimide;
NMP is 1-methyl-2-pyrrolidinone;
PG is a protecting group;
Ph is phenyl;

Pd(PPh$_3$)$_4$ is tetrakis(triphenylphosphine)palladium;
PhMe is toluene;
rt is room temperature;
TBAF is tetrabutylammonium fluoride;
TBS or TBDMS is tert-butyldimethylsilyl;
tBu or t-Bu is tert-butyl;
TEA is triethylamine;
TFA is trifluoroacetic acid;
THF is tetrahydrofuran;
TMS is trimethylsilyl; and
Tris-HCl is 2-amino-2-(hydroxymethyl)-1,3-propanediol hydrochloride.

Compounds of the present invention may be prepared from commercially available 5-oxopyrrolidine-2-carboxylic acid (pyroglutamic acid) (1) by general routes illustrated in Scheme 1.

carbon single, double, or triple bond) with the appropriate lower chain carbon atom to provide the corresponding compound (I).

Alternatively, compounds of the present invention, (I), may be prepared from 1, for example, by a process that comprises first installing the lower chain with a carbon-carbon bond forming reaction, wherein the hydroxymethyl group carbon atom attached to the γ-position of the lactam ring of starting material 1 forms a covalent bond (carbon-carbon single, double, or triple bond) with the appropriate lower chain carbon atom to provide the corresponding 1+lower chain intermediate shown in Scheme 1. The installation of the lower chain may be followed by a process that comprises installation of the upper chain by way of nitrogen-carbon bond forming reaction, wherein the nitrogen atom of

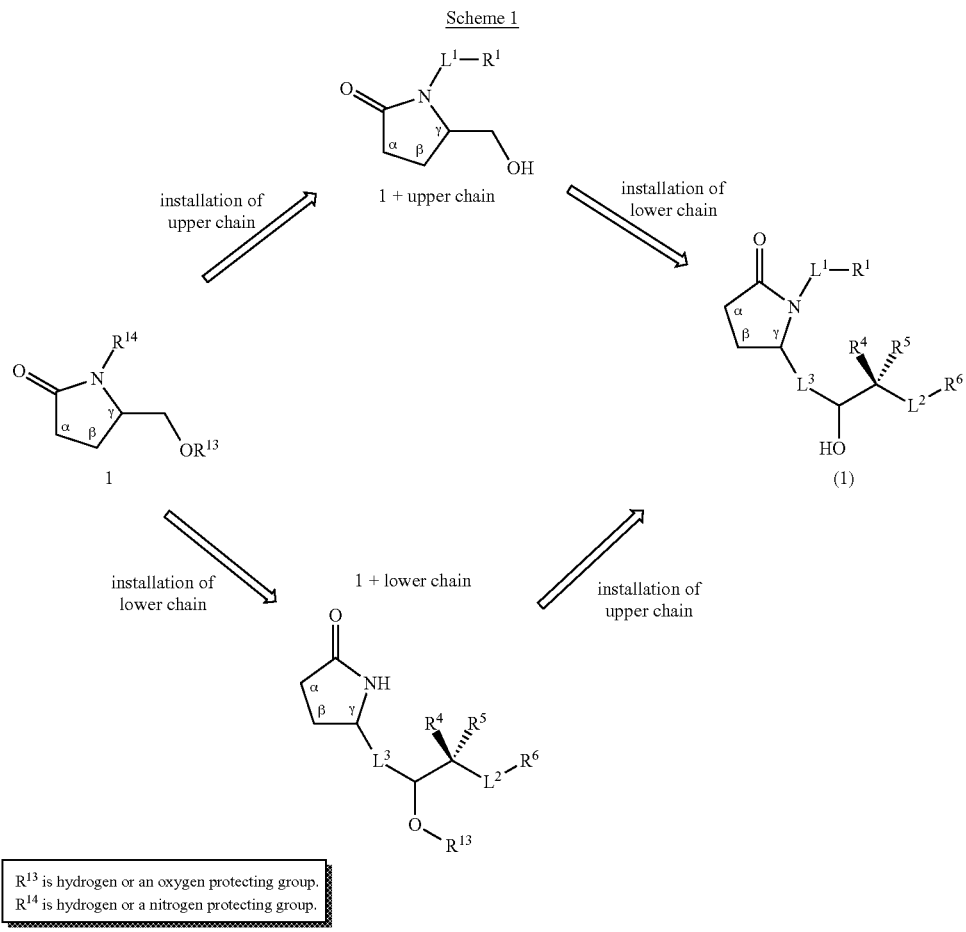

Scheme 1

R$^{13}$ is hydrogen or an oxygen protecting group.
R$^{14}$ is hydrogen or a nitrogen protecting group.

Compounds of the present invention, (I), may be prepared from 1, for example, by a process that comprises first installing the upper chain with a nitrogen-carbon bond forming reaction, wherein the nitrogen atom of the γ-lactam ring of 1 forms a covalent bond with the appropriate upper chain carbon atom to provide the corresponding 1+upper chain intermediate shown in Scheme 1. The installation of the upper chain may be followed by a process that comprises installation of the lower chain by way of a carbon-carbon bond forming reaction, wherein the hydroxymethyl group carbon atom attached to the γ-position of the lactam ring of intermediate 1+upper chain forms a covalent bond (carbonthe γ-lactam ring of 1+lower chain forms a covalent bond with the appropriate upper chain carbon atom to provide the corresponding compound (I).

In some aspects of the present invention, the synthetic route to a compound (I) comprises a process wherein certain intermediates 1+upper chain may undergo chemical reaction or a series of chemical reactions, which are known in the art or disclosed herein, that chemically modify the upper chain such that chemical installation and/or modification of the lower chain is facilitated.

In further aspects of the present invention, the synthetic route to a compound (I) comprises a process wherein a certain intermediate 1+upper chain may undergo chemical reaction or a series of chemical reactions, which are known in the art or disclosed herein, that chemically modify the upper chain such that at least one particular functional group or other structural feature not incorporated into said intermediate is incorporated into the structure of invention compound (I).

In some aspects of the present invention, the synthetic route to a compound (I) comprises a process wherein certain intermediates 1+lower chain may undergo chemical reaction or a series of chemical reactions, which are known in the art or disclosed herein, that chemically modify the lower chain such that chemical installation and/or modification of the upper chain is facilitated.

In further aspects of the present invention, the synthetic route to a compound (I) comprises a process wherein a certain intermediate 1+lower chain may undergo chemical reaction or a series of chemical reactions, which are known in the art or disclosed herein, that chemically modify the lower chain such that at least one particular functional group or other structural feature not incorporated into said intermediate is incorporated into the structure of invention compound (I).

Synthetic routes utilized to prepare compounds of the present invention typically proceed through a carbon-carbon double bond formation (olefination) step to install the compound's lower chain. The olefination may be accomplished by the interaction of an appropriate aldehyde intermediate with an appropriate nucleophilic carbanion species. Such methods may include Wittig reactions, wherein the nucleophilic carbanion species is an appropriate organic phosphonium ylide. Another carbon-carbon bond forming reaction that may be employed is a Horner-Wadsworth-Emmons reaction, wherein the coupling partner with the aldehyde is an appropriate organic phosphonate carbanion. Published reviews describing the general scope and mechanism along with various protocols for these types of olefination reactions include the following:

Boutagy, J. and Thomas, R. *Chemical Reviews*, 1974, 74, 87-99.
Wadsworth, W. S., Jr. *Organic Reactions*, 1977, 25, 73-253.
Walker, B. J. in *Organophosphorous Reagents in Organic Synthesis*, Cadogan, J. I. G., Ed.; Academic Press: New York, 1979, pp. 155-205.
Schlosser, M. et al., *Phosphorous and Sulfur and the Related Elements*, 1983, 18(2-3), 171-174.
Maryanoff, B. E. and Reitz, A. B. *Chemical Reviews*, 1989, 89(4), 863-927.
Kelly, S. E. in *Comprehensive Organic Synthesis*, Trost, B. M. and Fleming, I. Ed.; Pergamon: Oxford, 1991, Vol. 1, pp. 729-817.
Kolodiazhnyi, O. T., *Phosphorus Ylides, Chemistry and Application in Organic Synthesis*; Wiley-VCH: New York, 1999.

Another carbon-carbon bond forming reaction that may be used to install the lower chain is the Peterson olefination reaction, which is reviewed by Ager, D. J. *Organic Reactions*, 1990, 38, 1-223.

Aldehydes that may be used in the olefination step involved in preparation of compounds of the present invention include, but are not limited to, intermediates 6a-f, which can be generally prepared from (R)-(+)-5-oxopyrrolidine-2-carboxylic acid (D-pyroglutamic acid) as shown in Scheme 2.

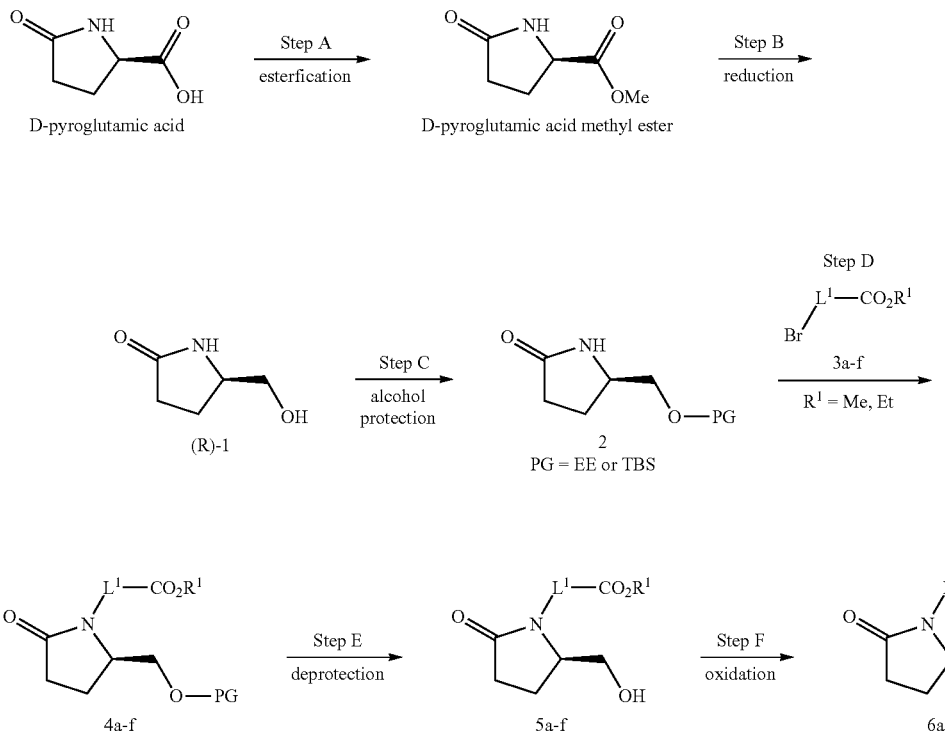

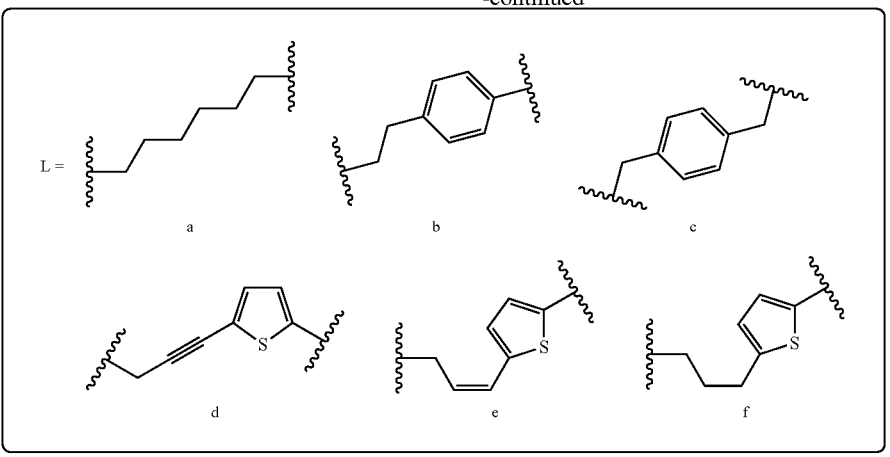

D-pyroglutamic acid may be esterified (Step A) and subsequently reduced (Step B) by known methods, including those described herein, to provide the resulting alcohol intermediate (R)-1. The hydroxyl moiety of intermediate (R)-1 may be protected (Step C) by reacting with ethyl vinyl ether (EVE) in the presence of TFA or tert-butyldimethylsilyl chloride (TBDMSCl or TBSCl) in the presence of a base, such as imidazole, to provide the EE-protected or TBS-protected species (2), respectively. N-alkylation of one of the protected pyrrolidone intermediates (2) with an alkylating agent, such as one of 3a-f, affords the corresponding intermediate 4a-f (Step D). Alcohol deprotection (Step E) and subsequent controlled alcohol oxidation (Step F) provides the corresponding aldehyde intermediates 6a-f that may be employed in the subsequent olefination step.

The aldehydes 6a-f may also be prepared from commercially available (R)-di-tert-butyl 2-aminopentanedioate 7 according to the route illustrated in Scheme 3. Condensation of 7 with bromides 3a-f provides 8a-f, respectively (Step A). Subsequent ring closure provides pyrrolidinone intermediates 9a-f (Step B). Removal of the tert-butyl group with TFA (Step C) unmasks the carboxylic acid moiety of intermediates 10a-f. Mixed anhydride formation by reacting these carboxylic acids with isobutyl chloroformate and subsequent reduction of the mixed anhydride with sodium borohydride (Step D) provides alcohol intermediates 5a-f. Controlled oxidation of the alcohol group of each of the compounds 5a-f provides aldehydes 6a-f as illustrated in Scheme 2, Step F.

Scheme 3

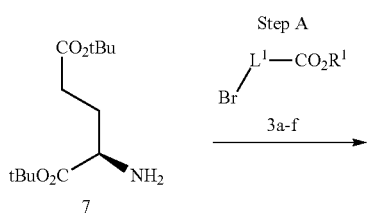

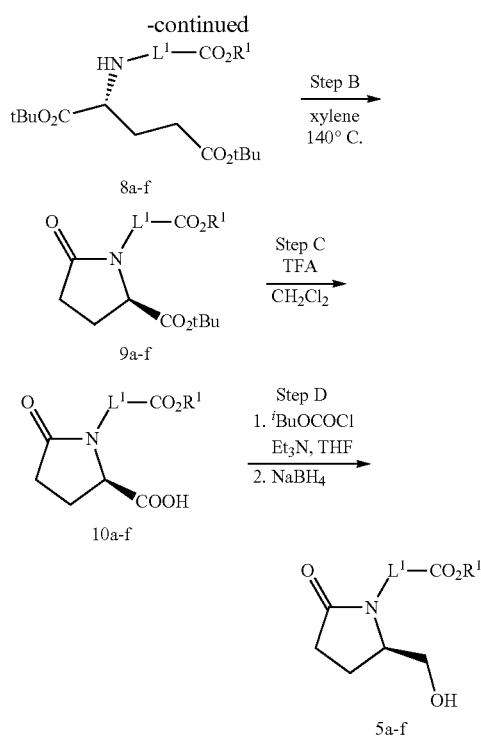

The aldehyde (R)-methyl 4-(2-(2-formyl-5-oxopyrrolidin-1-yl)ethyl)benzoate (6b) may be prepared from commercially available (R)-di-tert-butyl 2-aminopentanedioate (7) and aldehyde 11 where the key reductive alkylation step is shown below in Scheme 4. Condensation of 7 with methyl 4-(2-oxoethyl)benzoate (11) accompanied with subsequent ring closure provides pyrrolidinone intermediate 9b (Step A and B). Deesterification of 9b, as shown generally in Scheme 3, Step C, followed by reduction (Scheme 3, Step D) and subsequent controlled oxidation as generally shown in Scheme 2, Step F produces aldehyde 6b.

43

Scheme 4

Step A

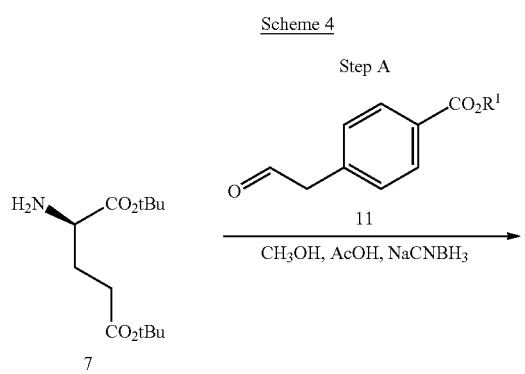

Step B
xylene, reflux

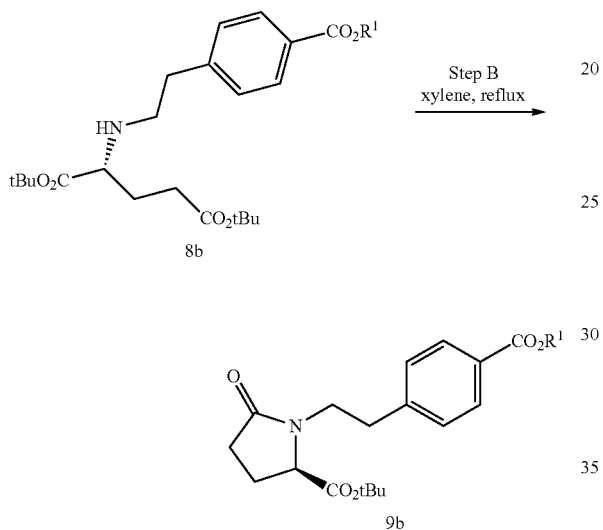

Aldehyde intermediate 6f may alternatively be acquired by the hydrogenation of protected alcohol intermediates 4d or 4e to 4f or the unprotected alcohol intermediates 5d or 5e to 5f, followed by the subsequent deprotection (for 4f) and controlled oxidation to 6f. One hydrogenation reaction example is illustrated in Scheme 5. Palladium-catalyzed reduction of the internal carbon-carbon double bond of intermediate 5e (Scheme 3) to provide alcohol intermediate 5f followed by the controlled oxidation of the alcohol affords aldehyde intermediate 6f as illustrated in Scheme 2, Step F.

Scheme 5

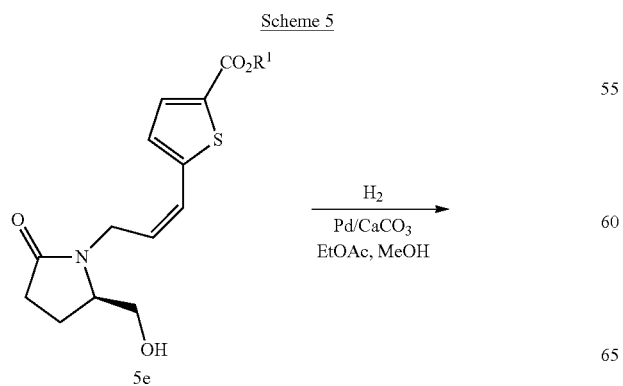

44

-continued

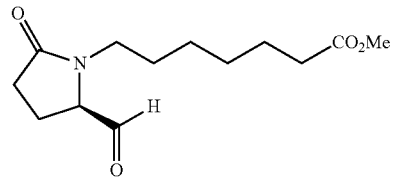 [SMILES: COC(=O)CCCCCCN1C(=O)CC[C@@H]1C=O]

Detailed procedures for preparing the aldehyde intermediates is described below.

Preparation of (R)-methyl 7-(3,3-difluoro-5-formyl-2-oxopyrrolidin-1-yl)heptanoate (6a)

Scheme 2. Step A: Preparation of (R)-methyl 5-oxopyrrolidine-2-carboxylate (D-pyroglutamic acid methyl ester) from (R)-5-oxopyrrolidine-2-carboxylic acid (D-pyroglutamic acid)

To a solution consisting of (R)-5-oxopyrrolidine-2-carboxylic acid (D-pyroglutamic acid from Chem-Impex International, 12.6 g, 97.4 mmol) in methanol (100 mL) was added sulfuric acid (1 mL) and the mixture was stirred at room temperature for 24 hours. The solvent was evaporated from the mixture, and the residue was purified by silica gel chromatography. Elution with acetone-dichloromethane (3:7 v/v) afforded the title intermediate (13.3 g, 95%) as a clear oil; TLC $R_f$ 0.42 (solvent system: 3:7 v/v acetone-dichloromethane); $^1$H-NMR (CDCl$_3$) δ 4.25 (t, 1H), 3.73 (s, 3H), 2.5-2.2 (m, 4H).

Scheme 2, Step B: Preparation of (R)-5-(hydroxymethyl)pyrrolidin-2-one ((R)-1)

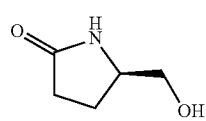

To a solution consisting of (R)-methyl 5-oxopyrrolidine-2-carboxylate (D-pyroglutamic acid methyl ester, 13.2 g, 115 mmol) in methanol (100 mL) at 0° C. was added sodium borohydride (10.5 g, 278 mmol) in portions. The reaction mixture was stirred at 0° C. until completion, at which time, acetic acid (3 mL) was added. The reaction mixture was concentrated and the residue was purified on silica gel, eluting with methanol-chloroform (1:9 v/v) to afford the title intermediate (12.9 g, 97%) as a colorless solid; TLC $R_f$ 0.33 (solvent system: 1:9 v/v methanol-chloroform); $^1$H-NMR (CDCl$_3$) δ 7.17 (s, 1H), 3.92 (s, 1H), 3.85-3.75 (m, 1H), 3.64-3.40 (m, 2H), 2.42-2.35 (m, 2H), 2.2-2.05 (m, 1H), 1.88-1.7 (m, 1H).

Scheme 2. Step C: Preparation of (5R)-5-((1-ethoxyethoxy)methyl)pyrrolidin-2-one (2/EE)

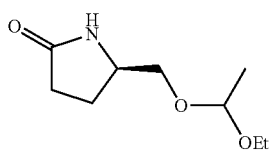

To a solution consisting of (R)-5-(hydroxymethyl)pyrrolidin-2-one (intermediate (R)-1, 21.7 g, 188 mmol) in dichloromethane (250 mL) was added ethyl vinyl ether (36.2 mL, 376 mmol) followed by trichloroacetic acid (0.878 g 5.37 mmol). The reaction mixture was stirred at room temperature for 16 hours. To the reaction mixture was added a saturated solution of sodium bicarbonate (400 mL) and the organic phase was separated. The organic phase was subsequently washed with water (200 mL) and brine (200 mL), dried over anhydrous sodium sulfate, filtered, and concentrated. The residue was purified by silica gel chromatography eluting with methanol-chloroform (1:9 v/v) to afford the title intermediate (13.0 g, 37%) as a clear oil; TLC $R_f$ 0.56 (solvent system: 1:9 v/v methanol-chloroform); $^1$H-NMR (CDCl$_3$) δ 4.69 (quartet, 1H), 3.83-3.2 (m, 5H), 2.35 (t, 2H), 2.25-2.19 (m, 1H), 1.8-1.7 (m, 1H), 1.38 (d, 3H), 1.21 (t, 3H).

Scheme 2, Step C: Preparation of (R)-5-(((tert-butyldimethylsilyl)oxy)methyl)-pyrrolidin-2-one (2/TBS)

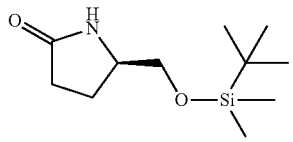

To a solution consisting of (R)-5-(hydroxymethyl)pyrrolidin-2-one (intermediate (R)-1, 5.7 g, 50 mmol) in dimethylsulfoxide (50 mL) was added tert-butyldimethylchlorosilane (9.71 g, 64.5 mmol) followed by imidazole (4.39 g, 64.5 mmol). The reaction mixture was stirred at room temperature overnight. The reaction mixture was quenched with water (50 mL) and extracted with ethyl acetate (3×100 mL). The combined organic phase was dried over anhydrous sodium sulfate, filtered, and concentrated. The residue was purified by silica gel chromatography eluting with methanol-chloroform (5:95 v/v) to afford the title intermediate (10.0 g, 85%) as a clear oil; TLC $R_f$ 0.37 (solvent system: 5:95 v/v methanol-chloroform).

Scheme 2, Step D: Preparation of methyl 7-((2R)-2-((1-ethoxyethoxy)methyl)-5-oxopyrrolidin-1-yl)heptanoate (4a)

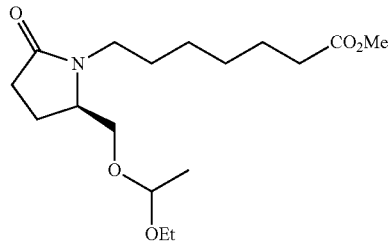 [SMILES: CCOC(C)OC[C@H]1CCC(=O)N1CCCCCCC(=O)OC]

To an ice-chilled suspension consisting of sodium hydride (60% in mineral oil, 1.07 g, 26.7 mmol) and sodium iodide (4.40 g, 29.4 mmol) in hexamethylphosphoramide (30 mL) was added dropwise a solution consisting of (5R)-5-((1-ethoxyethoxy)methyl)-pyrrolidin-2-one (intermediate 2/EE, 5.00 g, 26.7 mmol) in hexamethylphosphoramide (20 mL). The mixture was stirred at room temperature for two hours followed by 50° C. for 20 minutes. To the reaction mixture was added dropwise methyl 7-bromoheptanoate (commercially available from Alfa Aesar, 7.15 g, 32.0 mmol) and stirred overnight at 50° C. The mixture was diluted with ethyl acetate (300 mL). Concentrated aqueous hydrochloric acid (10 mL) was subsequently added followed by water (50 mL). The aqueous phase was separated and the organic layer was washed with 5% aqueous sodium thiosulfate (100 mL), water (200 mL), and brine (300 mL), and was dried over anhydrous sodium sulfate, filtered and evaporated to provide the crude title intermediate, which was carried on to the next step without further purification or characterization.

Scheme 2. Step E: Preparation of (R)-methyl 7-(2-(hydroxymethyl)-5-oxopyrrolidin-1-yl)heptanoate (5a)

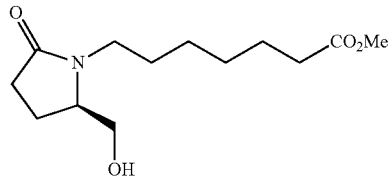 [SMILES: COC(=O)CCCCCCN1C(=O)CC[C@@H]1CO]

To a solution consisting of the crude methyl 7-((2R)-2-((1-ethoxyethoxy)methyl)-5-oxopyrrolidin-1-yl)heptanoate (4a) in methanol (50 mL) was added p-toluenesulfonic acid monohydrate (10 mg) and the mixture was stirred at room temperature for 18 hours. To the reaction mixture was added a saturated aqueous solution of sodium bicarbonate and the organic material was extracted with ethyl acetate. The organic phase was separated and washed with brine, dried over anhydrous sodium sulfate, filtered, and concentrated. The residue was purified by silica gel chromatography eluting with methanol-ethyl acetate (3:97 v/v) to afford the title intermediate (1.24 g, 18% over two steps) as a pale yellow oil; TLC $R_f$ 0.24 (solvent system: 3:97 v/v methanol-ethyl acetate); MS (APCI$^+$) m/z 258 (M+1).

Scheme 2. Step F: Preparation of (R)-methyl 7-(2-formyl-5-oxopyrrolidin-1-yl)heptanoate (6a)

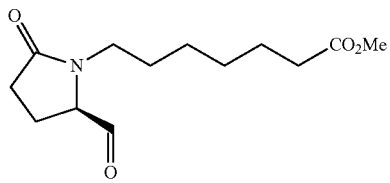 [SMILES: COC(=O)CCCCCCN1C(=O)CC[C@@H]1C=O]

To a solution consisting of (R)-methyl 7-(2-(hydroxymethyl)-5-oxopyrrolidin-1-yl)heptanoate (intermediate 5a, 1.24 g, 4.82 mmol) in dichloromethane (25 mL) was added Dess-Martin periodinane (2.04 g, 4.82 mmol) in portions and the mixture was stirred at room temperature until completion as monitored by TLC. The volatiles were evaporated, and to the residual mixture was added diethyl ether (50 mL). The solid material was filtered through a thin pad of Celite and the filtrate was concentrated. The residue was purified on silica gel eluting with methanol-ethyl acetate (3:97 v/v) to afford the title intermediate (1.1 g, 89%) as a pale yellow oil; TLC $R_f$ 0.33 (solvent system: 3:97 v/v methanol-ethyl acetate).

Preparation of (R)-methyl 4-(2-(2-formyl-5-oxopyrrolidin-1-yl)ethyl)benzoate (6b)

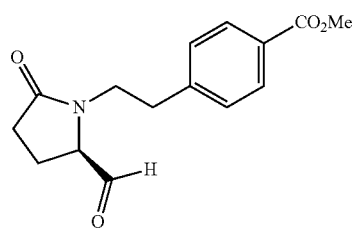 [SMILES: COC(=O)c1ccc(CCN2C(=O)CC[C@@H]2C=O)cc1]

Scheme 4. Steps A and B: Preparation of (R)-tert-butyl 1-(4-(methoxycarbonyl)-phenethyl)-5-oxopyrrolidine-2-carboxylate (9b)

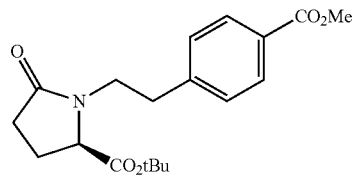 [SMILES: COC(=O)c1ccc(CCN2C(=O)CC[C@@H]2C(=O)OC(C)(C)C)cc1]

Step A

To a solution consisting of (R)-di-tert-butyl 2-aminopentanedioate (reagent 7, H-D-Glu(OtBu)-OtBu, commercially available from Life ProTein (3.50 g, 15.6 mmol) in methanol (100 mL) was added methyl 4-(2-oxoethyl)benzoate (synonym: 4-carbomethoxyphenylacetaldehyde, reagent 11; obtained from methyl 4-formyl benzoate as described in Nair et al., *J. Med. Chem.*, 1989, 32, 1277-1283; 2.80 g, 15.6 mmol), acetic acid (1.05 mL, 2.67 mmol), and sodium cyanoborohydride (1.45 g, 23.1 mmol), and the mixture was stirred at room temperature for three hours. The reaction mixture was diluted with ethyl acetate and washed with water and brine, dried over sodium sulfate, filtered, and concentrated under reduced pressure.

Step B

The residue (crude intermediate 8b) was diluted with xylene and the solution refluxed for 5 hours and concentrated. The residue was purified by silica gel chromatography eluting with ethyl acetate-heptane (1:1) to afford the title compound (2.0 g, 37%) as a white solid; TLC $R_f$ 0.45 (solvent system 1:1 v/v ethyl acetate-heptane).

Scheme 3, Step C: Preparation of (R)-1-(4-(methoxycarbonyl)phenethyl)-5-oxopyrrolidine-2-carboxylic acid (10b)

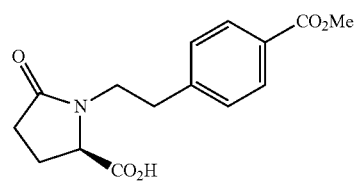 [SMILES: COC(=O)c1ccc(CCN2C(=O)CC[C@@H]2C(=O)O)cc1]

A mixture consisting of (R)-tert-butyl 1-(4-(methoxycarbonyl)phenethyl)-5-oxopyrrolidine-2-carboxylate (intermediate 9b, 2.0 g, 5.7 mmol), trifluoroacetic acid (25 mL), and water (0.125 mL) was stirred for three hours at room temperature and was subsequently concentrated in vacuo to afford the crude title intermediate (2.26 g) as a yellow oil, which was used in the next step without purification.

Scheme 3, Step D: Preparation of (R)-methyl 4-(2-(2-(hydroxymethyl)-5-oxopyrrolidin-1-yl)ethyl)benzoate (5b)

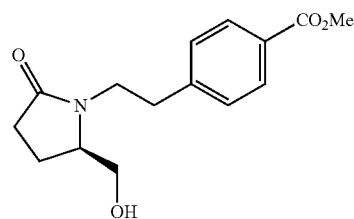 [SMILES: COC(=O)c1ccc(CCN2C(=O)CC[C@@H]2CO)cc1]

To a stirring mixture consisting of crude (R)-1-(4-(methoxycarbonyl)phenethyl)-5-oxopyrrolidine-2-carboxylic acid (intermediate 10b, 2.26 g, 8.14 mmol) in THF (40 mL) at −10° C. was added N-methylmorpholine (0.9 mL, 8 mmol). After stirring for five minutes, isobutyl chloroformate (1.08 mL, 8.25 mmol) was added dropwise and the reaction mixture was stirred for an additional thirty minutes and was subsequently filtered through a pad of Celite. The filtrate was cooled to −10° C., and a solution consisting of sodium borohydride (0.434 g, 11.5 mmol) predissolved in water (15 mL) was added. The resulting mixture was stirred at 0° C. for one hour and then at room temperature for one hour. The mixture was poured into a separatory funnel and diluted with ethyl acetate (200 mL). The organic layer was washed sequentially with 1N hydrochloric acid solution, saturated sodium bicarbonate solution, and brine, was dried over sodium sulfate, filtered, and concentrated. The residue was purified by silica gel chromatography eluting with methanol-ethyl acetate (3:97 v/v) to afford the title compound as an off white solid; TLC $R_f$ 0.19 (solvent system 3:97 v/v methanol-ethyl acetate); MS (APCI$^+$) m/z 278 (M+1).

Scheme 2, Step F: Preparation of (R)-methyl 4-(2-(2-formyl-5-oxopyrrolidin-1-yl)ethyl)benzoate (6b)

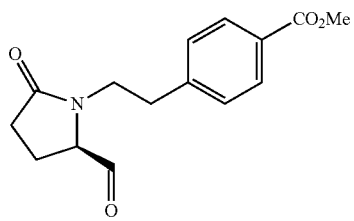 [SMILES: COC(=O)c1ccc(CCN2C(=O)CC[C@@H]2C=O)cc1]

(R)-Methyl 4-(2-(2-formyl-5-oxopyrrolidin-1-yl)ethyl) benzoate (0.246 g, 62.5%, a colorless oil) was prepared by the method described in Scheme 2, Step F for the preparation of aldehyde intermediate 6a except that (R)-methyl 4-(2-(2-(hydroxymethyl)-5-oxopyrrolidin-1-yl)ethyl)benzoate (5b) was used instead of (R)-methyl 7-(2-(hydroxymethyl)-5-oxopyrrolidin-1-yl)heptanoate; TLC $R_f$ 0.29 (solvent system 3:97 v/v methanol-ethyl acetate).

Preparation of (R)-methyl 2-(4-((2-formyl-5-oxopyrrolidin-1-yl)methyl)phenyl)-acetate (6c)

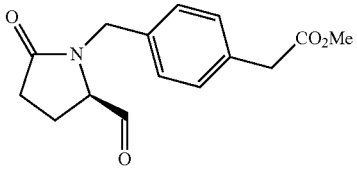 [SMILES: COC(=O)Cc1ccc(CN2C(=O)CC[C@@H]2C=O)cc1]

Scheme 3. Step A: Preparation of (R)-di-tert-butyl 2-((4-(2-methoxy-2-oxoethyl)benzyl)amino)pentanedioate (8c)

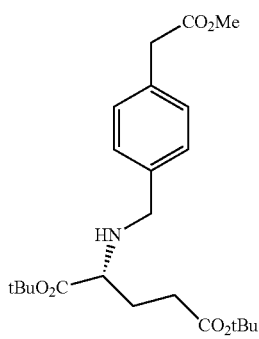 [SMILES: COC(=O)Cc1ccc(CN[C@H](CCC(=O)OC(C)(C)C)C(=O)OC(C)(C)C)cc1]

A stirring mixture consisting of (R)-di-tert-butyl 2-aminopentanedioate (reagent 7, H-D-Glu(OtBu)-OtBu, 5.0 g, 16.9 mmol), methyl 2-(4-(bromomethyl)phenyl)acetate (reagent 3c, 4.52 g, 18.6 mmol; prepared in 99% yield from the corresponding carboxylic acid and trimethylsilyldiazomethane according to known methods such as those described in Leggio, A. et al., *Chemical Biology & Drug Design*, 2009, 73(3), 287-291), diisopropylethylamine (8.83 mL, 50.7 mmol), and sodium iodide (2.53 g, 16.9 mmol) in dry hexamethylphosphoramide (50 mL) was heated at 55° C. for 15 hours. The reaction mixture was cooled, diluted with ethyl acetate (1.5 L), and washed sequentially with an aqueous solution of ammonium chloride and a saturated aqueous solution of sodium chloride. The organic phase was dried over sodium sulfate and concentrated in vacuo. The residue was purified by silica gel chromatography eluting with a gradient of ethyl acetate-heptane (1:20 to 1:5 v/v) to afford the title intermediate (5.78 g, 81%) as a colorless oil; TLC $R_f$ 0.45 (solvent system 1:3 v/v ethyl acetate-heptane); MS (APCI$^+$) m/z 422 (M+1).

Scheme 3. Step B: Preparation of (R)-tert-butyl 1-(4-(2-methoxy-2-oxoethyl)benzyl)-5-oxopyrrolidine-2-carboxylate (9c)

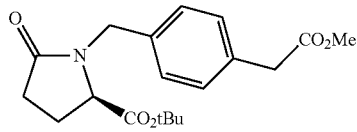 [SMILES: COC(=O)Cc1ccc(CN2C(=O)CC[C@@H]2C(=O)OC(C)(C)C)cc1]

A stirring mixture consisting of (R)-di-tert-butyl 2-((4-(2-methoxy-2-oxoethyl)benzyl)amino)pentanedioate (intermediate 8c, 5.75 g, 13.6 mmol) in o-xylene (40 mL) was heated at 100° C. for three days. The solvent was evaporated under reduced pressure and the residue was purified by silica gel chromatography eluting with a gradient of ethyl acetate-heptane (1:20 to 1:1 v/v) to afford the title intermediate (3.09 g, 65.2%) as a colorless oil; TLC $R_f$ 0.6 (solvent system 4:6 v/v ethyl acetate-heptane); MS (APCI$^+$) m/z 370 (M+23, Na$^+$).

Scheme 3. Step C: Preparation of (R)-1-(4-(2-methoxy-2-oxoethyl)benzyl)-5-oxopyrrolidine-2-carboxylic acid (10c)

A stirring mixture consisting of (R)-tert-butyl 1-(4-(2-methoxy-2-oxoethyl)benzyl)-5-oxopyrrolidine-2-carboxylate (intermediate 9c, 2.93 g, 8.43 mmol) and trifluoroacetic acid (4.55 mL, 59.0 mmol) in dichloromethane (30 mL) was heated at 45° C. for seven hours with subsequent stirring at room temperature overnight. The reaction mixture was diluted with ethanol and evaporated under reduced pressure. The crude residue (2.44 g) was carried onto the next step (Step D) without purification.

Scheme 3. Step D: Preparation of (R)-methyl 2-(4-((2-(hydroxymethyl)-5-oxopyrrolidin-1-yl)methyl) phenyl)acetate (5c)

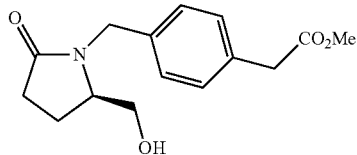 [SMILES: COC(=O)Cc1ccc(CN2C(=O)CC[C@@H]2CO)cc1]

(R)-Methyl 2-(4-((2-(hydroxymethyl)-5-oxopyrrolidin-1-yl)methyl)phenyl)acetate (1.6 g, 65%, as a colorless oil) was prepared in the same manner as compound 5b in Scheme 3, Step D except that (R)-1-(4-(2-methoxy-2-oxoethyl)benzyl)-5-oxopyrrolidine-2-carboxylic acid (10c) was used instead of (R)-1-(4-(methoxycarbonyl)phenethyl)-5-oxopyrrolidine-2-carboxylic acid; TLC $R_f$ 0.5 (solvent system 5:95 v/v methanol-dichloromethane); $^1$H-NMR (CDCl$_3$) δ 7.3-7.2 (m, 4H), 4.9 (d, 1H), 4.2 (d, 1H), 3.8-3.7 (m, 1H), 3.7 (s, 3H), 3.6 (s, 2H), 3.6-3.4 (m, 2H), 2.6-2.4 (m, 2H), 2.1-1.9 (m, 2H).

Scheme 2. Step F: Preparation of (R)-methyl 2-(4-((2-formyl-5-oxopyrrolidin-1-yl)methyl)phenyl)acetate (6c)

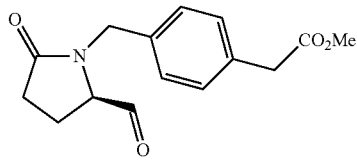 [SMILES: COC(=O)Cc1ccc(CN2C(=O)CC[C@@H]2C=O)cc1]

(R)-Methyl 2-(4-((2-formyl-5-oxopyrrolidin-1-yl) methyl)phenyl)acetate (0.2 g, 90%) was prepared in the same manner as compound 6a in Scheme 2, Step F except that (R)-methyl 2-(4-((2-(hydroxymethyl)-5-oxopyrrolidin-1-yl)methyl)phenyl)acetate (5c) was used instead of (R)-methyl 7-(2-(hydroxymethyl)-5-oxopyrrolidin-1-yl)heptanoate; MS (ESI$^-$) m/z 274 (M−1); $^1$H-NMR (CDCl$_3$) δ 9.4 (d, 1H), 7.3-7.1 (m, 4H), 5.0-4.8 (m, 2H), 4.2-4.0 (m, 1H), 3.7 (s, 3H), 3.6 (s, 2H), 2.6-1.9 (m, 4H).

Preparation of (R)-methyl 5-((2-(hydroxymethyl)-5-oxopyrrolidin-1-yl)ethynyl)thiophene-2-carboxylate (6d)

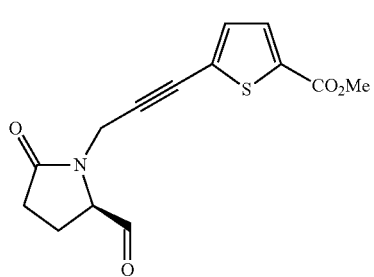 [SMILES: COC(=O)c1ccc(C#CCN2C(=O)CC[C@@H]2C=O)s1]

Step 1: Preparation of methyl 5-bromo-2-thiophene carboxylate

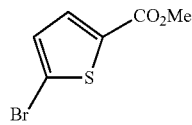

To an ice-cooled mixture consisting of 5-bromo-2-thiophene carboxylic acid (5.25 g, 25.4 mmol) in ethyl acetate (200 mL) and methanol (20 mL) was added trimethylsilyldiazomethane (2M in diethyl ether, 20 mL, 40 mmol) over 20 minutes. The reaction mixture was stirred for 24 hours. The solvent was removed and the residue was purified by silica gel chromatography eluting with ethyl acetate-heptanes (1:50 v/v) to afford the title intermediate (5.5 g, 98%) as a white solid; TLC $R_f$ 0.60 (solvent system 1:9 v/v ethyl acetate-heptanes); $^1$H-NMR (CDCl$_3$) δ 7.5 (d, 1H), 7.1 (d, 1H), 4.9 (s, 3H).

Step 2: Preparation of 5-(3-hydroxyprop-1-yn-1-yl)thiophene-2-carboxylate

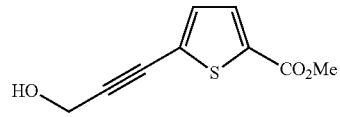 [SMILES: COC(=O)c1ccc(C#CCO)s1]

To a covered mixture consisting of methyl 5-bromo-2-thiophene carboxylate (5.6 g, 25 mmol) in benzene (60 mL) was added a suspension consisting of tetrakis(triphenylphosphine)palladium (0) (1.4 g, 1.3 mmol) in benzene (10 mL), and the reaction mixture was stirred for 30 minutes. To the reaction mixture was then added copper(I) iodide (480 mg, 2.52 mmol) and n-butylamine (5 mL, 50 mmol) in one portion each, followed by propargyl alcohol (2.2 mL, 38 mmol) in benzene (30 mL) over 15 minutes, and the reaction was stirred for 24 hours. To the reaction mixture was added a saturated solution of ammonium chloride (200 mL) and the organic material was extracted with ethyl acetate. The organic phase was washed with water, then brine, dried over sodium sulfate, filtered, and concentrated. The residue was purified by silica gel chromatography eluting with ethyl acetate-heptanes (1:10 v/v) to afford the title intermediate (3.8 g, 78%); TLC $R_f$ 0.7 (solvent system 1:1 v/v ethyl acetate-heptanes); $^1$H-NMR (CDCl$_3$) δ 7.6 (d, 1H), 7.1 (d, 1H), 4.5 (s, 2H), 3.9 (s, 3H), 2.0 (br s, 1H).

Step 3: Preparation of methyl 5-(3-bromoprop-1-yn-1-yl)thiophene-2-carboxylate (3d)

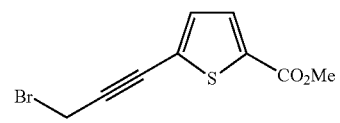 [SMILES: COC(=O)c1ccc(C#CCBr)s1]

To an ice cooled solution of 5-(3-hydroxyprop-1-yn-1-yl) thiophene-2-carboxylate (1.32 g, 6.73 mmol) in dichloromethane (25 ml) was added carbon tetrabromide (3.1 g, 9.42 mmol) and triphenylphosphine (2.5 g, 9.42 mmol) and the mixture stirred for 4 hours. The solvent was removed and the residue was purified by silica gel chromatography eluting with ethyl acetate:heptanes (1:25 v:v) to afford the title compound (1.5 g). TLC $R_f$ 0.65 (solvent system 80:20 v/v heptanes:ethyl acetate); $^1$H-NMR (CDCl$_3$) δ 7.6 (d, 1H), 7.1 (d, 1H), 4.1 (s, 2H), 3.9 (s, 3H).

Scheme 3. Step A: Preparation of (R)-di-tert-butyl 2-((3-(5-(methoxycarbonyl)-thiophen-2-yl)prop-2-yn-1-yl)amino)pentanedioate (8d)

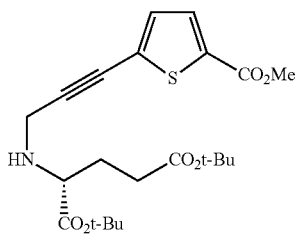 [SMILES: COC(=O)c1ccc(C#CCN[C@H](CCC(=O)OC(C)(C)C)C(=O)OC(C)(C)C)s1]

(R)-Di-tert-butyl 2-((3-(5-(methoxycarbonyl)thiophen-2-yl)prop-2-yn-1-yl)amino)pentanedioate was prepared in the same manner as compound 8c in Scheme 3, Step A except that methyl 5-(3-bromoprop-1-yn-1-yl)thiophene-2-carboxylate (3d) was used instead of methyl 2-(4-(bromomethyl)phenyl)acetate; TLC $R_f$ 0.45 (solvent system 80:20 v/v heptanes:ethyl acetate); $^1$H-NMR (CDCl$_3$) δ 7.7 (d, 1H), 6.9 (d, 1H), 3.9 (s, 3H), 3.3-3.2 (m, 1H), 3.2 (s, 2H), 2.4 (t, 2H), 2.0-1.8 (m, 2H), 1.45 (d, 18H).

Scheme 3. Step B: Preparation of (R)-tert-butyl 1-(3-(5-(methoxycarbonyl)-thiophen-2-yl)prop-2-yn-1-yl)-5-oxopyrrolidine-2-carboxylate (9d)

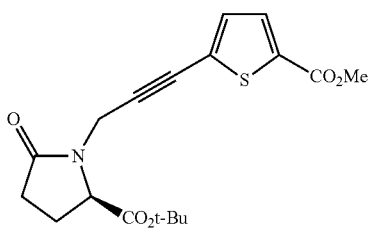 [SMILES: COC(=O)c1ccc(C#CCN2C(=O)CC[C@@H]2C(=O)OC(C)(C)C)s1]

(R)-Tert-butyl 1-(3-(5-(methoxycarbonyl)thiophen-2-yl) prop-2-yn-1-yl)-5-oxopyrrolidine-2-carboxylate was prepared in the same manner as compound 9c in Scheme 3, Step B except that (R)-di-tert-butyl 2-((3-(5-(methoxycarbonyl) thiophen-2-yl)prop-2-yn-1-yl)amino)pentanedioate (8d) was used instead of (R)-di-tert-butyl 2-((4-(2-methoxy-2-oxoethyl)benzyl)amino)pentanedioate; TLC $R_f$ 0.25 (solvent system 60:40 v/v heptanes:ethyl acetate); $^1$H-NMR (CDCl$_3$) δ 7.7 (d, 1H), 6.9 (d, 1H), 4.5-4.4 (m, 1H), 4.2-4.0 (m, 2H), 3.85 (s, 3H), 2.6-2.5 (m, 1H), 2.4-2.2 (m, 2H), 2.1-2.0 (m, 1H), 1.4 (s, 9H).

Scheme 3, Step C: Preparation of (R)-1-(3-(5-(methoxycarbonyl)thiophen-2-yl)prop-2-yn-1-yl)-5-oxopyrrolidine-2-carboxylic acid (10d)

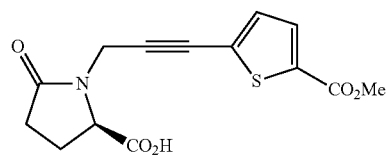 [SMILES: COC(=O)c1ccc(C#CCN2C(=O)CC[C@@H]2C(=O)O)s1]

A solution of (R)-tert-butyl 1-(3-(5-(methoxycarbonyl) thiophen-2-yl)prop-2-yn-1-yl)-5-oxopyrrolidine-2-carboxylate (1.1 g, 3.03 mmol) and trifluoroacetic acid (4 mL, 51.9 mmol) in dichloromethane (45 mL) was heated at 50° C. overnight. The reaction mixture was diluted with ethanol and toluene and evaporated under reduced pressure to produce a residue that was used in the next step (Step D) with no further purification; TLC $R_f$ 0.10 (solvent system 60:40 v/v heptanes:ethyl acetate).

Scheme 3. Step D: Preparation of (R)-methyl 5-(3-(2-(hydroxymethyl)-5-oxopyrrolidin-1-yl)prop-1-yn-1-yl)thiophene-2-carboxylate (5d)

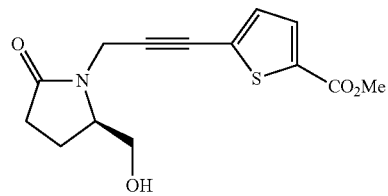 [SMILES: COC(=O)c1ccc(C#CCN2C(=O)CC[C@@H]2CO)s1]

(R)-Methyl 5-(3-(2-(hydroxymethyl)-5-oxopyrrolidin-1-yl)prop-1-yn-1-yl)thiophene-2-carboxylate was prepared in the same manner as compound 5b in Scheme 3, Step D except that (R)-1-(3-(5-(methoxycarbonyl)thiophen-2-yl) prop-2-yn-1-yl)-5-oxopyrrolidine-2-carboxylic acid (10d) was used instead of (R)-1-(4-(methoxycarbonyl)phenethyl)-5-oxopyrrolidine-2-carboxylic acid and triethylamine was used instead of N-methylmorpholine; TLC $R_f$ 0.30 (solvent system 95:5 v/v dichloromethane:methanol); $^1$H-NMR (CDCl$_3$); δ 7.6 (d, 1H), 6.9 (d, 1H), 4.1-4.0 (m, 1H), 3.85 (s, 3H), 3.8 (s, 2H) 3.6-3.5 (s, 1H), 3.2-3.0 (br s, 1H), 2.6-2.4 (m, 1H), 2.4-2.3 (m, 1H), 2.2-2.0 (m, 1H), 2.0-1.9 (m, 1H); MS (ESI$^+$) m/z 294.0 (M+1), (ESI$^-$) m/z 292.0 (M−1).

Scheme 2, Step F: Preparation of (R)-methyl 5-(3-(2-formyl-5-oxopyrrolidin-1-yl)prop-1-yn-1-yl)thiophene-2-carboxylate (6d)

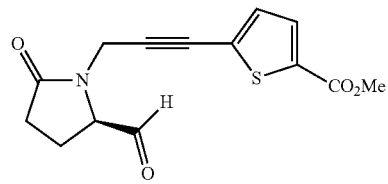 [SMILES: COC(=O)c1ccc(C#CCN2C(=O)CC[C@@H]2C=O)s1]

(R)-Methyl 5-(3-(2-formyl-5-oxopyrrolidin-1-yl)prop-1-yn-1-yl)thiophene-2-carboxylate was prepared in the same manner as compound 6a in Scheme 2, Step F except that (R)-methyl 5-(3-(2-(hydroxymethyl)-5-oxopyrrolidin-1-yl)prop-1-yn-1-yl)thiophene-2-carboxylate (7d) was used instead of (R)-methyl 7-(2-(hydroxymethyl)-5-oxopyrrolidin-1-yl)heptanoate; TLC R$_f$ 0.30 (solvent system 95:5 v/v dichloromethane:methanol).

Preparation of (R,Z)-methyl 5-(3-(2-formyl-5-oxopyrrolidin-1-yl)prop-1-en-1-yl)thiophene-2-carboxylate (6e)

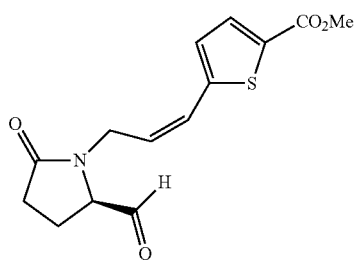 [SMILES: COC(=O)c1ccc(/C=C\CN2C(=O)CC[C@@H]2C=O)s1]

Step 1: Preparation of (Z)-methyl 5-(3-hydroxyprop-1-en-1-yl)thiophene-2-carboxylate

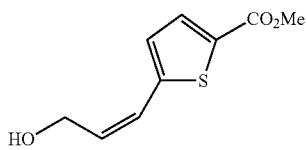 [SMILES: COC(=O)c1ccc(/C=C\CO)s1]

To a mixture consisting of methyl 5-(3-hydroxyprop-1-yn-1-yl)thiophene-2-carboxylate (1.9 g, 9.7 mmol) in ethyl acetate (50 mL) and methanol (5 mL) was added palladium on calcium carbonate (5%, 1.5 g). The reaction flask was evacuated and backfilled with hydrogen gas and the reaction mixture was subsequently stirred for 2 hours while maintaining a hydrogen atmosphere. The mixture was then filtered through Celite and the solvent removed. The residue was purified by silica gel chromatography eluting with ethyl acetate-heptanes (1:10 v/v) to afford the title intermediate (1.5 g); TLC R$_f$ 0.65 (solvent system 1:1 v/v ethyl acetate-heptanes); MS (ESI$^+$) m/z 221 (M+Na$^+$); $^1$H-NMR (CDCl$_3$) δ 7.7 (d, 1H), 6.9 (d, 1H), 6.6 (d, 1H), 6.0-5.9 (m, 1H), 4.6 (d, 2H), 3.9 (s, 3H), 1.9 (br s, 1H).

Step 2: Preparation of (Z)-methyl 5-(3-bromoprop-1-en-1-yl)thiophene-2-carboxylate (3e)

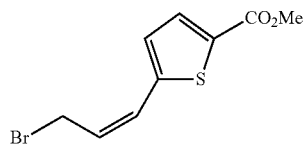 [SMILES: COC(=O)c1ccc(/C=C\CBr)s1]

(Z)-Methyl 5-(3-bromoprop-1-en-1-yl)thiophene-2-carboxylate (2.56 g) was prepared in the same manner as compound 3d except that (Z)-methyl 5-(3-hydroxyprop-1-en-1-yl)thiophene-2-carboxylate was used instead of 5-(3-hydroxyprop-1-yn-1-yl)thiophene-2-carboxylate; TLC R$_f$ 0.60 (solvent system 20:80 v/v ethyl acetate-heptanes); MS (ESI$^+$) m/z 261, 263 (isotopic bromines, each is (M+H+)); $^1$H-NMR (CDCl$_3$) δ 7.7 (d, 1H), 7.2 (d, 1H), 6.6 (d, 1H), 6.2-6.0 (m, 1H), 4.3 (d, 2H), 3.9 (s, 3H).

Scheme 3. Step A: Preparation of (R,Z)-di-tert-butyl 2-((3-(5-(methoxycarbonyl)-thiophen-2-yl)allyl)amino)pentanedioate (8e)

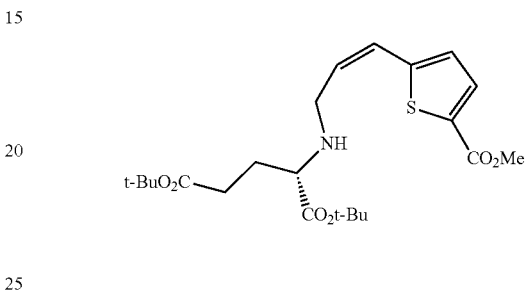

(R,Z)-Di-tert-butyl 2-((3-(5-(methoxycarbonyl)thiophen-2-yl)allyl)amino)-pentanedioate was prepared in the same manner as compound 8c in Scheme 3, Step A, except that (Z)-methyl 5-(3-bromoprop-1-en-1-yl)thiophene-2-carboxylate (3e) was used instead of methyl 2-(4-(bromomethyl)phenyl)acetate; TLC R$_f$ 0.30 (solvent system 1:4 v/v ethyl acetate-heptanes); MS (ESI') m/z 440 (M+1); $^1$H-NMR (CDCl$_3$) δ 7.7 (d, 1H), 6.9 (d, 1H), 6.6 (d, 1H), 5.9-5.8 (m, 1H), 3.9 (s, 3H), 3.7-3.5 (s, 2H), 3.3-3.2 (m, 1H), 2.4 (t, 2H), 2.0-1.8 (m, 2H), 1.5 (s, 9H), 1.4 (s, 9H).

Scheme 3. Step B: Preparation of (R,Z)-tert-butyl 1-(3-(5-(methoxycarbonyl)-thiophen-2-yl)allyl)-5-oxopyrrolidine-2-carboxylate (9e)

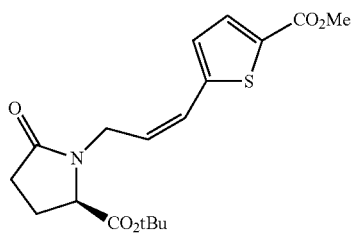 [SMILES: COC(=O)c1ccc(/C=C\CN2C(=O)CC[C@@H]2C(=O)OC(C)(C)C)s1]

(R,Z)-tert-Butyl 1-(3-(5-(methoxycarbonyl)thiophen-2-yl)allyl)-5-oxopyrrolidine-2-carboxylate was prepared in the same manner as compound 9c in Scheme 3, Step B except that (R,Z)-di-tert-butyl 2-((3-(5-(methoxycarbonyl)thiophen-2-yl)allyl)amino)pentanedioate (8e) was used instead of (R)-di-tert-butyl 2-((4-(2-methoxy-2-oxoethyl)benzyl)amino)-pentanedioate; TLC R$_f$ 0.20 (solvent system 2:3 v/v ethyl acetate-heptanes); MS (ESI$^+$) m/z 366 (M+1), 388 (M+Na$^+$); $^1$H-NMR (CDCl$_3$) δ 7.7 (d, 1H), 6.9 (d, 1H), 6.6 (d, 1H), 5.7-5.6 (m, 1H), 4.5-4.4 (m, 1H), 4.2-4.0 (m, 2H), 3.85 (s, 3H), 2.6-2.5 (m, 1H), 2.4-2.2 (m, 2H), 2.1-2.0 (m, 1H), 1.4 (s, 9H).

Scheme 3. Step C: Preparation of (R,Z)-1-(3-(5-(methoxycarbonyl)thiophen-2-yl)allyl)-5-oxopyrrolidine-2-carboxylic acid (10e)

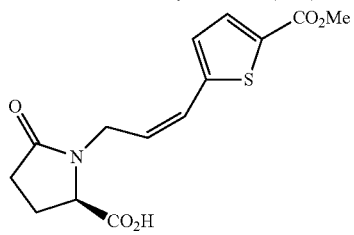

A stirring mixture consisting of (R,Z)-tert-butyl 1-(3-(5-(methoxycarbonyl)-thiophen-2-yl)allyl)-5-oxopyrrolidine-2-carboxylate (intermediate 9e, 2.05 g, 5.61 mmol) and trifluoroacetic acid (5.0 mL, 65 mmol) in dichloromethane (40 mL) was heated at 45° C. overnight. The reaction mixture was diluted with ethanol and evaporated under reduced pressure to provide a residue (2.44 g) that was used in the next step (Step D) without further purification; TLC $R_f$ 0.25 (solvent system 50:50:1 v/v ethyl acetate-heptanes-acetic acid).

Scheme 3, Step D: Preparation of (R,Z)-methyl 5-(3-(2-(hydroxymethyl)-5-oxopyrrolidin-1-yl)prop-1-en-1-yl)thiophene-2-carboxylate (5e)

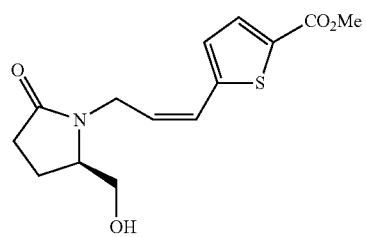 [SMILES: COC(=O)c1ccc(/C=C\CN2C(=O)CC[C@@H]2CO)s1]

(R,Z)-Methyl 5-(3-(2-(hydroxymethyl)-5-oxopyrrolidin-1-yl)prop-1-en-1-yl)thiophene-2-carboxylate was prepared in the same manner as compound 5b in Scheme 3, Step D except that (R,Z)-1-(3-(5-(methoxycarbonyl)thiophen-2-yl)allyl)-5-oxopyrrolidine-2-carboxylic acid (10e) was used instead of (R)-1-(4-(methoxycarbonyl)phenethyl)-5-oxopyrrolidine-2-carboxylic acid and triethylamine was used instead of N-methylmorpholine; TLC $R_f$ 0.20 (solvent system 50:50:1 v/v ethyl acetate-heptanes-acetic acid); MS (ESI$^+$) m/z 296 (M+1), 318 (M+Na$^+$); $^1$H-NMR (CDCl$_3$) δ 7.6 (d, 1H), 6.9 (d, 1H), 6.6 (d, 1H), 6.1-5.6 (m, 1H), 4.5-4.3 (m, 1H), 4.1-4.0 (m, 1H), 3.85 (s, 3H), 3.7 (s, 2H) 3.6-3.5 (m, 1H), 3.2-3.0 (br s, 1H), 2.6-2.4 (m, 1H), 2.4-2.3 (m, 1H), 2.2-2.0 (m, 1H), 2.0-1.9 (m, 1H).

Scheme 2, Step F: Preparation of (R,Z)-methyl 5-(3-(2-formyl-5-oxopyrrolidin-1-yl)prop-1-en-1-yl)thiophene-2-carboxylate (6e)

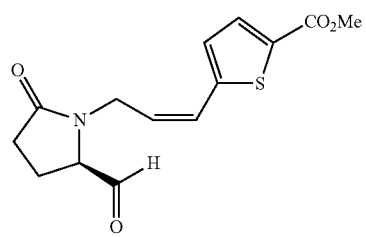 [SMILES: COC(=O)c1ccc(/C=C\CN2C(=O)CC[C@@H]2C=O)s1]

(R,Z)-Methyl 5-(3-(2-formyl-5-oxopyrrolidin-1-yl)prop-1-en-1-yl)thiophene-2-carboxylate was prepared in the same manner as compound 6a in Scheme 2, Step F except that (R,Z)-methyl 5-(3-(2-(hydroxymethyl)-5-oxopyrrolidin-1-yl)prop-1-en-1-yl)thiophene-2-carboxylate (5e) was used instead of (R)-methyl 7-(2-(hydroxymethyl)-5-oxopyrrolidin-1-yl)heptanoate; TLC $R_f$ 0.40 (solvent system 1:1 v/v ethyl acetate-heptanes).

Preparation of (R)-methyl 5-(3-(2-formyl-5-oxopyrrolidin-1-yl)propyl)thiophene-2-carboxylate (6f)

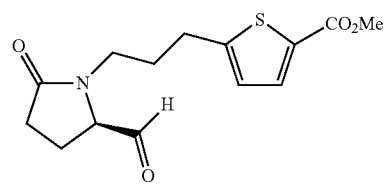 [SMILES: COC(=O)c1ccc(CCCN2C(=O)CC[C@@H]2C=O)s1]

Scheme 5: Preparation of (R)-methyl 5-(3-(2-(hydroxymethyl)-5-oxopyrrolidin-1-yl)propyl)thiophene-2-carboxylate (5f)

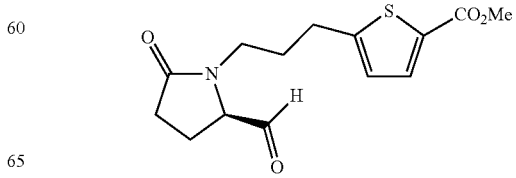

To a solution of (R,Z)-methyl 5-(3-(2-(hydroxymethyl)-5-oxopyrrolidin-1-yl)prop-1-en-1-yl)thiophene-2-carboxylate (5e, 496 mg) in ethyl acetate (40 mL) and methanol (4 mL) was added palladium on carbon (10%, (40 mg) and the flask evacuated and exposed to hydrogen for 4 hours. The mixture was then filtered through Celite and the solvent removed to afford the title intermediate in a quantitative yield, which was used without purification; TLC $R_f$ 0.25 (solvent system 95:5 v/v dichloromethane:methanol); $^1$H-NMR (CDCl$_3$); δ 7.6 (d, 1H), 6.6 (d, 1H), 3.85 (s, 3H), 3.8 (dd, 1H) 3.75-3.65 (m, 2H), 3.6 (dd, 1H), 3.1 (m, 1H), 2.85 (t, 2H), 2.7-2.4 (br s, 1H), 2.5-2.4 (m, 1H), 2.35-2.25 (m, 1H), 2.1-1.8 (m, 4H); MS (ESI$^+$) m/z 298.0 (M+1), 320.0 (M+Na$^+$).

Scheme 2, Step F: Preparation of (R)-methyl 5-(3-(2-formyl-5-oxopyrrolidin-1-yl)propyl)thiophene-2-carboxylate (6f)

(R)-Methyl 5-(3-(2-formyl-5-oxopyrrolidin-1-yl)propyl) thiophene-2-carboxylate was prepared in the same manner as compound 6a in Scheme 2, Step F except that (R)-methyl 5-(3-(2-(hydroxymethyl)-5-oxopyrrolidin-1-yl)propyl)thiophene-2-carboxylate (5f) was used instead of (R)-methyl 7-(2-(hydroxymethyl)-5-oxopyrrolidin-1-yl)heptanoate; TLC $R_f$ 0.25 (solvent system 95:5 v/v dichloromethane:methanol).

Organic β-keto phosphonate esters such as 13d-l may be used as reaction coupling partners with aldehydes such as 6a-f in a Horner-Emmons-Wadsworth-type process to install the lactam lower-chain scaffold. Such phosphonate esters may be prepared by coupling an appropriate carboxylic ester 12a-l with lithiated/deprotonated dimethyl methylphosphonate according to the general reaction illustrated in Scheme 6 and variations thereof. Esters 12a-l may be commercially available or prepared from commercially-available starting materials as shown in Schemes 7a-e.

As illustrated in Scheme 7a, a 2-($C_1$-$C_4$ alkyl) or 2-unsubstituted diethyl malonate may be alkylated with propargyl bromides to provide the corresponding 2-propargylated diethyl malonate intermediates 14a-c (Step A). Subsequent decarboxylation (Step B) provides the corresponding ester intermediate 12a, wherein both $R^4$ and $R^5$ are hydrogen, or intermediate mixture 12b-c, wherein one of $R^4$ and $R^5$ is a $C_1$-$C_4$ alkyl group and the other is a hydrogen. The 2-($C_1$-$C_4$ alkyl) diethyl malonates, also referred to as diethyl ($C_1$-$C_4$ alkyl) malonates, may either be purchased or prepared from diethyl malonate. Examples of diethyl ($C_1$-$C_4$ alkyl) malonates that may be purchased include diethyl methyl malonate, diethyl ethyl malonate, diethyl isopropyl malonate, diethyl n-propyl malonate, diethyl n-butyl malonate (all from Sigma-Aldrich, Acros Organics, or Alfa Aesar), diethyl isobutyl malonate, and diethyl sec-butyl malonate (both from Alfa Aesar), Methods for preparing the starting diethyl ($C_1$-$C_4$ alkyl) malonates are known in the art; for example, diethyl malonate may be combined with a base such as potassium carbonate and an appropriate alkylating agent such as methyl iodide, ethyl iodide, n-propyl bromide, or n-butyl bromide under microwave irradiation in the method described by Keglevich et al. in *Letters in Organic Chemistry*, 2008, 5(3), 224-228 and in *Green Chemistry*, 2006, 8(12), 1073-1075. Other methods that may be used to prepare the diethyl ($C_1$-$C_4$ alkyl) malonates include the reaction of diethyl malonate with an appropriate alkylating agent such as ethyl iodide, isopropyl bromide, isobutyl bromide, or sec-butyl bromide in the presence of a base such as sodium ethoxide in an organic solvent such as ethanol as described in Patel and Ryono in *Bioorganic and Medicinal Chemistry Letters*, 1992, 2(9), 1089-1092 and elsewhere.

Scheme 7b illustrates alkylations of ethyl phenyl-($C_2$-$C_5$) alkanoate esters 12f with an alkylating agent $R^4/R^5$—$X^1$, wherein the $R^4/R^5$ group is a $C_1$-$C_4$ alkyl group and $X^1$ is a leaving group such as iodide or bromide to provide α-alkylated esters 12d-e, g-l.

Enantiopure esters 12b and 12c may be prepared as illustrated in Scheme 7c. Alkylation of appropriately-substituted carboxylic acids, such as propionic acid ($R^4/R^5$ is a methyl group), at the carbon position alpha to the acid carbonyl group by treatment of the acid with an appropriate base, such as lithium diisopropylamide (about two molar equivalents) in the presence of a suitable solvent, such as THF, with (3-bromoprop-1-yn-1-yl)benzene (Step A) and subsequent coupling of the resulting α-alkyl carboxylic acid with N-hydroxysuccinimide (NHS) forms the corresponding NHS ester (an activated ester) enantiomeric mixture 16b/16c (Step B). Displacement of the activated ester enantiomeric mixture 16b/16c with (R)-2-amino-2-phenylethanol in THF results in the mixture of two amide diastereomers 17b and 17c (Step C), which may be separated by chromatography to provide each pure diastereomer (Step D). Amide hydrolysis of each diastereomer to its corresponding carboxylic acid 18b and 18c, respectively (Steps E1 and E2, respectively), and subsequent esterification (Steps F1 and F2, respectively) provides individual ester enantiomers 12b and 12c, respectively.

Scheme 7d describes the preparation of saturated enantiopure esters 12d-e,g-l by a route very similar to that illustrated in Scheme 7c for the acetylene esters 12b and 12c.

Scheme 7e shows a synthetic pathway to enantiopure esters 12d,g,i,k employing the use of the chiral auxiliary for more-efficient (asymmetric) alkylation in Step C. Removal of the chiral auxiliary (Step D) following alkylation and subsequent derivatization (Steps E and F) provides the diastereomers separable by chromatography and further purified by crystallization (Step G). Acid-catalyzed amide hydrolysis (Step H) and subsequent esterification (Step I) provide highly-pure and highly enantioenriched ester enantiomers 12d,g,i,k.

Schemes 8a, 8b, and 8c illustrate the conversions of esters 12a-l to β-keto phosphonates 13a-l by way of the addition of lithiated dimethyl methyl phosphonate to the starting esters. Schemes 8a and 8b particularly show the formation of acetylene β-keto phosphonates 13a-c (Step A) and subsequent catalytic hydrogenation (Step B) to corresponding β-keto phosphonates 13f-h. Scheme 8b more particularly illustrates the conversion of the enantiopure acetylene α-methyl ester 12b(i) ($R^4$ is methyl and $R^5$ is hydrogen) to the corresponding acetylene-keto phosphonate 13b(i) (Step A) and subsequent catalytic hydrogenation (Step B) to provide the enantiopure β-keto phosphonate 13g(i). Scheme 8c shows the conversion of saturated ester intermediates of varying chain length 12d-l to the corresponding saturated β-keto phosphonates 13d-l.

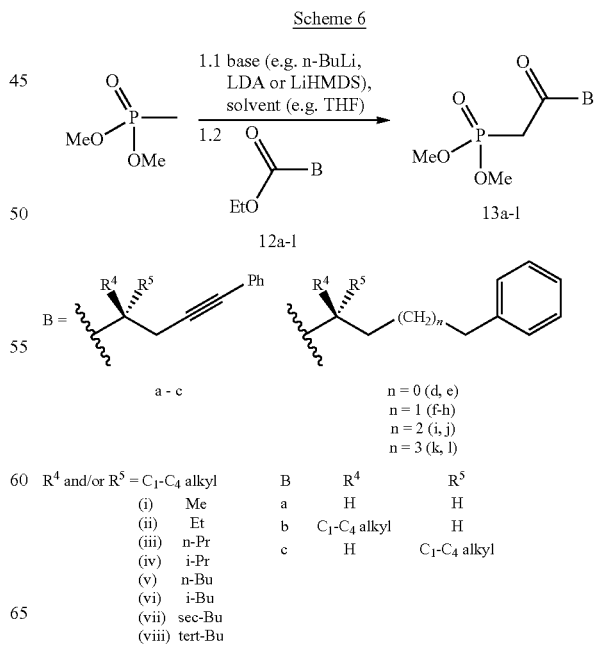

Scheme 6

| B | $R^4$ | $R^5$ |
|---|---|---|
| d | $C_1$-$C_4$ alkyl | H |
| e | H | $C_1$-$C_4$ alkyl |
| f | H | H |
| g | $C_1$-$C_4$ alkyl | H |
| h | H | $C_1$-$C_4$ alkyl |
| i | $C_1$-$C_4$ alkyl | H |
| j | H | $C_1$-$C_4$ alkyl |
| k | $C_1$-$C_4$ alkyl | H |
| l | H | $C_1$-$C_4$ alkyl |
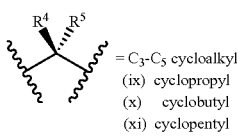
= $C_3$-$C_5$ cycloalkyl
(ix) cyclopropyl
(x) cyclobutyl
(xi) cyclopentyl
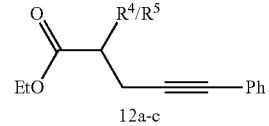
12a-c
Scheme 7a
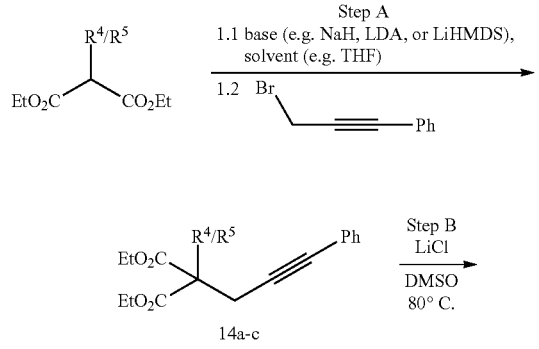
Scheme 7b
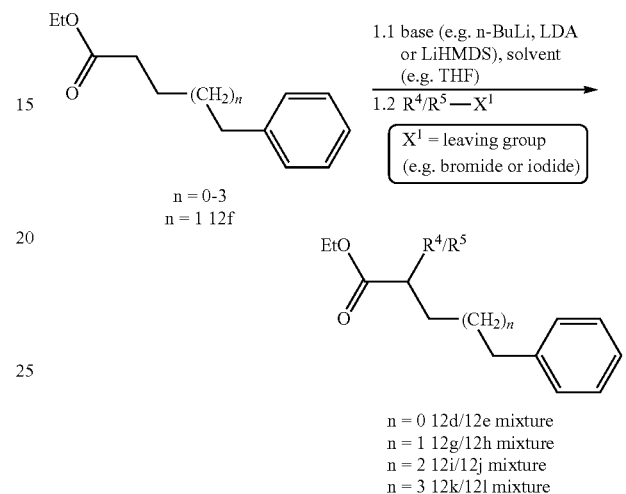
n = 0 12d/12e mixture
n = 1 12g/12h mixture
n = 2 12i/12j mixture
n = 3 12k/12l mixture
Scheme 7c
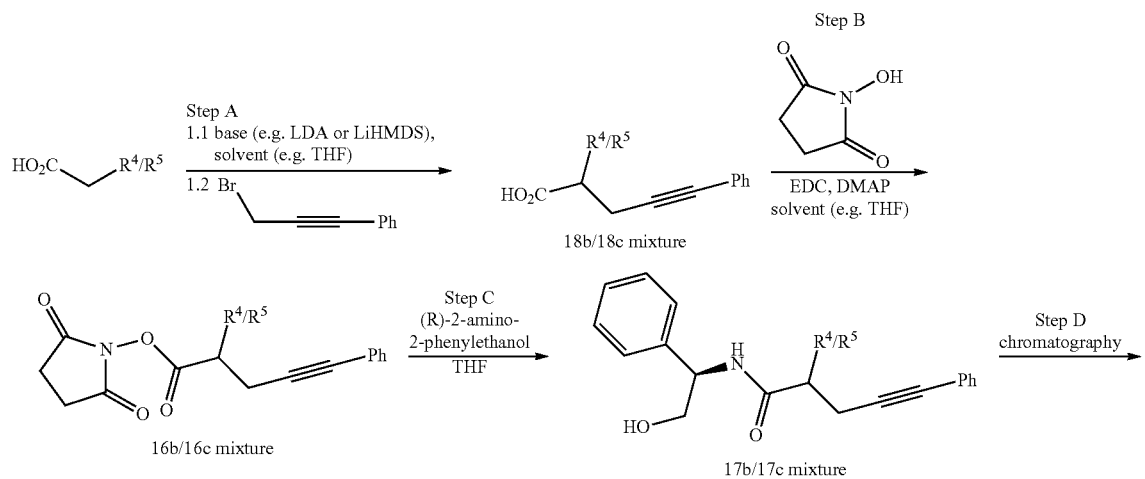
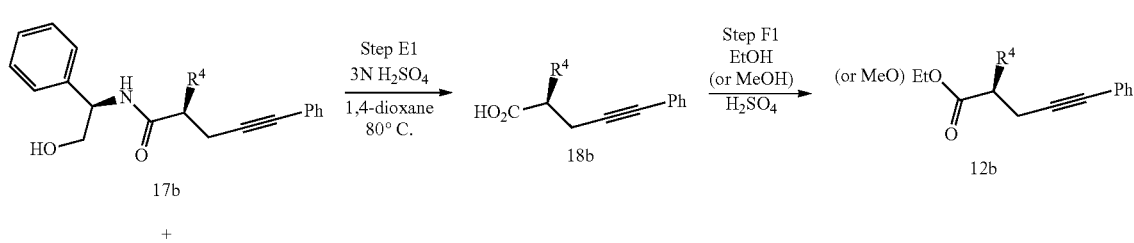

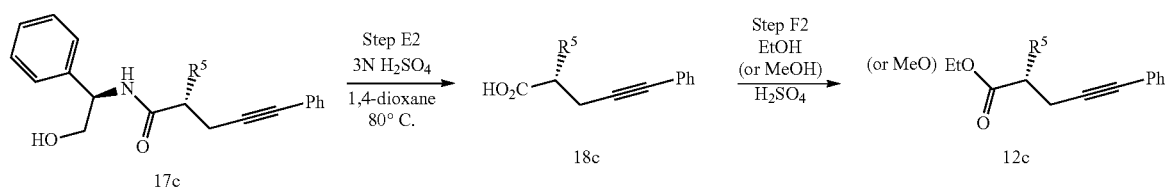
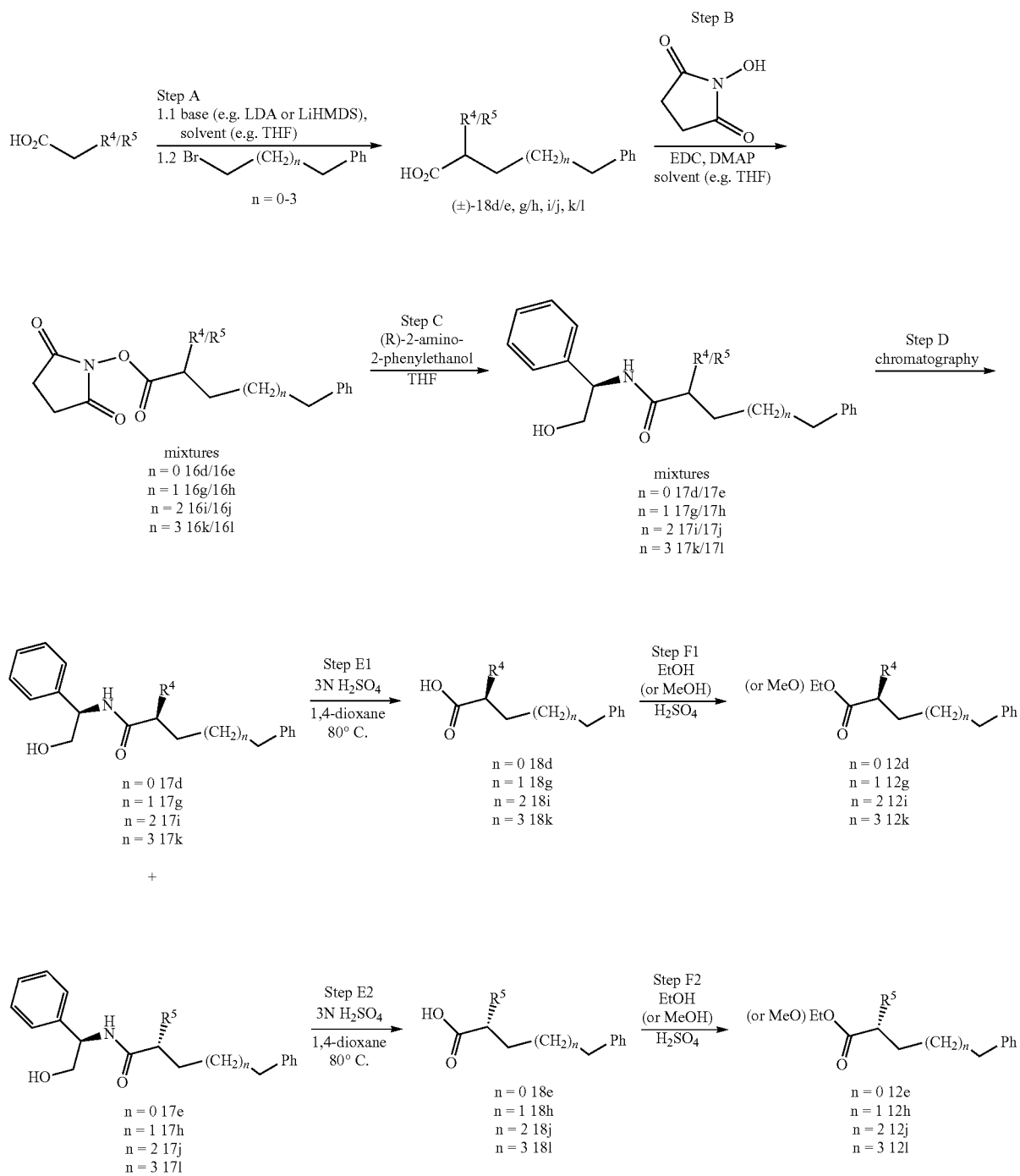
Scheme 7d

-continued
Scheme 7e
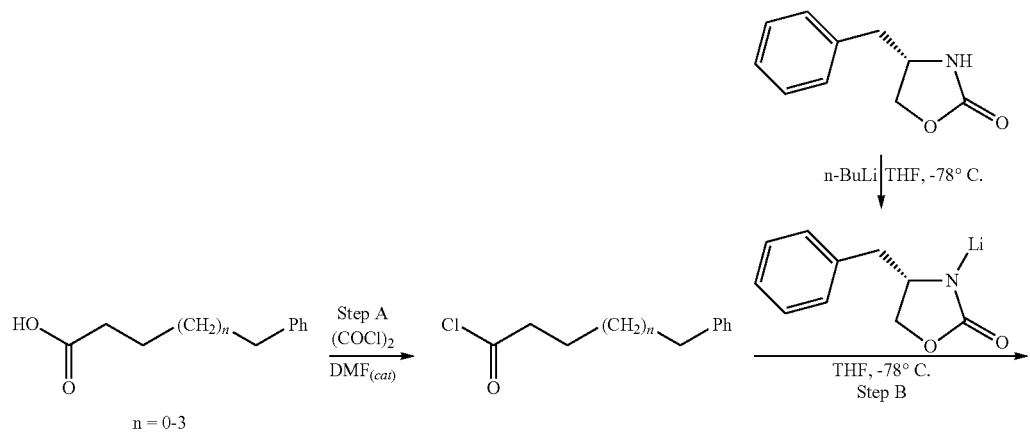
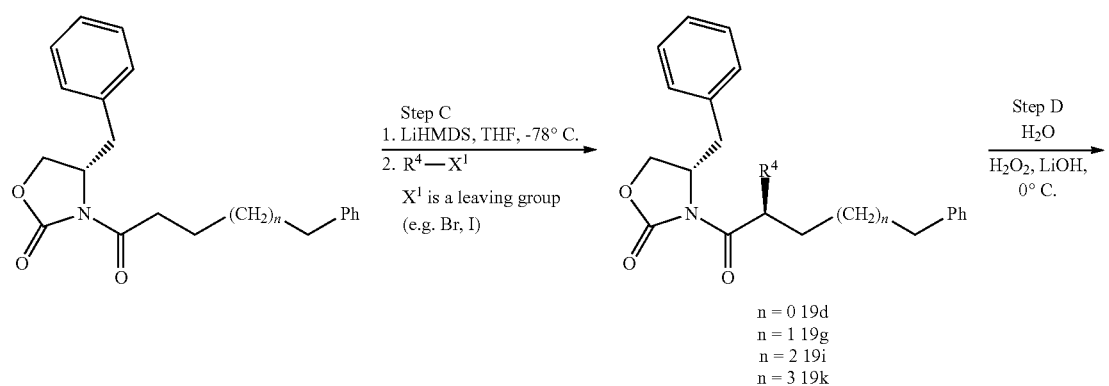
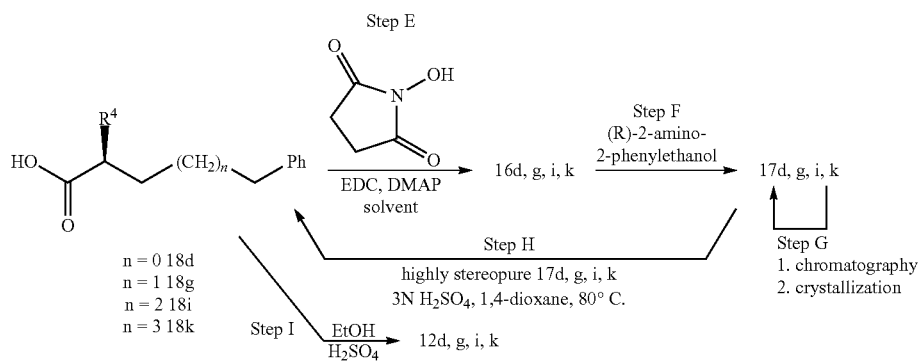
Scheme 8a
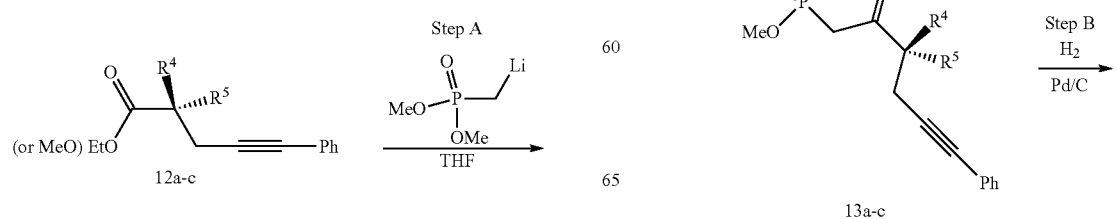

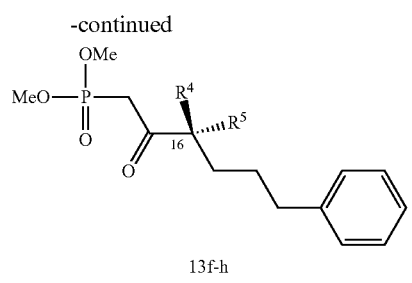
13f-h
Scheme 8b
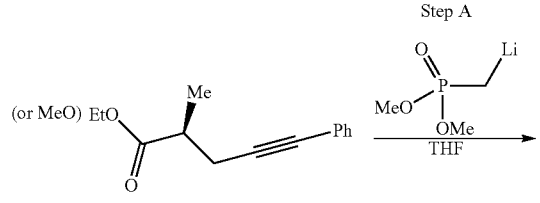
12b(i)
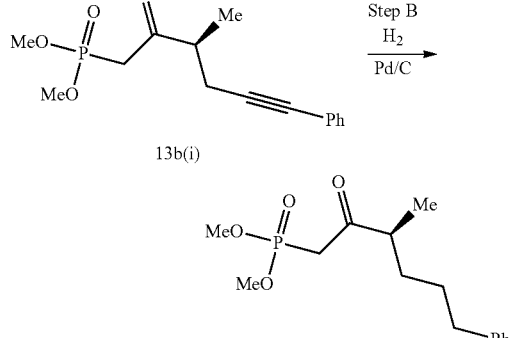
13b(i)
13g(i)
Scheme 8c
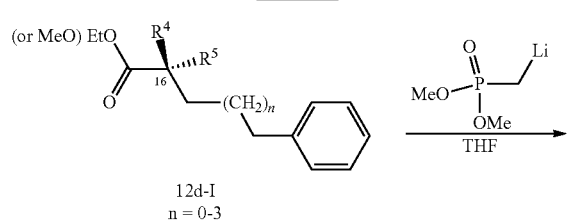
12d-I
n = 0-3
13d-I
n = 0-3
TABLE A
Phosphonate Ester
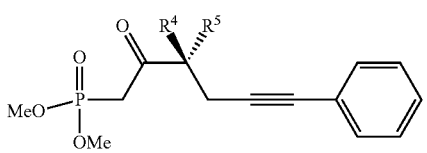
13a-c
| phosphonate ester | R⁴ | R⁵ |
|---|---|---|
| 13a | H | H |
| 13b | Me | H |
| 13c | H | Me |
TABLE B
Phosphonate Ester
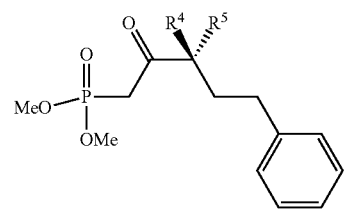
13d-e
| phosphonate ester | R⁴ | R⁵ |
|---|---|---|
| 13d | Me | H |
| 13e | H | Me |
TABLE C
Phosphonate Ester
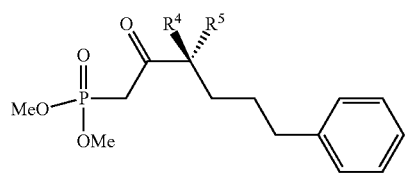
13f-h
| phosphonate ester | R⁴ | R⁵ |
|---|---|---|
| 13f | H | H |
| 13g | Me | H |
| 13h | H | Me |

TABLE D

Phosphonate Ester 13i-j

| phosphonate ester | R⁴ | R⁵ |
|---|---|---|
| 13i | Me | H |
| 13j | H | Me |

TABLE E

Phosphonate Ester 13k-l

| phosphonate ester | R⁴ | R⁵ |
|---|---|---|
| 13k | Me | H |
| 13l | H | Me |

Preparation of dimethyl (2-oxo-6-phenylhexyl)phosphonate (13f)

Scheme 8c: Preparation of dimethyl (2-oxo-6-phenylhexyl)phosphonate (13f) from methyl 5-phenylvalerate (121)

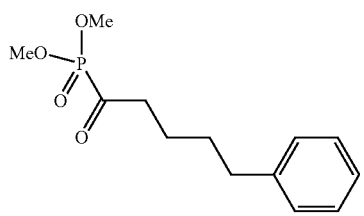 [SMILES: COP(=O)(OC)C(=O)CCCCc1ccccc1]

To a solution consisting of dimethyl methylphosphonate (2.0 g, 10.1 mmol) in THF (60 mL) at −78° C. was slowly added n-butyllithium (4.4 mL, 10.1 mmol, 2.5M solution in hexane). The mixture was stirred for 90 minutes, at which time a solution comprising methyl 5-phenylvalerate (Sigma-Aldrich, 1.9 g, 10 mmol) was added slowly, and the reaction mixture was allowed to warm to −10° C. while stirring over 5 hours. The reaction mixture was poured into 0.5 N HCl. The organic material was extracted twice with ethyl acetate. The organic phase was washed with water and a saturated solution of sodium chloride, dried over magnesium sulfate, filtered, and concentrated. The residue was purified by silica gel chromatography eluting with a gradient of ethyl acetate-hexane (1:1 to 65:35 v/v) to afford the title intermediate (1.5 g, 53%); ¹H-NMR (CDCl₃) δ 7.29-7.23 (m, 2H), 7.19-7.13 (m, 3H), 3.76 (d, 6H, J=11.1 Hz), 3.06 (d, 2H, J=22.6 Hz), 2.55-2.7 (m, 4H), 1.55-1.7 (m, 4H).

Alternative preparation of dimethyl (2-oxo-6-phenylhexyl)phosphonate (13f)

Scheme 7a, Step A: Preparation of diethyl 2-(3-phenylprop-2-yn-1-yl)malonate (14a)

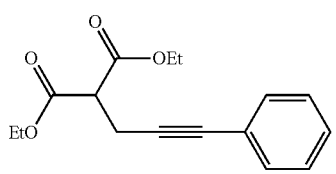 [SMILES: CCOC(=O)C(CC#Cc1ccccc1)C(=O)OCC]

To a stirring suspension consisting of sodium hydride (1.22 g, 51.3 mmol) in THF (100 mL) at 0° C. was added dropwise a solution consisting of diethyl malonate (12.3 g, 76.9 mmol) in THF (20 mL) and the reaction mixture was stirred for 30 minutes. To the 0° C. reaction mixture was added a solution consisting of (3-bromoprop-1-yn-1-yl)benzene (5.0 g, 26 mmol, prepared from the corresponding commercially available alcohol using PBr₃/pyridine) in THF (30 mL) and the mixture was allowed to warm to room temperature and stirred for one hour. The reaction mixture was quenched with an aqueous solution of sodium chloride (500 mL) and extracted with diethyl ether (500 mL). The organic phase was washed with brine (300 mL), dried over sodium sulfate, filtered, and concentrated to afford the title intermediate (10.6 g, crude), which was used without further manipulation in the subsequent reaction; TLC R_f 0.47 (solvent system: 1:5 v/v ethyl acetate-heptane).

Scheme 7a, Step B: Preparation of ethyl 5-phenylpent-4-ynoate (12a)

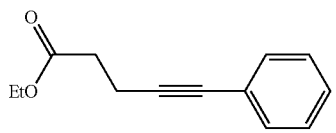 [SMILES: CCOC(=O)CCC#Cc1ccccc1]

To a stirring solution consisting of diethyl 2-(3-phenyl-prop-2-yn-1-yl)malonate (14a, 10.6 g crude) in DMSO (40 mL) was added water (1.4 mL) and lithium chloride (1.77 g, 40.5 mmol), and the reaction mixture was heated to 160° C. while stirring overnight. The reaction mixture was cooled, diluted with ethyl acetate, and washed with 50% saturated sodium chloride solution followed by saturated aqueous sodium chloride. The organic phase was dried over sodium sulfate and concentrated under vacuum. The residue was purified by silica gel chromatography eluting with ethyl acetate-hexane (5:95 v/v) to afford the title intermediate (2.74 g, 53%, 2 steps); TLC R_f 0.26 (solvent system: 5:95 v/v ethyl acetate-hexane).

Scheme 8a, Step A: Preparation of dimethyl (2-oxo-6-phenylhex-5-yn-1-yl)phosphonate (13a)

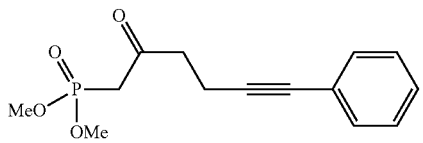

To a solution consisting of dimethyl methylphosphonate (2.6 g, 14 mmol) in THF (150 mL) at −78° C. was slowly added n-butyllithium (12.7 mL, 20.3 mmol, 1.6 M solution in hexane). The mixture was stirred for 45 minutes, at which time ethyl 5-phenylpent-4-ynoate (12a, 2.74 g, 13.5 mmol) was added slowly, and the reaction mixture was stirred for 2 hours. The reaction mixture was carefully treated with a 5% aqueous solution of potassium hydrogen sulfate and a 50% saturated aqueous sodium chloride solution. The organic material was extracted with diethyl ether, dried over sodium sulfate, and concentrated under vacuum. The residue was purified by silica gel chromatography eluting with ethyl acetate-hexane (80:20 v/v) to afford the title intermediate (2.12 g, 56%); TLC $R_f$ 0.2 (solvent system: 80:20 v/v ethyl acetate-hexane); MS (ESI+) m/z 281 (M+1).

Scheme 8a, Step B: Preparation of dimethyl (2-oxo-6-phenylhexyl)phosphonate (13f)

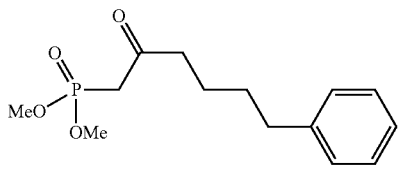 [SMILES: COP(=O)(CC(=O)CCCCc1ccccc1)OC]

Dimethyl (2-oxo-6-phenylhex-5-yn-1-yl)phosphonate (13a) is hydrogenated over 10% palladium on activated carbon in methanol by stirring under an atmosphere of hydrogen over night. The hydrogen is evacuated and the mixture is filtered through a micropore filter. The filtrate is concentrated in vacuo to afford the title intermediate.

Preparation of phosphonate esters 13b-c,g-h(i)

Scheme 7a, Step A: Preparation of diethyl 2-methyl-2-(3-phenylprop-2-yn-1-yl)malonate [14b/c(i)]

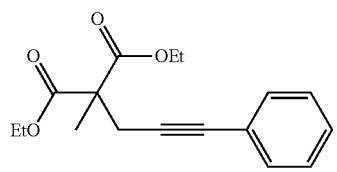

To a stirring mixture consisting of diethyl 2-methylmalonate (Sigma-Aldrich, 3.7 g, 21 mmol) in THF (200 mL) at −78° C. was slowly added lithium bis-(trimethylsilyl)amide (1 M in THF, 23.6 mL, 23.6 mmol) and the resulting reaction mixture was stirred at −78° C. for 40 minutes. To the reaction mixture was added a mixture consisting of (3-bromoprop-1-yn-1-yl)benzene (4.6 g, 24 mmol, prepared from the corresponding alcohol using PBr₃/pyridine method) in THF (50 mL), and the mixture was stirred for another hour at −78° C., and was then allowed to warm to room temperature over night. The mixture was quenched with 1 N_HCl (40 mL) and extracted twice with diethyl ether. The organic phase was washed twice with water, then with brine, was dried over magnesium sulfate, filtered, and concentrated to afford the title intermediate (6.78 g, quantitative yield) as a yellow oil.

Scheme 7a, Step B: Preparation of (±)-ethyl 2-methyl-5-phenylpent-4-ynoate [12b/c(i)]

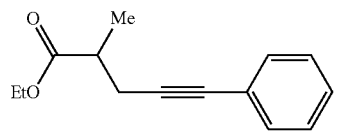 [SMILES: CCOC(=O)C(C)CC#Cc1ccccc1]

The title intermediate was prepared in the manner similar to that of ethyl 5-phenylpent-4-ynoate (12a) through the decarboxylation of diethyl 2-methyl-2-(3-phenylprop-2-yn-1-yl)malonate [14b/c(i)] under the conditions of lithium chloride, water and DMSO. The crude product was purified by silica gel chromatography eluting with a gradient of ethyl acetate-hexane (1:99 to 7:93 v/v) to afford the racemic title intermediate (3.2 g, 70%, 2 steps).

Scheme 8a, Step A: Preparation of (±)-dimethyl (3-methyl-2-oxo-6-phenylhex-5-yn-1-yl)phosphonate [13b/c(i)]

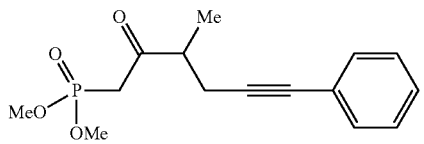

The title β-keto phosphonate intermediate was prepared from (±)-ethyl 2-methyl-5-phenylpent-4-ynoate [12b/c(i)] in a manner similar to that of intermediate dimethyl (2-oxo-6-phenylhexyl)phosphonate (13f) as described above to afford a clear oil (2.4 g, 55%); ¹H-NMR (CDCl₃) δ 7.35-7.45 (m, 2H), 7.2-7.3 (m, 3H), 3.85-3.75 (m, 6H), 3.25 (d, 2H), 3.0-3.2 (m, 1H), 2.5-2.7 (m, 2H), 1.25 (d, 3H); MS (ESI+) m/z 295.1 (M+1).

Scheme 8a, Step B: Preparation of (±)-dimethyl (3-methyl-2-oxo-6-phenylhexyl)phosphonate [13g/h(i)]

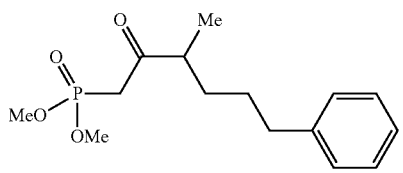 [SMILES: COP(=O)(CC(=O)C(C)CCCc1ccccc1)OC]

A racemic mixture consisting of (±)-dimethyl (3-methyl-2-oxo-6-phenylhex-5-yn-1-yl)phosphonate [13b/c(i)], (1.0 g, 3.4 mmol) and 10% palladium on activated carbon (15 mg) in methanol (30 mL) was stirred under an atmosphere of hydrogen over night. The hydrogen was evacuated and the mixture was filtered through a micropore filter. The filtrate was concentrated in vacuo to afford the title racemic β-keto phosphonate intermediate (1.0 g, quantitative yield) as a clear oil; $^1$H-NMR (CDCl$_3$) δ 7.3-7.25 (m, 2H), 7.2-7.1 (m, 3H), 3.8-3.7 (m, 6H), 3.1 (d, 2H), 2.8-2.75 (m, 1H), 2.7-2.5 (m, 2H), 1.8-1.65 (m, 1H), 1.65-1.5 (m, 2H), 1.4-1.3 (m, 1H), 1.1 (d, 3H); MS (ESI$^+$) m/z 299 (M+1).

Schemes 7d & 8c: Preparation of dimethyl (S)-(+)-(3-methyl-2-oxo-6-phenylhexyl)phosphonate [13g(i)]

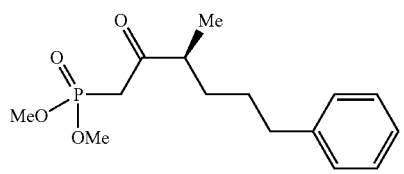 [SMILES: COP(=O)(CC(=O)[C@@H](C)CCCc1ccccc1)OC]

Scheme 7d, Step A: Preparation of (±)-2-methyl-5-phenylpentanoic acid

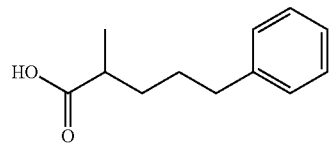

To a solution consisting of diisopropylamine (218.25 mL, 1557.3 mmol) in THF (400 mL) at −50° C. was added n-butyllithium (628 mL, 393 mmol, 1.6 M solution in hexane). The mixture was stirred for 5 minutes and was subsequently allowed to warm to −20° C. To the reaction mixture was added dropwise a solution consisting of propionic acid (44.7 g, 603 mmol) in HMPA (102 mL). The mixture was stirred at room temperature for 30 minutes, cooled to 0° C., and treated with a mixture consisting of 1-bromo-3-phenylpropane (100 g, 502 mmol) in THF (200 mL). The mixture was stirred at room temperature for 2 hours. The reaction mixture was diluted with water and extracted with ethyl acetate. The aqueous layer was separated and then acidified with 2 M HCl until acidic. The aqueous layer was then extracted three times with ethyl acetate, and the organic layers were combined and dried over sodium sulfate, filtered, and concentrated to provide the title intermediate (105 g, quantitative yield) as a clear oil; TLC R$_f$ 0.44 (solvent system: 25:75:1 v/v/v ethyl acetate-heptane-acetic acid.

Scheme 7d, Step B: Preparation of (±)-2,5-dioxopyrrolidin-1-yl 2-methyl-5-phenylpentanoate [16g/h(i)]

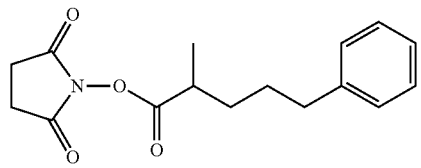 [SMILES: CC(CCCc1ccccc1)C(=O)ON1C(=O)CCC1=O]

To a mixture consisting of (±)-2-methyl-5-phenylpentanoic acid (105.6 g, 549.1 mmol) in dichloromethane (800 mL) was added N-hydroxysuccinimide (69.5 g, 604 mmol), 4-dimethylaminopyridine (73.8 g, 604 mmol) and 1-ethyl-(3-dimethylaminopropyl) carbodiimide hydrochloride (115.8 g, 604.0 mmol) and the mixture stirred overnight at room temperature. The mixture was extracted with dichloromethane and washed twice with brine, dried over sodium sulfate, filtered, and concentrated under vacuum. The residue was purified by silica gel chromatography eluting with ethyl acetate-heptane (30:70 v/v) to afford 85.6 g (54%) of the title intermediate; TLC R$_f$ 0.32 (solvent system 25:75 v/v ethyl acetate-heptane.

Scheme 7d, Step C: Preparation of (S)—N—((R)-2-hydroxy-1-phenylethyl)-2-methyl-5-phenylpentanamide [17g(i)]

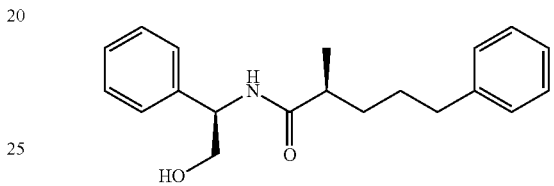

To a solution consisting of (±)-2,5-dioxopyrrolidin-1-yl 2-methyl-5-phenyl pentanoate (16g/h(i), 85.6 g, 296 mmol) in THF (3000 mL) at 48° C. was added R-(−)-2-phenylglycinol (65.9 g, 480 mmol, Bridge Organics) in portions, and the mixture stirred at 48° C. for 40 hours. The white precipitate was filtered from the reaction mixture and washed with THF. The filtrate was concentrated under vacuum and the residue, comprising the diastereomeric pair, was chromatographed on silica gel eluting with ethyl acetate-heptane (50:50 v/v). The stereopure title intermediate was obtained (31.3 g; 34%) as a colorless solid; TLC R$_f$ 0.205 (solvent system: 50:50 v/v ethyl acetate-heptane); HPLC retention time 15.1 minutes, stationary phase: Gemini 5μ C18 250×4.6 mm, ultraviolet detector at 210 nm, mobile phase: 1 mL/min, 60:40:0.1 v/v methanol-water-acetic acid.

Scheme 7d, Step D: Preparation of (S)-(+)-2-methyl-5-phenylpentanoic acid [18g(i)]

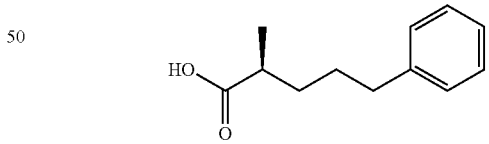

To a solution consisting of (S)—N—((R)-2-hydroxy-1-phenylethyl)-2-methyl-5-phenylpentanamide (17g(i), 3.5 g, 11 mmol) in 1,4-dioxane (80 mL) was added sulfuric acid (36 mL, 3 N solution in water) and the mixture was stirred overnight at 80° C. The reaction mixture was extracted with ethyl acetate three times and the organic layers were combined, dried over sodium sulfate, filtered and concentrated under vacuum. The residue was purified by silica gel chromatography eluting with ethyl acetate-heptane-acetic acid (30:70:0.4 v/v/v) to afford the title intermediate (2.4 g; quantitative yield) as a clear oil; R$_f$ 0.48 (solvent system: 30:70:0.4 v/v/v ethyl acetate-heptane-acetic acid; HPLC retention time 26.0 minutes; Chiralpak IA, 5μ, 4.6×25 mm, ultraviolet detector at 208 nm 0.75 ml/min 99:1:0.5 v/v heptanes-2-propanol-acetic acid; MS (ESI⁻) m/z 191.1 (M−1); ¹H-NMR (CDCl₃) δ 7.33-7.27 (m, 2H), 7.22-7.16 (m, 3H), 2.67-2.60 (m, 2H), 2.56-2.46 (m, 1H), 1.80-1.60 (m, 3H), 1.59-1.36 (m, 1H), 1.25-1.14 (m, 3H); $[\alpha]^T_\lambda$=α/cl, $[\alpha]^{21.9}_D$=+0.089/(0.01501 g/1.5 mL)(0.5)=+17.79° (c=1, CHCl₃).

Scheme 7d, Step E1: Preparation of (S)-(+)-ethyl 2-methyl-5-phenylpentanoate [12g(i)]

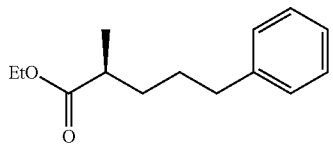 [SMILES: CCOC(=O)[C@@H](C)CCCc1ccccc1]

To a solution consisting of (S)-(+)-2-methyl-5-phenylpentanoic acid (18g(i), 2.3 g, 12 mmol) in ethanol (200 mL) was added 4 drops of sulfuric acid and the mixture heated at reflux overnight. The mixture was cooled and subsequently concentrated under vacuum. The residue was diluted with ethyl acetate and washed twice with brine. The organic layer was dried over sodium sulfate, filtered, and concentrated under vacuum to afford the title intermediate (2.4 g; 91%) as a clear oil; TLC $R_f$ 0.66 (solvent system: 15:85:1 v/v/v ethyl acetate-heptane-acetic; MS (ESI⁺⁾ m/z 221.2 (M+1); ¹H-NMR (CDCl₃) 7.29-7.25 (m, 2H), 7.21-7.13 (m, 3H), 4.12 (q, J=6.96 Hz, 2H), 2.64-2.57 (m, 2H), 2.48-2.39 (m, 1H), 1.75-1.54 (m, 3H), 1.52-1.41 (m, 1H), 1.24 (t, J=7.14 Hz, 3H) 1.16-1.11 (m, 3H); $[\alpha]^T_\lambda$=α/cl, $[\alpha]^{21.9}_v$=+0.101/ (0.01506 g/1.5 mL)(0.5)=+20.12° (c=1, CHCl₃).

Scheme 8c: Preparation of (S)-(+)-dimethyl (3-methyl-2-oxo-6-phenylhexyl)phosphonate [13g(i)]

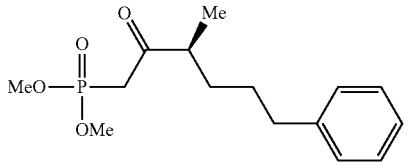 [SMILES: COP(=O)(CC(=O)[C@@H](C)CCCc1ccccc1)OC]

To a solution consisting of dimethyl methylphosphonate (23.37 g, 188.4 mmol) in THF (400 mL) at −78° C. was slowly added n-butyllithium (112 mL, 179 mmol, 1.6 M solution in hexane). The mixture was stirred for 30 minutes, at which time (S)-(+)-ethyl 2-methyl-5-phenylpentanoate (12g(i), 28.1 g, 94.2 mmol) in THF (100 mL) was added slowly, and the mixture stirred at −78° C. for 2 hours, after which time it was allowed to come to room temperature overnight. The reaction mixture was treated with 5% KHSO₄ and extracted with ethyl acetate three times. The organic layer was washed twice with 50:50 water-brine and the organic layer was dried over sodium sulfate, filtered, and concentrated under vacuum. The residue was purified by silica gel chromatography eluting with ethyl acetate-heptane (60:40 v/v) to afford the enantiopure title β-keto phosphonate intermediate (11.9 g) as a clear oil, pure of unrelated components; TLC $R_f$ 0.22 (solvent system: 60:40 v/v ethyl acetate-heptane); HPLC retention time 14.5 minutes, 5μ Chiralpak IA 250×4.6 mm, ultraviolet detector at 210 nm, 1 ml/min, 90:10:0.01 v/v/v heptane-isopropanol-acetic acid chiral purity 97.8% (S), 2.19% (R); MS (ESI⁻) m/z 297.1 (M−1); ¹H NMR (CDCl₃) δ 7.28-7.21 (m, 2H), 7.17-7.12 (m, 3H), 3.76-3.71 (m, 6H), 3.10 (d, J=2.20 Hz, 1H), 3.04 (d, J=2.20 Hz, 1H), 2.79-2.70 (m, 1H), 2.54-2.62 (m, 2H), 1.74-1.54 (m, 3H), 1.42-1.24 (m, 1H), 1.07 (d, J=6.96 Hz, 3H); $[\alpha]^T_\lambda$=α/cl, $[\alpha]^{21.9}_D$=+0.084/(0.0169 g/1.5 mL)(0.5)=+14.91° (c=1.13, CHCl₃). The chromatography also provided another portion (8.3 g) of the title β-keto phosphonate intermediate; about 95% chemical purity based on visual observation of TLC; HPLC retention time 16.399 minutes, 5 t Chiralcel OJ-H 250×4.6 mm, ultraviolet detector at 210 nm, 1 ml/min, 90:10:0.01 v/v/v heptanes-ethanol-acetic acid, chiral purity 98.19% (S), 1.81% (R).

Schemes 7d and 8c: Preparation of dimethyl (R)-(3-methyl-2-oxo-6-phenylhexyl)phosphonate [13h(i)]

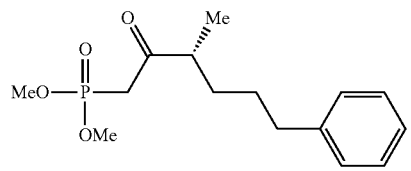

Scheme 7d, Step C: Preparation of (R)—N—((R)-2-hydroxy-1-phenylethyl)-2-methyl-5-phenylpentanamide [17h(i)]

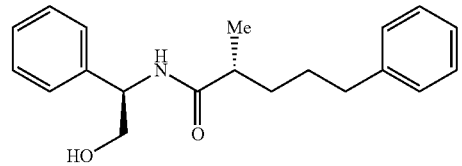 [SMILES: C[C@H](CCCc1ccccc1)C(=O)N[C@@H](CO)c1ccccc1]

(R)—N—((R)-2-Hydroxy-1-phenylethyl)-2-methyl-5-phenylpentanamide was isolated from the silica gel chromatography used to separate and isolate (S)—N—((R)-2-hydroxy-1-phenylethyl)-2-methyl-5-phenylpentanamide [17g(i)], as described above. The stereopure title intermediate was obtained (30.2 g; 33%) as a colorless solid; TLC $R_f$ 0.33 (solvent system: 50:50 v/v ethyl acetate-heptane); HPLC retention time 13.25 minutes, Gemini 5μ C18 250× 4.6 mm, at ultraviolet wavelength of 210 nm, 1 mL/min, 60:40:0.1 methanol-water-acetic acid; chiral purity 99.36% (R), 0.64% (S); $[\alpha]^T_\lambda$=α/cl, $[\alpha]^{21.9}_D$=−0.066/(0.01573 g/2 mL)(0.5)=−16.78° (c=0.7865, CHCl₃).

Scheme 7d, Step D: Preparation of (R)-(+)-2-methyl-5-phenylpentanoic acid [18h(i)]

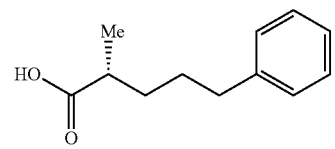 [SMILES: C[C@H](CCCc1ccccc1)C(=O)O]

(R)-(+)-2-Methyl-5-phenylpentanoic acid [18h(i)] was prepared in the same manner as (S)-2-methyl-5-phenylpentanoic acid [18g(i)]. The residue was purified by silica gel chromatography eluting with ethyl acetate-heptane-acetic acid (20:80:0.4 v/v/v) to afford the title intermediate (20.8 g) as a clear oil; TLC R$_f$ 0.51 (solvent system: 30:70:1 v/v/v ethyl acetate-heptane-acetic acid; HPLC retention time 24.46 min; Chiralpak IA 4.6×25 mm 5μ, at a wavelength of 208 nm 0.75 mL/min, 99:1:0.5 heptane: 2-propanol: acetic acid, chiral purity 99.32% (R), 0.68% (S); MS (ESI⁻) m/z 191.1 (M−1); $^1$H-NMR (CDCl$_3$) δ 7.31-7.26 (m, 2H), 7.21-7.15 (m, 3H), 2.67-2.57 (m, 2H), 2.54-2.44 (m, 1H), 1.79-1.59 (m, 3H) 1.58-1.41 (m, 1H), 1.18 (d, J=6.96 Hz, 3H).

Scheme 7d, Step E2: Preparation of (R)-ethyl 2-methyl-5-phenylpentanoate [12h(i)]

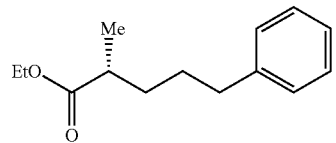 [SMILES: CCOC(=O)[C@H](C)CCCc1ccccc1]

(R)-Ethyl 2-methyl-5-phenylpentanoate [12h(i)] was prepared in the same manner as (S)-ethyl 2-methyl-5-phenylpentanoate [12g(i)]. The residue was purified by silica gel chromatography eluting with ethyl acetate-heptane (5:95 v/v) to afford the title intermediate (21.0 g, 88%) as a clear oil; TLC R$_f$ 0.66 (solvent system: 15:85:1 v/v/v ethyl acetate-heptane-acetic acid; MS (ESI⁺) m/z 221.2 (M+1); $^1$H-NMR (CDCl$_3$) δ 7.32-7.26 (m, 2H), 7.20-7.14 (m, 3H), 4.11 (q, J=7.32 Hz, 2H), 2.64-2.57 (m, 2H), 2.48-2.39 (m, 1H), 1.75-1.53 (m, 3H), 1.52-1.41 (m, 1H), 1.27-1.21 (m, 3H), 1.13 (d, J=6.96 Hz, 3H,); [α]$^T_\lambda$=α/cl, [α]$^{21.9}_D$=−0.114/(0.01771 g/1.5 mL)(0.5)=−19.31° (c=1.18, CHCl$_3$).

Scheme 8c: Preparation of (R)-dimethyl (3-methyl-2-oxo-6-phenylhexyl)phosphonate [13h(i)]

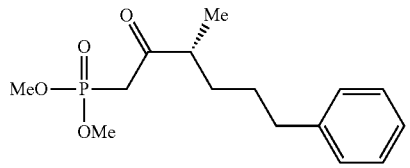 [SMILES: COP(=O)(CC(=O)[C@H](C)CCCc1ccccc1)OC]

(R)-Dimethyl (3-methyl-2-oxo-6-phenylhexyl)phosphonate [13h(i)] was prepared in the same manner as (S)-dimethyl (3-methyl-2-oxo-6-phenylhexyl)phosphonate [13g(i)]. The residue was purified by silica gel chromatography eluting with ethyl acetate-heptane (70:30 v/v) to afford the title phosphonate intermediate (83 mg, 66%) as a colorless oil; TLC R$_f$ 0.22 (solvent system: 70:30 v/v ethyl acetate-heptane); HPLC retention time 12.36 min, 5μ Chiralpak OJ-H 4.6×250 mm, at ultraviolet wavelength of 210 nm, 90:10:0.1 heptane:ethanol:acetic acid 1 mL/min, chiral purity 100% (R); MS (ESI⁻) m/z 297.1 (M−1); $^1$H NMR (CDCl$_3$) δ 7.29 (d, J=6.51 Hz, 2H,), 7.22-7.16 (m, 3H), 3.77 (d, J=11.35 Hz, 3H), 3.78 (d, J=11.35 Hz, 3H), 3.13 (d, J=1.83 Hz, 1H), 3.08 (d, J=1.83 Hz, 1H), 2.78 (d, J=6.96 Hz, 1H), 2.67-2.56 (m, 2H), 1.61-1.52 (m, 3H), 1.45-1.32 (m, 1H), 1.11 (d, J=6.96 Hz, 3H); [α]$^T_\lambda$=α/cl, [α]$^{21.9}_D$=−0.080/(0.01742 g/1.5 mL)(0.5)=−13.78° (c=1.16, CHCl$_3$).

Schemes 7e & 8c: Alternative preparation of dimethyl (S)-(+)-(3-methyl-2-oxo-6-phenylhexyl)phosphonate [13g(i)]

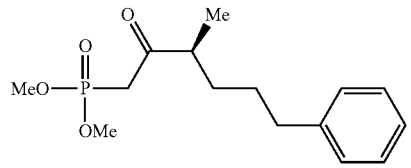 [SMILES: COP(=O)(CC(=O)[C@@H](C)CCCc1ccccc1)OC]

Scheme 7e, Steps A and B: Preparation of (S)-4-benzyl-3-(5-phenylpentanoyl)oxazolidin-2-one

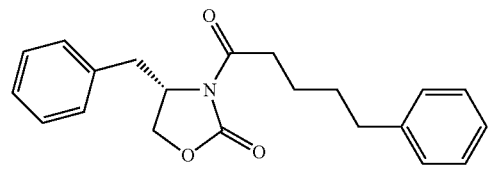 [SMILES: O=C(CCCCc1ccccc1)N1C(=O)OC[C@@H]1Cc1ccccc1]

To a solution consisting of (S)-4-benzyloxazolidin-2-one (0.9 g, 5.08 mmol) in THF (20 mL) at −78° C. was slowly added n-butyllithium (3.5 mL, 5.6 mmol, 1.6 M solution in hexane). The mixture was stirred at −78° C. for 2 hours, after which time 5-phenylpentanoyl chloride (1 g, 5 mmol, prepared by treatment of 5-phenylpentanoic acid with oxalyl chloride and catalytic DMF) was added slowly. The reaction mixture was stirred at −78° C. for 2 hours and was then allowed to rise to room temperature overnight. The mixture was acidified with 5% KHSO$_4$ and extracted twice with ethyl acetate. The organic phase was washed with brine, dried over sodium sulfate, filtered, and concentrated under vacuum. The residue was purified by silica gel chromatography eluting with ethyl acetate-heptane (25:75 v/v) to afford the title intermediate (1.4 g, 82%) as a clear oil; TLC R$_f$ 0.40 (solvent system: 25:75 v/v ethyl acetate-heptane); MS (ESI⁺4 m/z 337.4 (M+H)*, 360.2 (M+Na)⁺.

Scheme 7e, Step C: Preparation of (S)-4-benzyl-3-((S)-2-methyl-5-phenylpentanoyl)oxazolidin-2-one

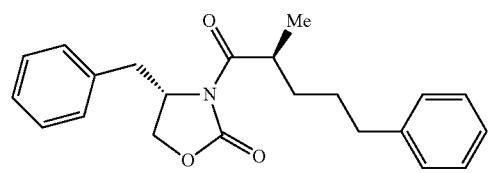 [SMILES: C[C@@H](CCCc1ccccc1)C(=O)N1C(=O)OC[C@@H]1Cc1ccccc1]

To a solution consisting of (S)-4-benzyl-3-(5-phenylpentanoyl)oxazolidin-2-one (1.24 g, 3.68 mmol) in THF (20 mL) at −78° C. was slowly added lithium bis-(trimethylsilyl) amide (4.41 mL, 4.41 mmol, 1 M solution in THF). The mixture was stirred at −78° C. for 1 hour, after which time iodomethane (0.27 mL, 4.2 mmol) was added slowly, and the mixture was allowed to rise to room temperature and stir overnight. The mixture was acidified with 5% KHSO₄ and extracted twice with ethyl acetate. The organic layer was washed twice with brine, dried over sodium sulfate, filtered and concentrated under vacuum. The residue was purified by silica gel chromatography eluting with ethyl acetate-heptane (25:75 v/v) to afford 563 mg (43.6%) of the title intermediate (563 mg, 43.6%) as a clear oil; TLC $R_f$ 0.53 (solvent system: 25:75 v/v ethyl acetate-heptane; MS (ESI⁺) m/z 352.3 (M+H)⁺ 374.2 (M+Na)⁺.

Scheme 7e, Step D: Preparation of (S)-2-methyl-5-phenylpentanoic acid [18g(i)]

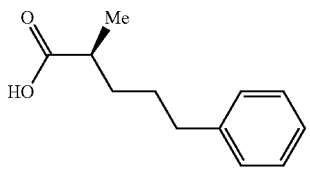 [SMILES: C[C@@H](CCCc1ccccc1)C(=O)O]

To a mixture consisting of (S)-4-benzyl-3-((S)-2-methyl-5-phenylpentanoyl)oxazolidin-2-one and water cooled to 0° C. was added hydrogen peroxide and lithium hydroxide. The reaction mixture was stirred for 4 hours and was subsequently acidified with 5% KHSO₄ and extracted twice with ethyl acetate, the organic layer was washed twice with brine, dried over sodium sulfate, and concentrated under vacuum. The residue was purified by silica gel chromatography eluting with ethyl acetate-heptane-acetic acid (25:75:0.4) to afford intermediate (293 mg, 95%) as a colorless oil; TLC $R_f$ 0.35 (solvent system: 25:75:0.4 v/v/v ethyl acetate-heptane-acetic acid); HPLC retention time 12.08 min, stationary phase: Chiralpak IA 4.6×250 mm 5μ, ultraviolet detector at 210 nm, mobile phase: 1 mL/min, 99:1:0.1 heptane: 2-propanol: acetic acid, chiral purity 97.22% (S), 2.78% (R).

Scheme 7e, Step E: Preparation of (S)-2,5-dioxopyrrolidin-1-yl 2-methyl-5-phenylpentanoate [16g(i)]

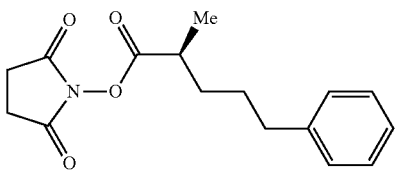 [SMILES: C[C@@H](CCCc1ccccc1)C(=O)ON1C(=O)CCC1=O]

To a mixture consisting of (S)-2-methyl-5-phenylpentanoic acid (18g(i), 290 mg, 1.51 mmol) in dichloromethane (20 mL) was added N-hydroxysuccinimide (191 mg, 1.66 mmol), 4-dimethylaminopyridine (203 mg, 1.66 mmol) and 1-ethyl-(3-dimethylaminopropyl)carbodiimide hydrochloride (318 mg, 1.66 mmol) and the mixture stirred for 2 hours at room temperature. The reaction mixture was used in the next step.

Scheme 7e, Step F and G: Preparation of (S)—N—((R)-2-hydroxy-1-phenylethyl)-2-methyl-5-phenylpentanamide [17g(i)]

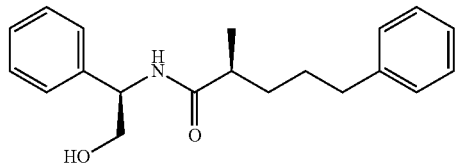 [SMILES: C[C@@H](CCCc1ccccc1)C(=O)N[C@@H](CO)c1ccccc1]

To the reaction mixture comprising 16g(i) prepared above was added R-(−)-2-phenylglycinol, and the mixture stirred overnight. The mixture was filtered and washed with THF and the filtrate was then concentrated under vacuum. The residue was purified by silica gel chromatography eluting with ethyl acetate-heptane (60:40 v/v). The solid obtained from the chromatography was crystallized from ethyl acetate-heptane to afford the title intermediate (198 mg, 42%) as a white solid; TLC $R_f$ 0.21 (solvent system: 60:40 v/v ethyl acetate-heptane; HPLC retention time 14.68 minutes, stationary phase: Gemini, 5μ C18 250×4.6 mm, ultraviolet wavelength of 210 nm, mobile phase: 1 mL/min, 60:40:0.1 methanol-water-acetic acid, 100% (S); MS (ESI⁺) m/z 312.2 (M+H)+, 334.1 (M+Na)⁺.

Scheme 7e, Steps H and I, and Scheme 8c: Preparation of (S)-(+)-dimethyl (3-methyl-2-oxo-6-phenylhexyl)phosphonate [13g(i)]

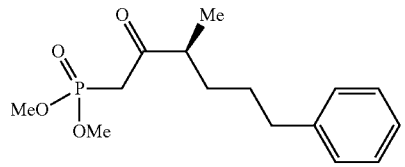 [SMILES: COP(=O)(CC(=O)[C@@H](C)CCCc1ccccc1)OC]

(S)-(+)-Dimethyl (3-methyl-2-oxo-6-phenylhexyl)phosphonate [13g(i)] is prepared in three steps from (S)—N—((R)-2-hydroxy-1-phenylethyl)-2-methyl-5-phenylpentanamide 17g(i) as in the sequence of steps (Scheme 7d, Steps D and E, and Scheme 8c) described above for the same process.

Preparation of(S)-(+)-dimethyl (3-methyl-2-oxo-5-phenylpentyl)phosphonate [13d(i)]

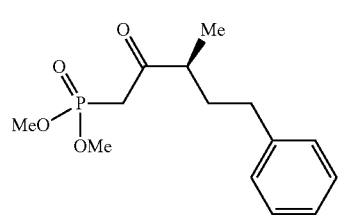 [SMILES: COP(=O)(CC(=O)[C@@H](C)CCc1ccccc1)OC]

(S)-Dimethyl (3-methyl-2-oxo-5-phenylpentyl)phosphonate [13d(i)] was prepared in the same manner as (S)-(+)-dimethyl (3-methyl-2-oxo-6-phenylhexyl)phosphonate [13g(i)] described above according to Schemes 7d and 8c, except that 1-bromo-2-phenylethane was used instead of 1-bromo-3-phenylpropane. The crude product was purified by silica gel chromatography eluting with ethyl acetate-heptane (50:50 v/v) to afford the title intermediate (460 mg) as a colorless oil; TLC $R_f$ 0.14 (solvent system: 50:50 v/v ethyl acetate: heptanes); MS (ESI$^+$) m/z 285.1 (M+H)+; $^1$H-NMR (CDCl$_3$) δ 7.30-7.24 (m, 2H), 7.21-7.14 (m, 3H), 3.76 (d, J=14.65 Hz, 3H), 3.76 (d, J=8.06 Hz, 3H), 3.16-3.03 (m, 2H), 2.77 (q, J=6.84 Hz, 1H), 2.64-2.56 (m, 2H), 2.03 (ddt, 1H), 1.16 (d, J=6.96 Hz, 3H); $[\alpha]^T_\lambda = \alpha/cl$, $[\alpha]^{21.9}_D = 0.052/(0.01998 \text{ g}/1.5 \text{ mL})(0.5) = +7.81°$ (c=1.33, CHCl$_3$).

Preparation of (S)-(+)-dimethyl (3-methyl-2-oxo-7-phenylheptyl)phosphonate

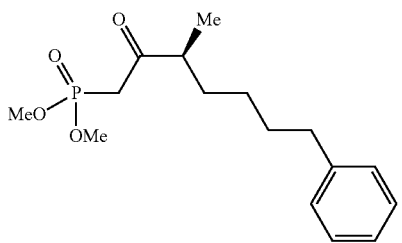 [SMILES: COP(=O)(CC(=O)[C@@H](C)CCCCc1ccccc1)OC]

(S)-Dimethyl (3-methyl-2-oxo-7-phenylheptyl)phosphonate [13(i)] was prepared in the same manner as (S)-(+)-dimethyl (3-methyl-2-oxo-6-phenylhexyl)phosphonate [13g (i)] described above according to Schemes 7d and 8c, except that 1-bromo-4-phenylbutane was used instead of 1-bromo-3-phenylpropane. The crude product was purified by silica gel chromatography eluting with ethyl acetate-heptane (50:50 v/v) to afford the title intermediate (2.84 g) as a colorless oil; TLC $R_f$ 0.54 (solvent system: 100 v ethyl acetate); MS (ESI$^+$) m/z 313.1 (M+H)$^+$; $^1$H-NMR (CDCl$_3$) δ 7.22-7.17 (m, 2H), 7.12-7.07 (m, 3H), 3.82-3.68 (m, 6H), 3.07 (s, 1H), 3.01 (s, 1H), 2.71-2.62 (m, 1H), 2.53 (t, J=7.69 Hz, 2H), 1.66-1.47 (m, 4H), 1.28-1.22 (m, 2H), 1.02 (d, J=6.96 Hz, 3H); $[\alpha]^T_\lambda = \alpha/cl$, $[\alpha]^{21.9}_D = 0.052/(0.01998 \text{ g}/1.5 \text{ mL})(0.5) = +7.81°$ (c=1.017, CHCl$_3$).

Preparation of (S)-(+)-dimethyl (3-methyl-2-oxo-8-phenyloctyl)phosphonate [13k(i)]

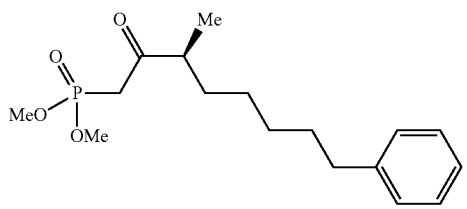 [SMILES: COP(=O)(CC(=O)[C@@H](C)CCCCCc1ccccc1)OC]

(S)-Dimethyl (3-methyl-2-oxo-8-phenyloctyl)phosphonate [13k(i)] was prepared in the same manner as (S)-(+)-dimethyl (3-methyl-2-oxo-6-phenylhexyl)phosphonate [13g (i)] described above according to Schemes 7d and 8c, except that 1-bromo-5-phenylpentane was used instead of 1-bromo-3-phenylpropane. The crude product was purified by silica gel chromatography eluting with ethyl acetate-heptane (50:50 v/v) to afford the title intermediate (1.06 g) as a colorless oil; TLC $R_f$ 0.22 (solvent system: 50:50 v/v ethyl acetate: heptanes); MS (ESI$^+$) m/z 327.1 (M+H)$^+$; $^1$H-NMR (CDCl$_3$) δ 7.27-7.24 (m, 2H), 7.19-7.14 (m, 3H), 3.79-3.76 (m, 6H), 3.13 (s, 1H), 3.08 (s, 1H), 2.76-2.68 (m, 1H), 2.61-2.56 (m, 2H), 1.68-1.56 (m, 4H), 1.35-1.28 (m, 4H), 1.09 (d, J=6.96 Hz, 3H); $[\alpha]^T_\lambda = \alpha/cl$, $[\alpha]^{21.9}_D = 0.074/(0.01534 \text{ g}/1.5 \text{ mL})(0.5) = +14.10°$ (c=1.02, CHCl$_3$).

Exemplary embodiments may be prepared utilizing a Horner-Emmons-Wadsworth-type procedure, according to the route described below in Schemes 9 and 10 by the coupling of an aldehyde intermediate, such as those for which their preparations are described and illustrated above (6a-f), with a β-keto phosphonate (13), such as those for which their preparations are described and illustrated above (13d-l), to provide an α,β-unsaturated ketone compound intermediate (20a-f). In some applications, the Horner-Emmons-Wadsworth reaction comprises contacting the aldehyde with the β-keto phosphonate in the presence of lithium chloride, a trialkylamine base, such as triethylamine or diisopropylethylamine, and a suitable solvent such as THF. A reduction of the C15-oxo group to the corresponding C15-hydroxyl group may be carried out with a reducing agent to provide C15α/β-OH stereoisomeric mixtures 21a-f (Scheme 9, Step B). In some applications, the reducing agent comprises sodium borohydride. In some applications, the reduction is a stereoselective reduction such as a Corey-Bakshi-Shibata (CBS) reduction. These mixtures may be separated into their C15-stereoisomer components 22a-f and 23a-f by HPLC (Step C) to provide the C15α-hydroxy (usually corresponding to the stereochemical nomenclature of C15S-hydroxy within the text of Examples) (22a-f) and C15β-hydroxy (usually corresponding to the nomenclature of C15R-hydroxy within the text of Examples) (23a-f) diastereomers. The ester intermediates 22a-f and 23a-f may subsequently be hydrolyzed to carboxylic acid embodiments 24a-f (Step D1) and 25a-f (Step D2), respectively. Organic β-keto phosphonates bearing a single chiral center, such as those shown below where, for example, B comprises

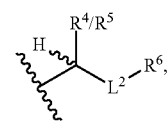

affords, when coupled with aldehydes like 6a-f in Scheme 9, Step A and then reduced as in Step B, a mixture (26a-f) comprising four diastereomers. The mixture may be separated into its isolated diastereomers 27a-f to 30a-f using preparatory HPLC as illustrated in Scheme 10, Step A. The corresponding carboxylic acids 31a-f to 34a-f may be obtained by basic aqueous hydrolysis of the esters using equimolar or excess (about 1-10 molar equivalents) hydroxide base, such as lithium hydroxide, potassium hydroxide, or sodium hydroxide, at about 1-3 M in hydroxide base. The basic aqueous hydrolysis reaction mixture may further comprise at least one solvent that is miscible with water, such as methanol, ethanol, THF, 1,4-dioxane, or DMF. Detailed procedures for preparing these compounds are described below.

Scheme 9
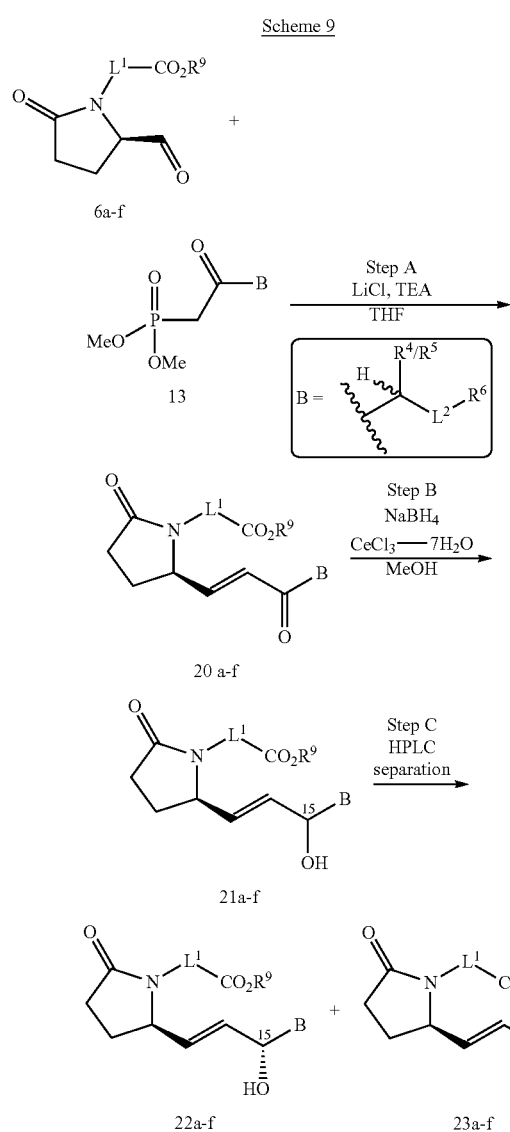
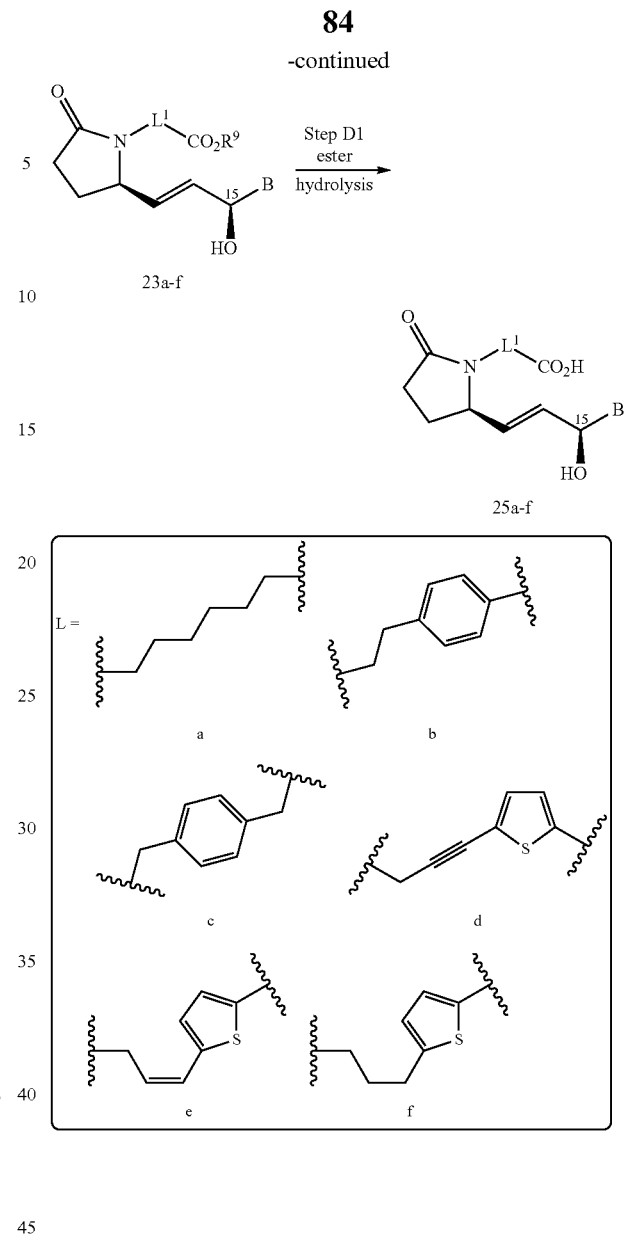
Scheme 10
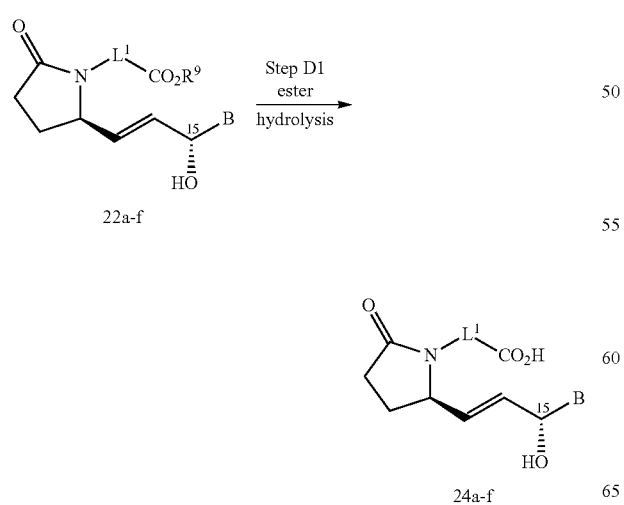

-continued

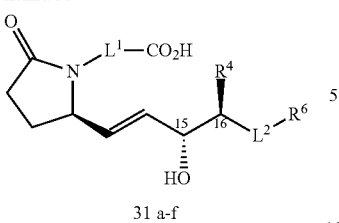

31 a-f

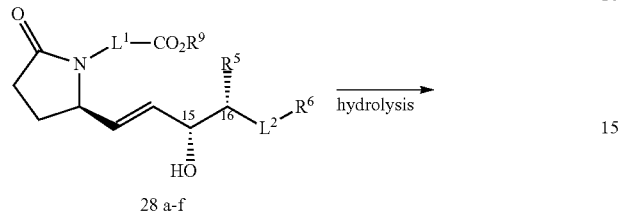

28 a-f

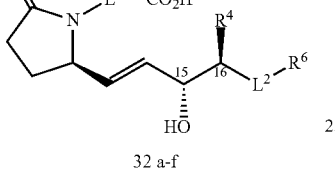

32 a-f

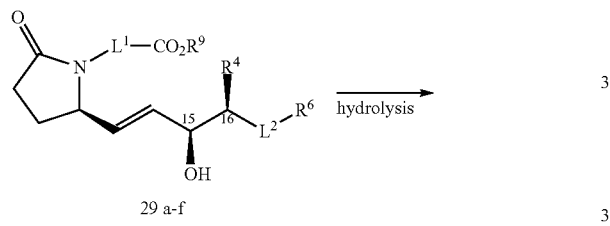

29 a-f

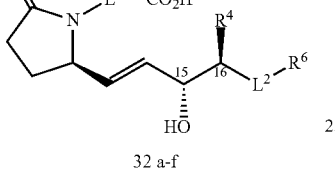

33 a-f

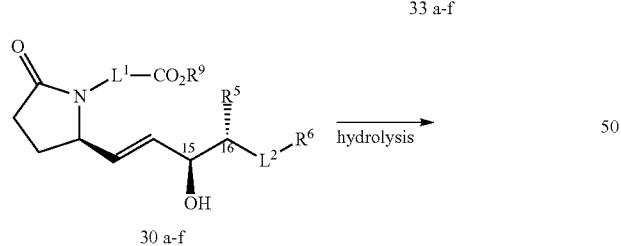

30 a-f

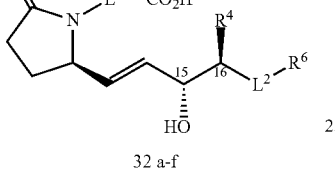

34 a-f

TABLE OF EXAMPLES

Examples 1A-1D

Scheme 9. Step A: Preparation of (R,E)-methyl 7-(2-oxo-5-(3-oxo-7-phenylhept-1-en-1-yl)pyrrolidin-1-yl)heptanoate

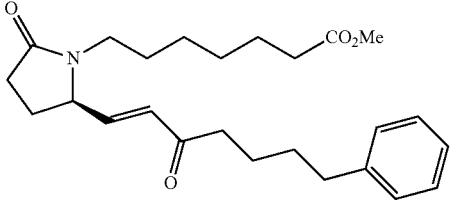 [SMILES: COC(=O)CCCCCCN1C(=O)CC[C@@H]1/C=C/C(=O)CCCCc1ccccc1]

To a stirring mixture consisting of (R)-methyl 7-(2-formyl-5-oxopyrrolidin-1yl)heptanoate (6a, 0.200 g, 0.78 mmol) and dimethyl (2-oxo-6-phenylhexyl)phosphonate (13f, 0.16 g, 0.56 mmol) in THF (20 mL) at 0° C. was added lithium chloride (83 mg, 1.96 mmol) and triethylamine (0.13 mL, 0.94 mmol). The reaction mixture was stirred at room temperature overnight. To the reaction mixture was added a saturated solution of ammonium chloride (30 mL) and organic material was extracted with ethyl acetate (100 mL). The organic layer was separated, washed with brine (50 mL), dried over sodium sulfate, filtered, and concentrated in vacuo. The residue was purified by silica gel chromatography eluting with ethyl acetate-heptane (7:3 v/v) to afford the title compound (182 mg, 56%); TLC $R_f$ 0.55 (solvent system: 75:25 v/v ethyl acetate-heptane).

Scheme 9, Steps B and C: Preparation of methyl 7-((R)-2-((S,E)-3-hydroxy-7-phenylhept-1-en-1-yl)-5-oxopyrrolidin-1-yl)heptanoate (Example 1A) and methyl 7-((R)-2-((R,E)-3-hydroxy-7-phenylhept-1-en-1-yl)-5-oxopyrrolidin-1-yl)heptanoate (Example 1B)

Example 1A

Example 1B

To a mixture consisting of (R,E)-methyl 7-(2-oxo-5-(3-oxo-7-phenylhept-1-en-1-yl)pyrrolidin-1-yl)heptanoate (182 mg, 0.47 mmol) in methanol (15 mL) at −40° C. was added cerium (III) chloride heptahydrate (176 mg, 0.47 mmol). The reaction mixture was cooled to −78° C. and stirred for one hour. To the reaction mixture was added sodium borohydride (36 mg, 0.94 mmol), and the reaction mixture stirred for two hours. Acetone was added and the mixture was stirred for 15 minutes at −78° C., after which time the mixture was allowed to warm to room temperature. To the room temperature reaction mixture was added a saturated aqueous solution of ammonium chloride (30 mL) and the organic material was extracted with ethyl acetate (100 mL). The organic layer was separated and washed with brine (50 mL), dried over sodium sulfate, filtered, and concentrated in vacuo. The residue was purified by silica gel chromatography eluting with ethyl acetate-heptanes (7:3 v/v) to afford the title compound (163 mg, 89%) as an epimeric mixture with regard to the configuration of the C15-OH position.

From the epimeric mixture (163 mg), the single epimers of Example 1A and Example 1B were isolated following separation by prep HPLC.

Gilson Semi-Prep instrument; ultraviolet detector at 210 nm; Luna 5μ Silica 250×21.2 mm column; mobile phase of heptanes-ethanol (92:8 v/v).

Example 1A (40 mg): a clear oil; HPLC retention time 23 min; TLC $R_f$ 0.36 (solvent system: 3:1 v/v ethyl acetate-heptane); MS (FIA/ESI$^+$) m/z 415.6 (M+1).

Example 1B (78 mg); a clear oil; HPLC retention time 18 min; TLC $R_f$ 0.42 (solvent system: 3:1 v/v ethyl acetate-heptane); MS (FIA/ESI$^+$) m/z 415.6 (M+1).

Scheme 9. Step D1: Preparation of 7-((R)-2-((S,E)-3-hydroxy-7-phenylhept-1-en-1-yl)-5-oxopyrrolidin-1-yl)heptanoic acid (Example 1C)

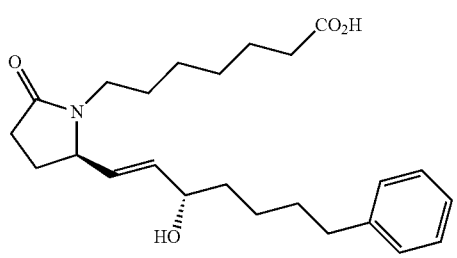 [SMILES: O=C(O)CCCCCCN1C(=O)CC[C@@H]1/C=C/[C@@H](O)CCCCc1ccccc1]

To a mixture consisting of methyl 7-((R)-2-((S,E)-3-hydroxy-7-phenylhept-1-en-1-yl)-5-oxopyrrolidin-1-yl)heptanoate (40 mg, 0.096 mmol, prepared as Example 1A above) in methanol (2 mL) was added 2 h sodium hydroxide (1 mL). The reaction mixture was stirred at room temperature for three hours. To the reaction mixture was added a solution of 5% potassium hydrogen sulfate-brine (1:1) to achieve an acidic pH, and the organic material was extracted with ethyl acetate. The organic phase was dried over sodium sulfate, filtered, and concentrated in vacuo. The residue was purified on silica gel eluting with ethyl acetate-acetic acid (100:0.4 v/v) to afford the title compound (33 mg, 85%) as a colorless oil; TLC $R_f$ 0.14 (solvent system: 100:1 v/v ethyl acetate-acetic acid); MS (ESI$^-$) m/z 400 (M−1); $^1$H NMR (methanol-d$_4$) δ 7.21-7.27 (m, 2H), 7.12-7.18 (m, 3H), 5.71 (dd, 1H) 5.48 (dd, 1H) 4.04-4.18 (m, 2H), 3.34-3.47 (m, 2H), 2.82-2.9 (m, 1H), 2.62 (t, 2H), 2.2-2.4 (m, 5H), 1.49-1.68 (m, 7H), 1.25-1.48 (m, 8H).

Scheme 9, Step D2: Preparation of 7-((R)-2-((R,E)-3-hydroxy-7-phenylhept-1-en-1-yl)-5-oxopyrrolidin-1-yl)heptanoic acid (Example 1D)

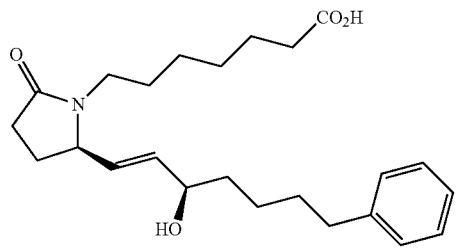 [SMILES: O=C(O)CCCCCCN1C(=O)CC[C@@H]1/C=C/[C@H](O)CCCCc1ccccc1]

7-((R)-2-((R,E)-3-Hydroxy-7-phenylhept-1-en-1-yl)-5-oxopyrrolidin-1-yl)heptanoic acid was prepared from the corresponding carboxylic ester, Example 1B, in the same manner as its epimer 7-((R)-2-((S,E)-3-hydroxy-7-phenylhept-1-en-1-yl)-5-oxopyrrolidin-1-yl)heptanoic acid, Example 1C, to obtain 69 mg (75%) of a clear oil; TLC $R_f$ 0.20 (solvent system: 100:1 v/v ethyl acetate-acetic acid); MS (ESI$^-$) m/z 400 (M−1).

Example 2A-2F

Scheme 9, Step A: Preparation of methyl 7-((2R)-2-((E)-4-methyl-3-oxo-7-phenylhept-1-en-1-yl)-5-oxopyrrolidin-1-yl)heptanoate

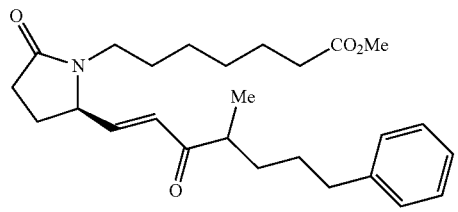 [SMILES: COC(=O)CCCCCCN1C(=O)CC[C@@H]1/C=C/C(=O)C(C)CCCc1ccccc1]

Methyl 7-((2R)-2-((E)-4-methyl-3-oxo-7-phenylhept-1-en-1-yl)-5-oxopyrrolidin-1-yl)heptanoate (182 mg, 56%) was prepared in the same manner as (R,E)-methyl 7-(2-oxo-5-(3-oxo-7-phenylhept-1-en-1-yl)pyrrolidin-1-yl)heptanoate as described above except that (±)-dimethyl (3-methyl-2-oxo-6-phenylhexyl)phosphonate [13g/h(i)] was used instead of dimethyl (2-oxo-6-phenylhexyl)phosphonate (13f). TLC $R_f$ 0.55 (solvent system: 75:25 v/v ethyl acetate-heptane).

Scheme 9, Steps B, and C: Preparation of methyl 7-((2R)-2-((3S,E)-3-hydroxy-4-methyl-7-phenylhept-1-en-1-yl)-5-oxopyrrolidin-1-yl)heptanoate (Example 2A) and methyl 7-((2R)-2-((3R,E)-3-hydroxy-4-methyl-7-phenylhept-1-en-1-yl)-5-oxopyrrolidin-1-yl)heptanoate (Example 2B)

Example 2A

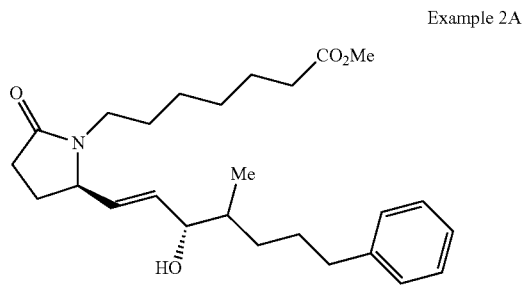

Example 2B

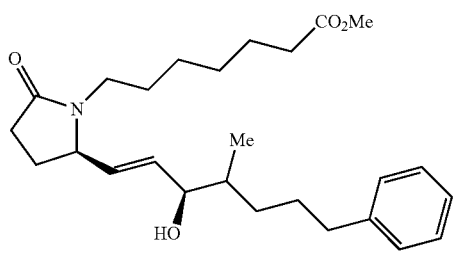

The set of four diastereomers of methyl 7-((2R)-2-((E)-3-hydroxy-4-methyl-7-phenylhept-1-en-1-yl)-5-oxopyrrolidin-1-yl)heptanoate was prepared from methyl 7-((2R)-2-((E)-4-methyl-3-oxo-7-phenylhept-1-en-1-yl)-5-oxopyrrolidin-1-yl)heptanoate in the same manner as described in Example 1A-1D above utilizing cerium (ITT) chloride heptahydrate and sodium borohydride.

From the diastereomeric mixture of four isomers, the epimeric mixtures of Example 2A and Example 2B were isolated following separation by prep HPLC.

Gilson Prep instrument; ultraviolet detector at 210 nm; Luna Silica 5μ 250 mm×21.2 mm column; mobile phase of heptane-ethanol (92:8 v/v), 21.2 mL/min.

Example 2A; a clear oil; HPLC retention time 18 min; TLC $R_f$ 0.38 (solvent system: 4:1 v/v ethyl acetate-heptane); MS (ESI+) m/z 430.2 (M+1).

Example 2B; a clear oil; HPLC retention time 14.5 min; TLC $R_f$ 0.46 (solvent system: 4:1 v/v ethyl acetate-heptane); MS (ESI+) m/z 430.2 (M+1).

Scheme 9, Step D1: Preparation of 7-((2R)-2-((3S,E)-3-hydroxy-4-methyl-7-phenylhept-1-en-1-yl)-5-oxopyrrolidin-1-yl)heptanoic acid (Example 2C)

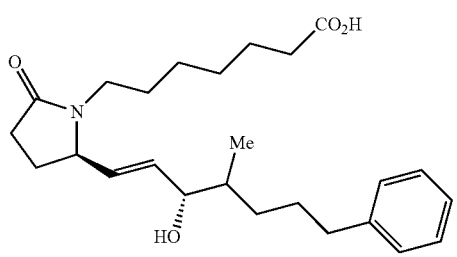 [SMILES: CC(CCCc1ccccc1)[C@H](O)/C=C/[C@H]1CCC(=O)N1CCCCCCC(=O)O]

7-((2R)-2-((3S,E)-3-Hydroxy-4-methyl-7-phenylhept-1-en-1-yl)-5-oxopyrrolidin-1-yl)heptanoic acid was prepared from the corresponding carboxylic ester, Example 2A, in the same manner as 7-((R)-2-((S,E)-3-hydroxy-7-phenylhept-1-en-1-yl)-5-oxopyrrolidin-1-yl)heptanoic acid, Example 1C, to obtain 49 mg (100%) of a clear oil; TLC $R_f$ 0.22 (solvent system: 85:15:1 v/v ethyl acetate-heptane-acetic acid); MS (ESI−) m/z 414.2 (M−1); $^1$H-NMR (CDCl$_3$) δ 7.18-7.35 (m, 5H), 5.4-5.7 (dd, 2H), 4.1-4.15 (m, 1H), 0.83-2.95 (m, 26H).

Scheme 9, Step D2: Preparation of 7-((2R)-2-((3R,E)-3-hydroxy-4-methyl-7-phenylhept-1-en-1-yl)-5-oxopyrrolidin-1-yl)heptanoic acid (Example 2D)

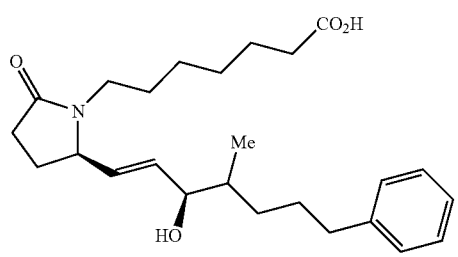 [SMILES: CC(CCCc1ccccc1)[C@@H](O)/C=C/[C@H]1CCC(=O)N1CCCCCCC(=O)O]

7-((2R)-2-((3R,E)-3-Hydroxy-4-methyl-7-phenylhept-1-en-1-yl)-5-oxopyrrolidin-1-yl)heptanoic acid was prepared from the corresponding carboxylic ester, Example 2B, in the same manner as its epimer 7-((2R)-2-((3S,E)-3-hydroxy-4-methyl-7-phenylhept-1-en-1-yl)-5-oxopyrrolidin-1-yl)heptanoic acid (Example 2C), to obtain 134 mg (100%) of a clear oil; TLC $R_f$ 0.32 (solvent system: 85:15:1 v/v ethyl acetate-heptane-acetic acid); $^1$H-NMR (CD$_3$OD) δ 7.26-7.10 (m, 5H), 5.71 (td, 1H, J=5.86, 15.38 Hz), 5.52-5.44 (m, 1H), 4.18-4.12 (m, 1H), 3.98-3.94 (m, 1H), 3.46 (td, 1H, J=7.69, 13.55 Hz), 2.91 (ddd, J=5.49, 8.15, 13.46 Hz), 2.66-2.53 (m, 2H), 2.43-2.15 (m, 6H), 1.73-1.44 (m, 9H), 1.39-1.23 (m, 4H), 1.18-1.07 (m, 1H), 0.89 (dd, 3H, J=6.77, 10.07 Hz); MS (ESI−) m/z 414.2 (M−1).

Preparation of 7-((R)-2-((3S,4S,E)-3-hydroxy-4-methyl-7-phenylhept-1-en-1-yl)-5-oxopyrrolidin-1-yl)heptanoic acid (Example 2E)

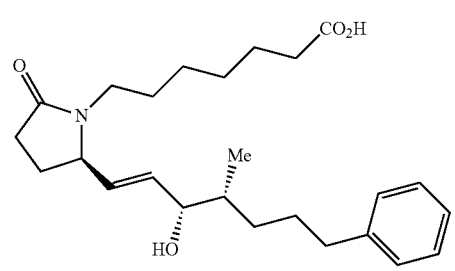 [SMILES: C[C@H](CCCc1ccccc1)[C@H](O)/C=C/[C@H]1CCC(=O)N1CCCCCCC(=O)O]

The title compound is prepared from (R)-methyl 7-(2-formyl-5-oxopyrrolidin-1-yl)heptanoate (6a) with the same sequence of chemical steps used to prepare Example 1A from (6a), except that dimethyl (S)-(+)-(3-methyl-2-oxo-6-phenylhexyl)phosphonate [13g(i)] is used instead of dimethyl (2-oxo-6-phenylhexyl)phosphonate (13f) in the Horner-Wadsworth-Emmons step.

Preparation of 7-((R)-2-((3S,4R,E)-3-hydroxy-4-methyl-7-phenylhept-1-en-1-yl)-5-oxopyrrolidin-1-yl)heptanoic acid (Example 2F)

The title compound is prepared from (R)-methyl 7-(2-formyl-5-oxopyrrolidin-1-yl)heptanoate (6a) in the manner used to prepare Example 2E from (6a), except that dimethyl (R)-(−)-(3-methyl-2-oxo-6-phenylhexyl)phosphonate [13h(i)] is used instead of dimethyl (S)-(+)-(3-methyl-2-oxo-6-phenylhexyl)phosphonate [13g(i)] in the Horner-Wadsworth-Emmons step.

Example 3A-3D

Scheme 9. Steps A, B, and C: Preparation of methyl 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylate (3A) and methyl 5-(3-((2R)-2-((3R,E)-3-hydroxy-4-methyl-7-phenylhept-1-en-1-yl)-5-oxopyrrolidin-1-yl)prop-1-yn-1-yl)thiophene-2-carboxylate (3B)

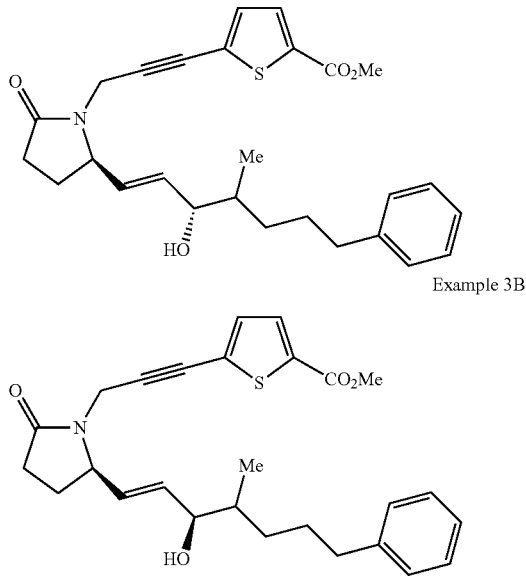

Example 3A

Example 3B

The set of four diastereomers of methyl 5-(3-((2R)-2-((E)-3-hydroxy-4-methyl-7-phenylhept-1-en-1-yl)-5-oxopyrrolidin-1-yl)prop-1-yn-1-yl)thiophene-2-carboxylate was prepared in the same manner as described in Example 2A-2D and illustrated in Scheme 9, Step A and B, except that (R)-methyl 5-(3-(2-formyl-5-oxopyrrolidin-1-yl)prop-1-yn-1-yl)thiophene-2-carboxylate (6d) was used instead of (R)-methyl 7-(2-formyl-5-oxopyrrolidin-1yl)heptanoate (6a) in Step A.

From the diastereomeric mixture of four isomers (85 mg), the epimeric mixtures of Example 3A and Example 3B were isolated following separation by prep HPLC.

Agilent Semi-Prep instrument; ultraviolet detector at 205 nm; Luna Silica 5µ 250 mm×10 mm column; mobile phase of heptane-ethanol (90:10 v/v).

Example 3A (17.1 mg); a clear oil; prep HPLC retention time 17.1-19.5 minutes; $^1$H-NMR (CDCl$_3$) δ 7.6 (d, 1H), 7.3-7.25 (m, 2H), 7.2-7.15 (m, 3H), 7.1 (d, 1H), 5.85-5.75 (m, 1H), 5.55-5.5 (m, 1H), 4.7-4.65 (m, 1H), 4.25-4.2 (m, 1H), 4.1-4.0 (m, 1H), 3.87 (s, 3H) 3.85-3.75 (m, 1H), 2.6 (t, 2H), 2.45-2.25 (m, 3H), 1.75-1.5 (m, 4H), 1.2-1.1 (m, 2H), 0.91 (d, 3H); MS (ESI$^+$) m/z 466.1 (M+1), 488.0 (M+Na).

Example 3B (52 mg); a clear oil; prep HPLC retention time 13.8-16.9 minutes; $^1$H-NMR (CDCl$_1$) δ 7.6 (d, 1H), 7.3-7.25 (m, 2H), 7.2-7.15 (m, 3H), 7.1 (d, 1H), 5.85-5.75 (m, 1H), 5.55-5.5 (m, 1H), 4.7-4.65 (m, 1H), 4.25-4.2 (m, 1H), 4.1-4.0 (m, 1H), 3.87 (s, 3H) 3.85-3.75 (m, 1H), 2.6 (t, 2H), 2.45-2.25 (m, 3H), 1.75-1.5 (m, 4H), 1.2-1.1 (m, 2H), 0.91 (d, 3H); MS (ESI$^+$) m/z 466.1 (M+1), 488.0 (M+Na).

Scheme 9. Step D1: Preparation of 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylic acid Example 3C

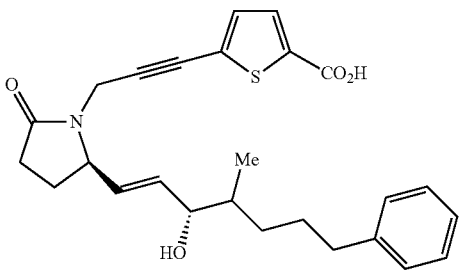 [SMILES: CC(CCCc1ccccc1)[C@H](O)/C=C/[C@H]1CCC(=O)N1CC#Cc1ccc(C(=O)O)s1]

5-(3-((2R)-2-((3S,E)-3-Hydroxy-4-methyl-7-phenylhept-1-en-1-yl)-5-oxopyrrolidin-1-yl)prop-1-yn-1-yl)thiophene-2-carboxylic acid was prepared from the corresponding carboxylic ester, Example 3A, in the same manner as 7-((R)-2-((S,E)-3-hydroxy-7-phenylhept-1-en-1-yl)-5-oxopyrrolidin-1-yl)heptanoic acid, Example 1C, to obtain 13.8 mg; TLC R$_f$ 0.40 (solvent system: 96:4:1 v/v dichloromethane-methanol-acetic acid); $^1$H-NMR (CDCl$_3$) δ 7.6 (d, 1H), 7.25-7.15 (m, 2H), 7.1-7.05 (m, 3H), 7.05 (d, 1H), 5.8-5.7 (m, 1H), 5.5-5.4 (m, 1H), 4.65-4.55 (m, 1H), 4.25-4.15 (m, 1H), 4.05-3.95 (m, 1H), 3.8-3.7 (m, 1H), 2.5 (t, 2H), 2.45-2.3 (m, 2H), 2.3-2.15 (m, 1H), 1.75-1.4 (m, 4H), 1.2-1.1 (m, 2H), 0.85 (d, 1.5H) 0.83 (d, 1.5H); MS ((ESI$^+$) m/z 452.1 (M+1) (ESI$^-$) m/z 450.1 (M−1).

Scheme 9, Step D2: Preparation of 5-(3-((2R)-2-((3R,E)-3-hydroxy-4-methyl-7-phenylhept-1-en-1-yl)-5-oxopyrrolidin-1-yl)prop-1-yn-1-yl)thiophene-2-carboxylic acid (Example 3D)

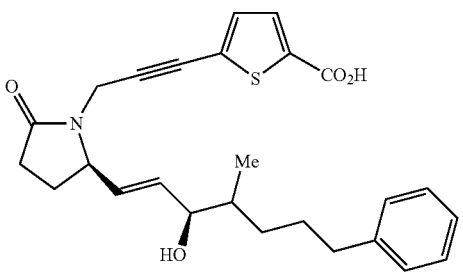 [SMILES: CC(CCCc1ccccc1)[C@@H](O)/C=C/[C@H]1CCC(=O)N1CC#Cc1ccc(C(=O)O)s1]

5-(3-((2R)-2-((3R,E)-3-Hydroxy-4-methyl-7-phenylhept-1-en-1-yl)-5-oxopyrrolidin-1-yl)prop-1-yn-1-yl)thiophene-2-carboxylic acid was prepared from the corresponding carboxylic ester, Example 3B, in the same manner as its epimer 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylic acid (Example 3C), to obtain 40.4 mg; TLC $R_f$ 0.40 (solvent system: 96:4:1 v/v dichloromethane-methanol-acetic acid); $^1$H-NMR (CDCl$_3$) δ 7.6 (d, 1H), 7.25-7.15 (m, 2H), 7.1-7.05 (m, 3H), 7.05 (d, 1H), 5.8-5.7 (m, 1H), 5.5-5.4 (m, 1H), 4.65-4.55 (m, 1H), 4.25-4.15 (m, 1H), 4.05-3.95 (m, 1H), 3.8-3.7 (m, 1H), 2.5 (t, 2H), 2.45-2.3 (m, 2H), 2.3-2.15 (m, 1H), 1.75-1.4 (m, 4H), 1.2-1.1 (m, 2H), 0.85 (d, 1.5H) 0.83 (d, 1.5H); MS ((ESI+) m/z 452.1 (M+1) (ESI−) m/z 450.1 (M−1).

Examples 4A-4F

Scheme 9, Steps A, B, and C: Preparation of methyl 5-(3-((2R)-2-((3S,E)-3-hydroxy-4-methyl-7-phenylhept-1-en-1-yl)-5-oxopyrrolidin-1-yl)propyl)thiophene-2-carboxylate (Example 4A) and methyl 5-(3-((2R)-2-((3R,E)-3-hydroxy-4-methyl-7-phenylhept-1-en-1-yl)-5-oxopyrrolidin-1-yl)propyl)thiophene-2-carboxylate (Example 4B)

Example 4A

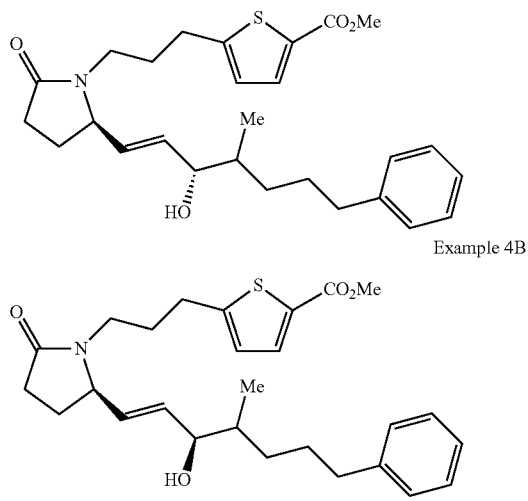

Example 4B

The set of four diastereomers of methyl 5-(3-((2R)-2-((E)-3-hydroxy-4-methyl-7-phenylhept-1-en-1-yl)-5-oxopyrrolidin-1-yl)propyl)thiophene-2-carboxylate was prepared in the same manner as described in Example 2A-2D and illustrated in Scheme 9, Step A and B, except that (R)-methyl 5-(3-(2-formyl-5-oxopyrrolidin-1-yl)propyl)thiophene-2-carboxylate (6f) was used instead of (R)-methyl 7-(2-formyl-5-oxopyrrolidin-1 yl)heptanoate (6a) in Step A.

From the diastereomeric mixture of four isomers, the epimeric mixtures of Example 4A and Example 4B were isolated following separation by prep HPLC.

Agilent Semi-Prep instrument; ultraviolet detector at 205 nm; Luna Silica 5μ 250 mm×10 mm column; mobile phase of heptane-ethanol (90:10 v/v).

Example 4A (9.6 mg); a clear oil; prep HPLC retention time 19.0-21.5 minutes; $^1$H-NMR (CDCl$_3$) δ 7.6 (d, 1H), 7.3-7.2 (m, 2H), 7.2-7.1 (m, 3H), 6.8 (d, 1H), 5.65 (dd, 1H), 5.5-5.45 (m, 1H), 4.05-4.0 (m, 2H), 3.85 (s, 3H), 3.6-3.55 (1H, m), 3.0-2.95 (m, 1H), 2.8 (t, 2H), 2.6-2.5 (m, 2H), 2.5-2.3 (m, 2H), 2.3-2.1 (m, 1H), 1.9-1.8 (m, 2H), 1.7-1.4 (m, 5H), 1.2-1.1 (m, 1H), 0.86 (d, 1.5H), 0.85 (d, 1.5H); MS (ESI$^+$) m/z 492.1 (M+Na)

Example 4B (32.6 mg); a clear oil; prep HPLC retention time 15.6-18.0 minutes; $^1$H-NMR (CDCl$_3$) δ 7.6 (d, 1H), 7.3-7.2 (m, 2H), 7.2-7.1 (m, 3H), 6.8 (d, 1H), 5.65 (dd, 1H), 5.5-5.45 (m, 1H), 4.05-4.0 (m, 2H), 3.85 (s, 3H), 3.6-3.55 (1H, m), 3.0-2.95 (m, 1H), 2.8 (t, 2H), 2.6-2.5 (m, 2H), 2.5-2.3 (m, 2H), 2.3-2.1 (m, 1H), 1.9-1.8 (m, 2H), 1.7-1.4 (m, 5H), 1.2-1.1 (m, 1H), 0.86 (d, 1.5H), 0.85 (d, 1.5H); MS (ESI$^+$) m/z 492.1 (M+Na)

Scheme 9. Step D1: 5-(3-((2R)-2-((3S,E)-3-hydroxy-4-methyl-7-phenylhept-1-en-1-yl)-5-oxopyrrolidin-1-yl)propyl)thiophene-2-carboxylic acid (Example 4C)

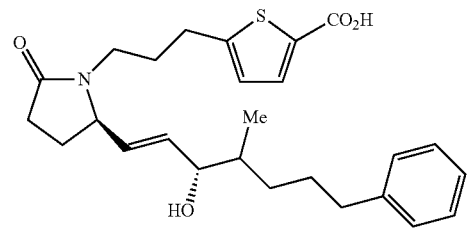

5-(3-((2R)-2-((3S,E)-3-Hydroxy-4-methyl-7-phenylhept-1-en-1-yl)-5-oxopyrrolidin-1-yl)propyl)thiophene-2-carboxylic acid was prepared from the corresponding carboxylic ester, Example 4A, in the same manner as 7-((R)-2-((S,E)-3-hydroxy-7-phenylhept-1-en-1-yl)-5-oxopyrrolidin-1-yl)heptanoic acid, Example 1C, to obtain 7.8 mg as a colorless oil; TLC $R_f$ 0.40 (solvent system: 96:4:1 v/v dichloromethane-methanol-acetic acid); $^1$H-NMR (CDCl$_3$) δ 7.6 (d, 1H), 7.3-7.2 (m, 2H), 7.2-7.1 (m, 3H), 6.75 (d, 1H), 5.6 (dd, 1H), 5.45-5.35 (m, 1H), 4.1-3.9 (m, 2H), 3.55-3.45 (1H, m), 2.95-2.9 (m, 1H), 2.75 (t, 2H), 2.6-2.45 (m, 2H), 2.45-2.3 (m, 2H), 2.3-2.1 (m, 1H), 1.85-1.75 (m, 2H), 1.65-1.35 (m, 5H), 1.2-1.0 (m, 1H), 0.80 (d, 1.5H), 0.79 (d, 1.5H); MS (ESI$^-$) m/z 454.1 (M−1).

Scheme 9, Step D2: 5-(3-((2R)-2-((3R,E)-3-hydroxy-4-methyl-7-phenylhept-1-en-1-yl)-5-oxopyrrolidin-1-yl)propyl)thiophene-2-carboxylic acid (Example 4D)

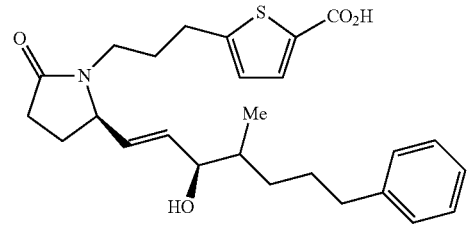 [SMILES: CC(CCCc1ccccc1)[C@@H](O)/C=C/[C@H]1CCC(=O)N1CCCc1ccc(C(=O)O)s1]

5-(3-((2R)-2-((3R,E)-3-Hydroxy-4-methyl-7-phenylhept-1-en-1-yl)-5-oxopyrrolidin-1-yl)propyl)thiophene-2-carboxylic acid was prepared from the corresponding carboxylic ester, Example 4B, in the same manner as its epimer 5-(3-((2R)-2-((3S,E)-3-hydroxy-4-methyl-7-phenylhept-1-en-1-yl)-5-oxopyrrolidin-1-yl)propyl)thiophene-2-carboxylic acid (Example 4C), to obtain 26.8 mg as a colorless oil; TLC $R_f$ 0.40 (solvent system: 96:4:1 v/v dichloromethane-methanol-acetic acid); $^1$H-NMR (CDCl$_3$) δ 7.6 (d, 1H), 7.3-7.2 (m, 2H), 7.2-7.1 (m, 3H), 6.75 (d, 1H), 5.6 (dd, 1H), 5.45-5.35 (m, 1H), 4.1-3.9 (m, 2H), 3.55-3.45 (1H, m), 2.95-2.9 (m, 1H), 2.75 (t, 2H), 2.6-2.45 (m, 2H), 2.45-2.3 (m, 2H), 2.3-2.1 (m, 1H), 1.85-1.75 (m, 2H), 1.65-1.35 (m, 5H), 1.2-1.0 (m, 1H), 0.80 (d, 1.5H), 0.79 (d, 1.5H); MS (ESI⁻) m/z 454.1 (M−1).

5-(3-((R)-2-((3S,4S,E)-3-hydroxy-4-methyl-7-phenylhept-1-en-1-yl)-5-oxopyrrolidin-1-yl)propyl)thiophene-2-carboxylic acid (Example 4E)

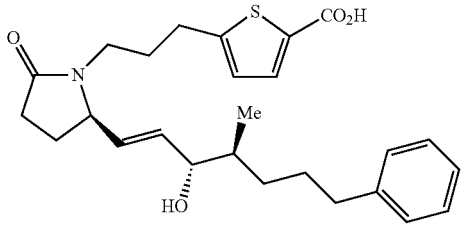 [SMILES: C[C@@H](CCCc1ccccc1)[C@H](O)/C=C/[C@H]1CCC(=O)N1CCCc1ccc(C(=O)O)s1]

The title compound is prepared from (R)-methyl 5-(3-(2-(formyl-5-oxopyrrolidin-1-yl)propyl)thiophene-2-carboxylate (61) with the same sequence of chemical steps used to prepare Example 1E from (6a).

5-(3-((R)-2-((3S,4R,E)-3-hydroxy-4-methyl-7-phenylhept-1-en-1-yl)-5-oxopyrrolidin-1-yl)propyl)thiophene-2-carboxylic acid (Example 4F)

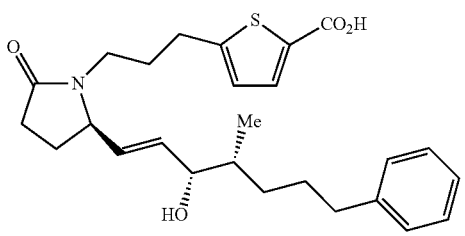 [SMILES: C[C@H](CCCc1ccccc1)[C@H](O)/C=C/[C@H]1CCC(=O)N1CCCc1ccc(C(=O)O)s1]

The title compound is prepared from (R)-methyl 5-(3-(2-(formyl-5-oxopyrrolidin-1-yl)propyl)thiophene-2-carboxylate (6) with the same sequence of chemical steps used to prepare Example 1F from (6a).

Examples 5A-5B

Preparation of 5-(3-((R)-2-((3S,4S,E)-3-hydroxy-4-methyl-6-phenylhex-1-en-1-yl)-5-oxopyrrolidin-1-yl)propyl)thiophene-2-carboxylic acid (Example 5A) and 5-(3-((R)-2-((3R,4S,E)-3-hydroxy-4-methyl-6-phenylhex-1-en-1-yl)-5-oxopyrrolidin-1-yl)propyl)thiophene-2-carboxylic acid (Example 5B)

Example 5A

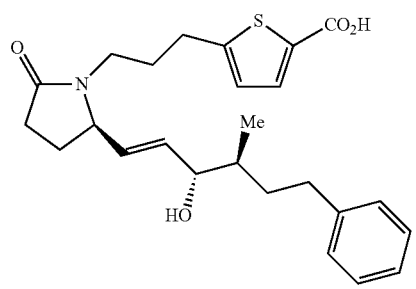

Example 5B

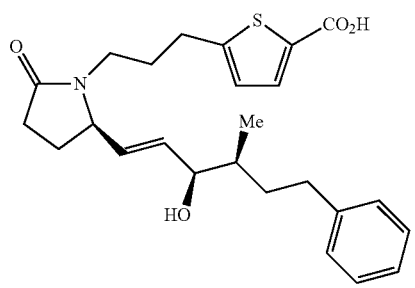

The title compounds are prepared according to the methods used to prepare Examples 1C and 1D, except aldehyde (60) is used instead of (6a) and β-keto phosphonate [13d(i)] is used instead of (13f).

Examples 5C-5D

Preparation of 5-(3-((R)-2-((3S,4R,E)-3-hydroxy-4-methyl-6-phenylhex-1-en-1-yl)-5-oxopyrrolidin-1-yl)propyl)thiophene-2-carboxylic acid (Example 5C) and 5-(3-((R)-2-((3R,4R,E)-3-hydroxy-4-methyl-6-phenylhex-1-en-1-yl)-5-oxopyrrolidin-1-yl)propyl)thiophene-2-carboxylic acid (Example 5D)

Example 5C

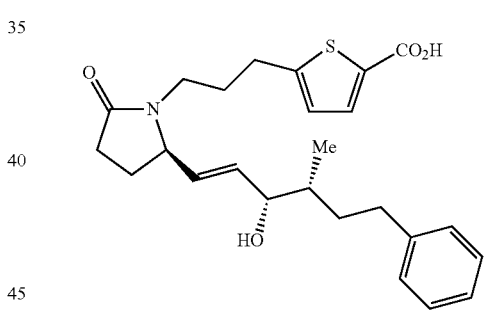

Example 5D

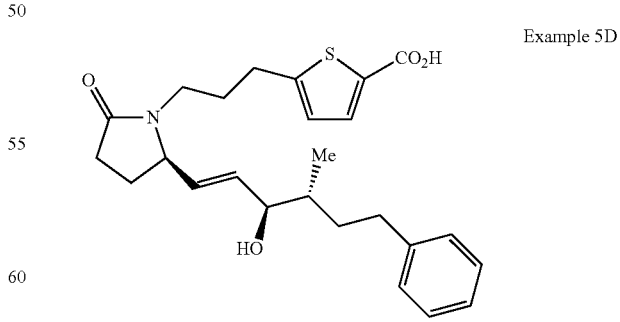

The title compounds are prepared according to the methods used to prepare Examples 1C and 1D, except aldehyde (61) is used instead of (6a) and β-keto phosphonate [13e(i)] is used instead of (13f).

Examples 6A-6B

Preparation of 5-(3-((R)-2-((3S,4S,E)-3-hydroxy-4-methyl-8-phenyloct-1-en-1-yl)-5-oxopyrrolidin-1-yl)propyl)thiophene-2-carboxylic acid (Example 6A) and 5-(3-((R)-2-((3R,4S,E)-3-hydroxy-4-methyl-8-phenyloct-1-en-1-yl)-5-oxopyrrolidin-1-yl)propyl)thiophene-2-carboxylic acid (Example 6B)

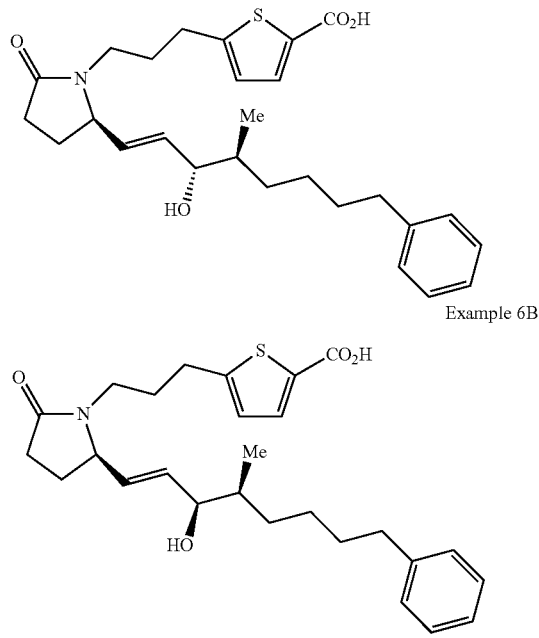

Example 6A

Example 6B

The title compounds are prepared according to the methods used to prepare Examples 1C and 1D, except aldehyde (6l) is used instead of (6a) and β-keto phosphonate [13i(i)] is used instead of (13f).

Examples 6C-6D

Preparation of 5-(3-((R)-2-((3S,4R,E)-3-hydroxy-4-methyl-8-phenyloct-1-en-1-yl)-5-oxopyrrolidin-1-yl)propyl)thiophene-2-carboxylic acid (Example 6C) and 5-(3-((R)-2-((3R,4R,E)-3-hydroxy-4-methyl-8-phenyloct-1-en-1-yl)-5-oxopyrrolidin-1-yl)propyl)thiophene-2-carboxylic acid (Example 6D)

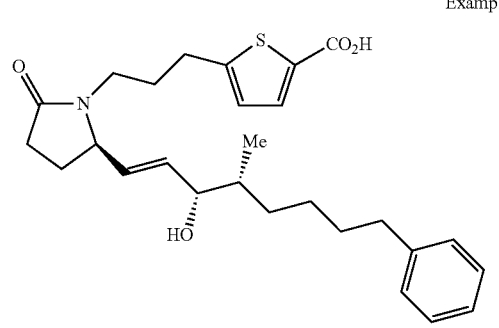

Example 6C

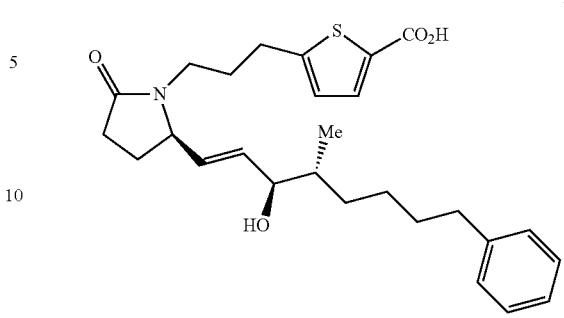

Example 6D

The title compounds are prepared according to the methods used to prepare Examples 1C and 1D, except aldehyde (6f) is used instead of (6a) and β-keto phosphonate [13j(i)] is used instead of (13f).

Examples 7A-7B

Preparation of 5-(3-((R)-2-((3S,4S,E)-3-hydroxy-4-methyl-9-phenylnon-1-en-1-yl)-5-oxopyrrolidin-1-yl)propyl)thiophene-2-carboxylic acid (Example 7A) and 5-(3-((R)-2-((3R,4S,E)-3-hydroxy-4-methyl-9-phenylnon-1-en-1-yl)-5-oxopyrrolidin-1-yl)propyl)thiophene-2-carboxylic acid (Example 7B)

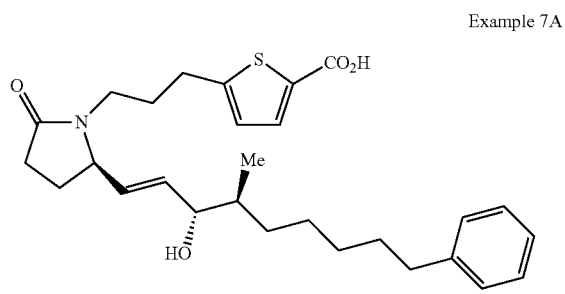

Example 7A

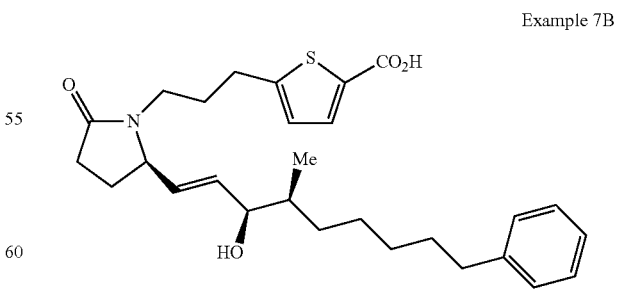

Example 7B

The title compounds are prepared according to the methods used to prepare Examples 1C and 1D, except aldehyde (6f) is used instead of (6a) and β-keto phosphonate [13k(i)] is used instead of (13f).

Examples 7C-7D

Preparation of 5-(3-((R)-2-((3S,4R,E)-3-hydroxy-4-methyl-9-phenyloctnon-1-en-1-yl)-5-oxopyrrolidin-1-yl)propyl)thiophene-2-carboxylic acid (Example 7C) and 5-(3-((R)-2-((3R,4R,E)-3-hydroxy-4-methyl-9-phenylnon-1-en-1-yl)-5-oxopyrrolidin-1-yl)propyl)thiophene-2-carboxylic acid (Example 7D)

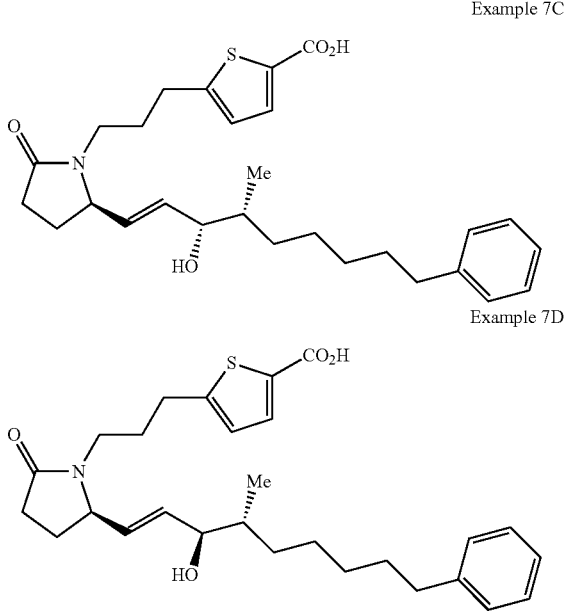

Example 7C

Example 7D

The title compounds are prepared according to the methods used to prepare Examples 1C and 1D, except aldehyde (6f) is used instead of (6a) and fi-keto phosphonate [13i(i)] is used instead of (13f).

Example 8

Radioligand Binding Assay for the Evaluation of the Affinity of Compounds for the Agonist Site of the Human Prostanoid $EP_4$ Receptor in Transfected HEK-293 Cells Assay Volume and Format:
200 μl in 96-well plate Cell membrane homogenates (20 μg protein) are incubated for 120 min at 22° C. with 0.5 nM [$^3$H]$PGE_2$ in the absence or presence of the test compound in a buffer containing 10 mM MES/KOH (pH 6.0), 10 mM $MgCl_2$ and 1 mM EDTA.

Nonspecific binding is determined in the presence of 10 μM $PGE_2$.

Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The standard reference compound is $PGE_2$, which is tested in each experiment at several concentrations to obtain a competition curve from which its $IC_{50}$ is calculated.

Example 9

Functional Cellular Assays (STEP Plate Format)

Both SEAP activity assay and cAMP level assay for $EP_2$ or $EP_4$ agonist were performed on $EP_2/EP_4$ STEP (Surface Transfection and Expression Protocol) plates (from Originus®) which are coated with both rat $EP_2$ or $EP_4$ receptor and secreted alkaline phosphatase (SEAP) reporter constructs. Cells grown on the STEP complex will express $EP_2$ or $EP_4$ at the cell surface. Binding of agonists to $EP_2$ or $EP_4$ initiates a signal transduction cascade results in a transient increase in cAMP and an increase in expression of SEAP which is secreted into the cell culture media. cAMP levels were then measured with an ELISA assay and SEAP activity was measured with a luminescence-based alkaline phosphatase substrate.

Procedure of SEAP Activity Assay for $EP_2/EP_4$ Agonist

1. Seed cells on an $EP_2$ or $EP_4$ STEP plate at a density of 40,000-80,000 cells/well in 200 μl of reduced serum medium containing 0.5% FBS. Place the plate in a 37° C. incubator with 5% $CO_2$ and incubate overnight.

2. After 16-18 hours of incubation, aspirate the culture media from each well.

3. Add 200 μl of culture medium containing different concentration of test compounds to the assigned wells. For each test compound, at least 8 concentrations starting at highest 10 μM and lowest 0.01 pM were tested. In addition each concentration had triplicates. A $PGE_2$ curve (concentrations from lowest to highest, 0 pM, 0.384 pM, 1.92 pM, 9.6 pM, 48 pM, 240 pM, 1200 pM, and 6000 pM) was always run in parallel with test compounds.

4. After 6-8 hours of stimulation with test compounds and $PGE_2$, 10 μl of culture media from each well was transferred to a corresponding well of a 96-well solid black plate. Cover the plate with the lid.

5. Inactivate the endogenous alkaline phosphatase by heating the samples at 65° C. for 30 minutes.

6. Add 50 μl of luminescence-based alkaline phosphatase substrate (Michigan Diagnostics, LLC, Cat#SAP450101) to each well.

7. Measure the SEAP activity by reading the luminescent signal from each well.

8. The data was analyzed and the $EC_{50}$ for $PGE_2$ and each test compound was calculated using GraphPad Prism 5.

Procedure of cAMP Assay for $EP_2/EP_4$ Agonist

1. Seed cells on an $EP_2$ or $EP_4$ STEP plate at a density of 40,000-80,000 cells/well in 200 μL of reduced serum medium containing 0.5% FBE. Place the plate in a 37° C. incubator with 5% $CO_2$ and incubate overnight.

2. After 16-18 hours of incubation, aspirate the culture media from each well.

3. Add 200 μl of culture medium containing 500 μM IBMX (an inhibitor of cAMP phosphodiesterase) and different concentration of test compounds to the assigned wells. For each test compound, at least 8 concentrations starting at highest 10 μM and lowest 0.01 pM were tested. In addition each concentration had triplicates. A $PGE_2$ curve (concentrations from lowest to highest, 0 pM, 0.384 pM, 1.92 pM, 9.6 pM, 48 pM, 240 pM, 1200 pM, and 6000 pM) was always run in parallel with test compounds.

4. Incubate the cells in a cell culture incubator for 30 minutes.

5. Centrifuge the plate at 1,000× rpm for 10 minutes.

6. Aspirate the supernatant.

7. Add 100 μL of ETA assay buffer to each well and put the plate with the lid in a −80° C. freezer. Freeze the sample in the −80° C. for at least one hour.

8. Take the plate out from the −80° C. freezer and leave it at room temperature to thaw completely.

9. Centrifuge the plate at 1,000× rpm for 10 minutes.

10. Pick up 50 μl of supernatant from each well for cAMP level measurement, using an ELISA assay kit from Cayman chemical, Item #581001.

11. The data was analyzed and the $EC_{50}$ for $PGE_2$ and each test compound was calculated using GraphPad Prism 5.

Specificity of $EP_2/EP_4$ Agonist on the Receptors

Compounds demonstrating potency in SEAP or cAMP functional assays were confirmed for receptor agonist specificity by incubation of the cells with the compound together with an $EP_2$ specific antagonist AH-6809 or an $EP_4$ specific antagonist L-161,982. Compounds that showed agonist activity for either $EP_2$ or $EP_4$ are specific if the stimulation effect was diminished when incubated together with their receptor specific antagonist.

TABLE 1

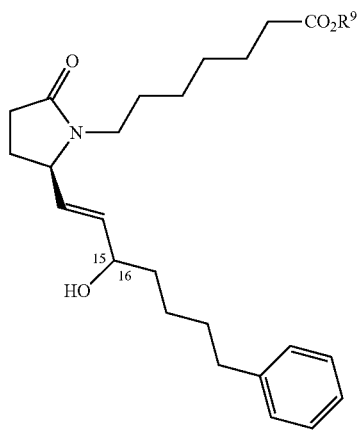

| Example No. | Absolute Configuration C-15 | $R^9$ | hEP$_4$ receptor binding | | STEP cell functional assay EC$_{50}$s (nM) | | |
|---|---|---|---|---|---|---|---|
| | | | IC$_{50}$ (nM) | K$_i$ (nM) | cAMP/EP$_4$ | SEAP/EP$_4$ | SEAP/EP$_2$ |
| 1A | α | Me | | | | | |
| 1B | β | Me | | | | | |
| 1C | α | H | 10 | 3.8 | 1.37 | 0.014 ± 0.020 (N = 2) | >1,000 |
| 1D | β | H | | | | | |

α = ⋯ or ⋯
β = ／ or ／

TABLE 2

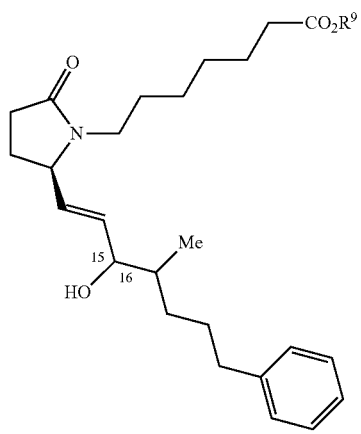

| Example No. | Absolute Configuration C-15 | Absolute Configuration C-16 | $R^9$ | hEP$_4$ receptor binding | | STEP cell functional assay EC$_{50}$s (nM) | | |
|---|---|---|---|---|---|---|---|---|
| | | | | IC$_{50}$ (nM) | K$_i$ (nM) | cAMP/EP$_4$ | SEAP/EP$_4$ | SEAP/EP$_2$ |
| 2A | α | α/β | Me | | | | | |
| 2B | β | α/β | Me | | | | | |
| 2C | α | α/β | H | 5.7 | 2.1 | 0.007 | 0.001 ± 0.001 (N = 2) | >1,000 |
| 2D | β | α/β | H | | | | | |

TABLE 2-continued

| | | | |
|---|---|---|---|
| 2E | α | β | H |
| 2F | α | α | H |

α = ⸺ or ⸺
β = ⁄ or ⁄

TABLE 3

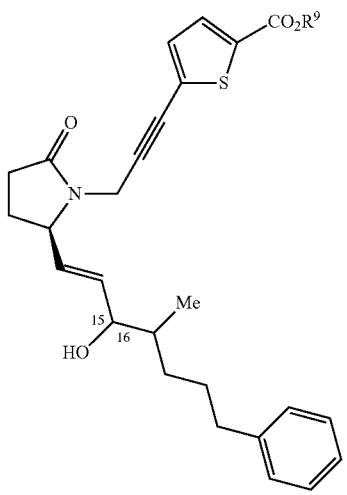

| | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^9$ | IC$_{50}$ (nM) | K$_i$ (nM) | cAMP/EP$_4$ | SEAP/EP$_4$ | SEAP/EP$_2$ |
| 3A | α | α/β | Me | | | | | |
| 3B | β | α/β | Me | | | | | |
| 3C | α | α/β | H | | | | 0.019 | >10,000 |
| 3D | β | α/β | H | | | | 31.5 | >10,000 |

α = ⸺ or ⸺
β = ⁄ or ⁄

TABLE 4

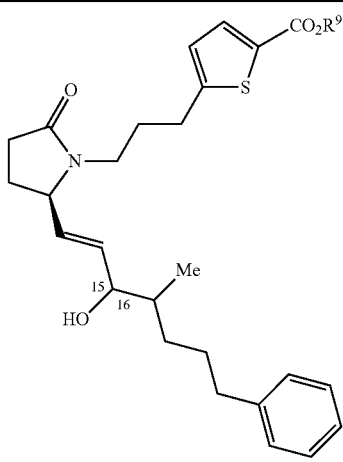

| | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^9$ | IC$_{50}$ (nM) | K$_i$ (nM) | cAMP/EP$_4$ | SEAP/EP$_4$ | SEAP/EP$_2$ |
| 4A | α | α/β | Me | | | | | |
| 4B | β | α/β | Me | | | | | |
| 4C | α | α/β | H | | | | 0.003 | 2,280 |
| 4D | β | α/β | H | | | | | >10,000 |

TABLE 4-continued

| | | | |
|---|---|---|---|
| 4E | α | β | H |
| 4F | α | α | H |

α = ⁄⁄⁄⁄ or ⁄⁄⁄⁄
β = ／ or ／

TABLE 5

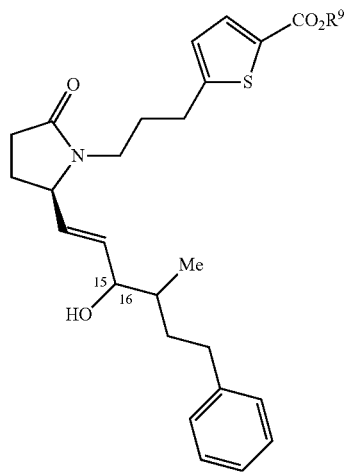

| | Absolute Configuration | | | hEP₄ receptor binding | | STEP cell functional assay EC₅₀s (nM) | | |
|---|---|---|---|---|---|---|---|---|
| Example No. | C-15 | C-16 | $R^9$ | $IC_{50}$ (nM) | $K_i$ (nM) | cAMP/EP₄ | SEAP/EP₄ | SEAP/EP₂ |
| 5A | α | β | H | | | | | |
| 5B | β | β | H | | | | | |
| 5C | α | α | H | | | | | |
| 5D | β | α | H | | | | | |

α = ⁄⁄⁄⁄ or ⁄⁄⁄⁄
β = ／ or ／

TABLE 6

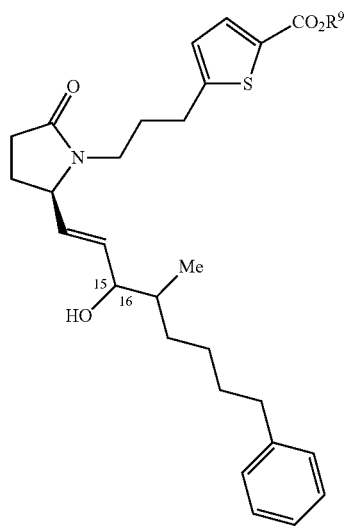

| | Absolute Configuration | | | hEP₄ receptor binding | | STEP cell functional assay EC₅₀s (nM) | | |
|---|---|---|---|---|---|---|---|---|
| Example No. | C-15 | C-16 | $R^9$ | $IC_{50}$ (nM) | $K_i$ (nM) | cAMP/EP₄ | SEAP/EP₄ | SEAP/EP₂ |
| 6A | α | β | H | | | | | |
| 6B | β | β | H | | | | | |

TABLE 6-continued

| | | | |
|---|---|---|---|
| 6C | α | α | H |
| 6D | β | α | H |

α = ⁄⁄⁄ or ⁄⁄⁄
β = ⁄ or ⁄

TABLE 7

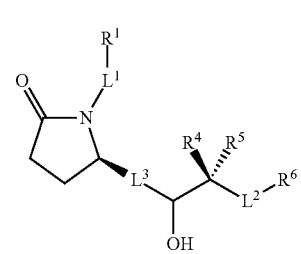

| | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^9$ | IC$_{50}$ (nM) | K$_i$ (nM) | cAMP/EP$_4$ | SEAP/EP$_4$ | SEAP/EP$_2$ |
| 7A | α | β | H | | | | | |
| 7B | β | β | H | | | | | |
| 7C | α | α | H | | | | | |
| 7D | β | α | H | | | | | |

α = ⁄⁄⁄ or ⁄⁄⁄
β = ⁄ or ⁄

We claim:

1. A compound of formula (Ia)

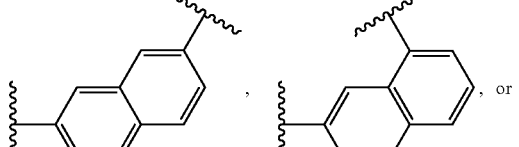

or a pharmaceutically acceptable salt thereof, wherein:

L$^1$ is
a) C$_3$-C$_7$alkylene, C$_3$-C$_7$alkenylene, or C$_3$-C$_7$alkynylene, wherein the C$_3$-C$_7$alkylene, C$_3$-C$_7$alkenylene, or C$_3$-C$_7$alkynylene is optionally substituted with 1, 2, 3, or 4 fluoro substituents;
b) —(CH$_2$)$_t$-G-(CH$_2$)$_p$—; wherein t is 0, 1, or 2, p is 0, 1, 2, or 3, and t+p=0, 1, 2, 3, or 4; or
c) —(CH$_2$)$_n$-G$^1$-(CH$_2$)$_p$—, —(CH$_2$)$_n$-G$^2$-(CH$_2$)$_p$—, —(CH$_2$)$_n$—C≡C-G$^2$-, or —(CH$_2$)$_n$—C(R$^{12}$)=C(R$^{12}$)-G$^2$-, wherein n is 1, 2, 3, 4, or 5, p is 0, 1, 2, or 3, and n+p=1, 2, 3, 4, 5, or 6;

G is

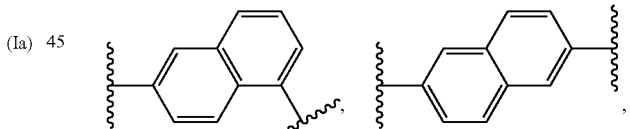

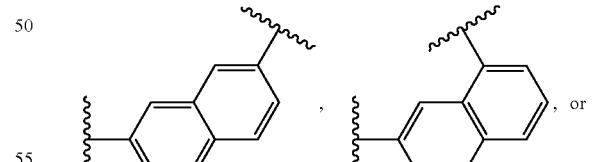

G$^1$ is O, C(O), S, S(O), S(O)$_2$, or NR$^7$; wherein R$^7$ is H, C$_1$-C$_4$ alkyl, or C$_1$-C$_4$alkylcarbonyl;

G2 is

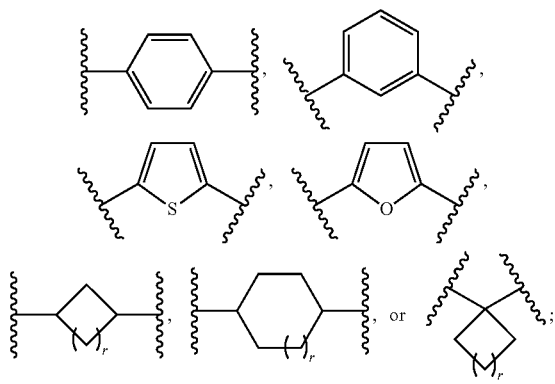

wherein G² is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^1$ is $COOR^9$, $CONR^9R^{10}$, $CH_2OR^9$, $SO_3R^9$, $SO_2NR^9R^{10}$, $PO(OR^9)_2$, or tetrazol-5-yl;

$R^9$ is H, $C_1$-$C_4$ alkyl, or aryl;

$R^{10}$ is H, $C_1$-$C_4$ alkyl, $COR^{11}$, $OR^9$, or $SO_2R^{11}$;

$R^{11}$ is $C_1$-$C_4$ alkyl;

$R^{12}$, at each occurrence, is independently H or $C_1$-$C_4$alkyl;

$L^3$ is —$C(R^2)_2$—$C(R^3)_2$—, —$C(R^2)$=$C(R^3)$—, —C≡C—, or

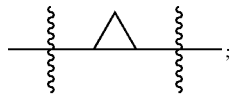

wherein $R^2$ and $R^3$ are each H, $CH_3$, fluoro, or choro;

$R^4$ and $R^5$ are each independently H or $C_1$-$C_4$ alkyl, wherein no more than one of $R^4$ and $R^5$ is H;

$L^2$ is $C_2$-$C_6$alkylene or $C_2$-$C_6$alkenylene, wherein the alkylene or alkenylene are optionally substituted with 1, 2, 3, or 4 fluoro substituents;

$R^6$ is aryl or heteroaryl, wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy; and r is 0 or 1.

2. The compound of claim 1, or a pharmaceutically acceptable salt thereof, wherein:

$L^1$ is a) $C_3$-$C_7$alkylene, wherein the alkylene is optionally substituted with 1, 2, 3, or 4 fluoro substituents; or c) —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6;

$G^2$ is

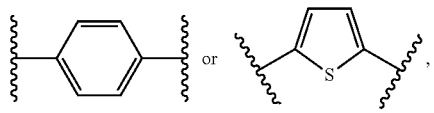

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^1$ is $COOR^9$; and $R^9$ is H or $C_1$-$C_4$ alkyl.

3. The compound of claim 1, or a pharmaceutically acceptable salt thereof, wherein:

$L^2$ is $C_2$-$C_6$alkylene, wherein the alkylene is optionally substituted with 1, 2, 3, or 4 fluoro substituents;

$L^3$ is —$C(R^2)$=$C(R^3)$—;

$R^2$ and $R^3$ are each hydrogen; and $R^6$ is aryl or heteroaryl, wherein the aryl and heteroaryl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

4. The compound of claim 2, or a pharmaceutically acceptable salt thereof, wherein:

$L^3$ is —$C(R^2)_2$—$C(R^3)_2$—, —$C(R^2)$=$C(R^3)$—, —C≡C—, or

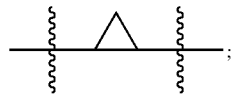

wherein $R^2$ and $R^3$ are each H, $CH_3$, fluoro, or chloro; and $R^6$ is aryl or heteroaryl, wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

5. The compound of claim 4, or a pharmaceutically acceptable salt thereof, wherein:

$L^3$ is

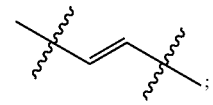 [SMILES: */C=C/*]

$L^2$ is $C_2$-$C_6$alkylene; and $R^6$ is aryl, wherein the aryl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

6. The compound of claim 5, or a pharmaceutically acceptable salt thereof, wherein:

One of $R^4$ and $R^5$ is $CH_3$ and the other is H;

$L^1$ is a) $C_3$-$C_7$alkylene; or c) —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2 or 3;

p is 0, 1, or 2, and n+p=1, 2, 3, or 4;

$G^2$ is

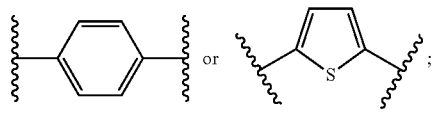

L² is ethylene, n-propylene, n-butylene, or n-pentylene; and

R⁶ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

7. The compound of claim 6, or a pharmaceutically acceptable salt thereof, wherein:

L¹ is a) n-hexylene; or c) —$(CH_2)_n$-G²-$(CH_2)_p$-, —$CH_2$—C≡C-G²-, or —$CH_2$—C(H)=C(H)-G²-, wherein n is 1, 2 or 3; p is 0 or 1, and n+p=2 or 3;

G² is

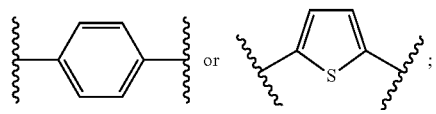 [SMILES: *c1ccc(*)cc1 ; *c1ccc(*)s1]

R¹ is COOR⁹;
R⁹ is H or CH₃;
L² is n-propylene or n-butylene; and
R⁶ is phenyl.

8. The compound of claim 5, or a pharmaceutically acceptable salt thereof, wherein L² is n-propylene.

9. The compound of claim 5, or a pharmaceutically acceptable salt thereof, wherein L² is n-butylene.

10. The compound of claim 5, or a pharmaceutically acceptable salt thereof, wherein:

L¹ is $C_3$-$C_7$alkylene, wherein the $C_3$-$C_7$alkylene is optionally substituted with 1, 2, 3, or 4 fluoro substituents.

11. The compound of claim 5, or a pharmaceutically acceptable salt thereof, wherein:

L¹ is c) —$(CH_2)_n$-G²-$(CH_2)_p$—, —$(CH_2)_n$—C≡C-G²-, or —$(CH_2)_n$—C(H)=C(H)-G²-, wherein n is 1, 2, 3, 4, or 5, p is 0, 1, 2, or 3, and n+p=1, 2, 3, 4, 5, or 6; and G² is

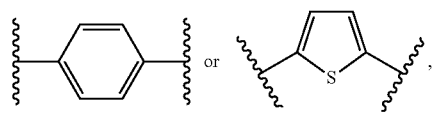

wherein G² is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

12. The compound of claim 8, or a pharmaceutically acceptable salt thereof, wherein:

L¹ is $C_3$-$C_7$alkylene, wherein the $C_3$-$C_7$alkylene is optionally substituted with 1, 2, 3, or 4 fluoro substituents.

13. The compound of claim 8, or a pharmaceutically acceptable salt thereof, wherein:

L¹ is c) —$(CH_2)_n$-G²-$(CH_2)_p$—, —$(CH_2)_n$—C≡C-G²-, or —$(CH_2)_n$—C(H)=C(H)-G²-, wherein n is 1, 2, 3, 4, or 5, p is 0, 1, 2, or 3, and n+p=1, 2, 3, 4, 5, or 6; and G² is

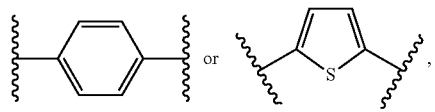

wherein G² is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

14. The compound of claim 9, or a pharmaceutically acceptable salt thereof, wherein:

L¹ is $C_3$-$C_7$alkylene, wherein the alkylene is optionally substituted with 1, 2, 3, or 4 fluoro substituents.

15. The compound of claim 9, or a pharmaceutically acceptable salt thereof, wherein:

L¹ is —$(CH_2)_n$-G²-$(CH_2)_p$—, wherein n is 2, 3, 4, or 5, p is 0, 1, 2, or 3, and n+p=2, 3, 4, 5, or 6; and G² is

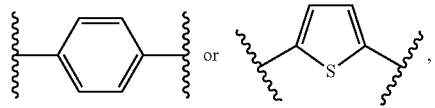

wherein G² is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy.

16. The compound of claim 5, or a pharmaceutically acceptable salt thereof, wherein:

L¹ is a) $C_3$-$C_7$alkylene; or c) —$(CH_2)_3$-G²-, —$CH_2$—C≡C-G²-, or —$CH_2$—C(H)=C(H)-G²-;

G² is

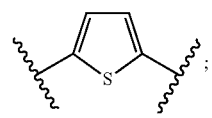 [SMILES: *c1ccc(*)s1]

L² is ethylene, n-propylene, n-butylene, or n-pentylene; and

R⁶ is phenyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

17. The compound of claim 6, or a pharmaceutically acceptable salt thereof, wherein:

L¹ is a) $C_3$-$C_7$alkylene; or c) —$(CH_2)_3$-G²-, —$CH_2$—C≡C-G²-, or —$CH_2$—C(H)=C(H)-G²-; and G2 is

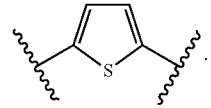 [SMILES: *c1ccc(*)s1]

18. A compound, or a pharmaceutically acceptable salt thereof, selected from the group consisting of:

methyl 7-((R)-2-((3S,4S,E)-3-hydroxy-4-methyl-6-phenylhex-1-en-1-yl)-5-oxopyrrolidin-1-yl)heptanoate;

(Z)-methyl 7-((R)-2-((3S,4S,E)-3-hydroxy-4-methyl-6-phenylhex-1-en-1-yl)-5-oxopyrrolidin-1-yl)hept-5-enoate;

methyl 4-((2-((R)-2-((3S,4S,E)-3-hydroxy-4-methyl-6-phenylhex-1-en-1-yl)-5-oxopyrrolidin-1-yl)ethyl)thio)butanoate;

methyl 5-(3-((R)-2-((3S,4S,E)-3-hydroxy-4-methyl-6-phenylhex-1-en-1-yl)-5-oxopyrrolidin-1-yl)propyl)thiophene-2-carboxylate;

methyl 5-(3-((R)-2-((3S,4S,E)-3-hydroxy-4-methyl-6-phenylhex-1-en-1-yl)-5-oxopyrrolidin-1-yl)prop-1-yn-1-yl)thiophene-2-carboxylate;

methyl 5-((Z)-3-((R)-2-((3S,4S,E)-3-hydroxy-4-methyl-6-phenylhex-1-en-1-yl)-5-oxopyrrolidin-1-yl)prop-1-en-1-yl)thiophene-2-carboxylate;

methyl 4-(2-((R)-2-((3S,4S,E)-3-hydroxy-4-methyl-6-phenylhex-1-en-1-yl)-5-oxopyrrolidin-1-yl)ethyl)benzoate;

methyl 3-(3-((R)-2-((3S,4S,E)-3-hydroxy-4-methyl-6-phenylhex-1-en-1-yl)-5-oxopyrrolidin-1-yl)propyl)benzoate;

7-((R)-2-((3S,4S,E)-3-hydroxy-4-methyl-6-phenylhex-1-en-1-yl)-5-oxopyrrolidin-1-yl)heptanoic acid;

(Z)-7-((R)-2-((3S,4S,E)-3-hydroxy-4-methyl-6-phenylhex-1-en-1-yl)-5-oxopyrrolidin-1-yl)hept-5-enoic acid;

4-((2-((R)-2-((3S,4S,E)-3-hydroxy-4-methyl-6-phenylhex-1-en-1-yl)-5-oxopyrrolidin-1-yl)ethyl)thio)butanoic acid;

5-(3-((R)-2-((3S,4S,E)-3-hydroxy-4-methyl-6-phenylhex-1-en-1-yl)-5-oxopyrrolidin-1-yl)propyl)thiophene-2-carboxylic acid;

5-(3-((R)-2-((3S,4S,E)-3-hydroxy-4-methyl-6-phenylhex-1-en-1-yl)-5-oxopyrrolidin-1-yl)prop-1-yn-1-yl)thiophene-2-carboxylic acid;

5-((Z)-3-((R)-2-((3S,4S,E)-3-hydroxy-4-methyl-6-phenylhex-1-en-1-yl)-5-oxopyrrolidin-1-yl)prop-1-en-1-yl)thiophene-2-carboxylic acid;

4-(2-((R)-2-((3S,4S,E)-3-hydroxy-4-methyl-6-phenylhex-1-en-1-yl)-5-oxopyrrolidin-1-yl)ethyl)benzoic acid;

3-(3-((R)-2-((3S,4S,E)-3-hydroxy-4-methyl-6-phenylhex-1-en-1-yl)-5-oxopyrrolidin-1-yl)propyl)benzoic acid;

methyl 7-((S)-2-((3R,4S)-3-hydroxy-4-methyl-6-phenylhexyl)-5-oxopyrrolidin-1-yl)heptanoate;

(Z)-methyl 7-((S)-2-((3R,4S)-3-hydroxy-4-methyl-6-phenylhexyl)-5-oxopyrrolidin-1-yl)hept-5-enoate;

methyl 4-((2-((S)-2-((3R,4S)-3-hydroxy-4-methyl-6-phenylhexyl)-5-oxopyrrolidin-1-yl)ethyl)thio)butanoate;

methyl 5-(3-((S)-2-((3R,4S)-3-hydroxy-4-methyl-6-phenylhexyl)-5-oxopyrrolidin-1-yl)propyl)thiophene-2-carboxylate;

methyl 5-(3-((S)-2-((3R,4S)-3-hydroxy-4-methyl-6-phenylhexyl)-5-oxopyrrolidin-1-yl)prop-1-yn-1-yl)thiophene-2-carboxylate;

methyl 5-((Z)-3-((S)-2-((3R,4S)-3-hydroxy-4-methyl-6-phenylhexyl)-5-oxopyrrolidin-1-yl)prop-1-en-1-yl)thiophene-2-carboxylate;

methyl 4-(2-((S)-2-((3R,4S)-3-hydroxy-4-methyl-6-phenylhexyl)-5-oxopyrrolidin-1-yl)ethyl)benzoate;

methyl 3-(3-((S)-2-((3R,4S)-3-hydroxy-4-methyl-6-phenylhexyl)-5-oxopyrrolidin-1-yl)propyl)benzoate;

7-((S)-2-((3R,4S)-3-hydroxy-4-methyl-6-phenylhexyl)-5-oxopyrrolidin-1-yl)heptanoic acid;

(Z)-7-((S)-2-((3R,4S)-3-hydroxy-4-methyl-6-phenylhexyl)-5-oxopyrrolidin-1-yl)hept-5-enoic acid;

4-((2-((S)-2-((3R,4S)-3-hydroxy-4-methyl-6-phenylhexyl)-5-oxopyrrolidin-1-yl)ethyl)thio)butanoic acid;

5-(3-((S)-2-((3R,4S)-3-hydroxy-4-methyl-6-phenylhexyl)-5-oxopyrrolidin-1-yl)propyl)thiophene-2-carboxylic acid;

5-(3-((S)-2-((3R,4S)-3-hydroxy-4-methyl-6-phenylhexyl)-5-oxopyrrolidin-1-yl)prop-1-yn-1-yl)thiophene-2-carboxylic acid;

5-((Z)-3-((S)-2-((3R,4S)-3-hydroxy-4-methyl-6-phenylhexyl)-5-oxopyrrolidin-1-yl)prop-1-en-1-yl)thiophene-2-carboxylic acid;

4-(2-((S)-2-((3R,4S)-3-hydroxy-4-methyl-6-phenylhexyl)-5-oxopyrrolidin-1-yl)ethyl)benzoic acid;

3-(3-((S)-2-((3R,4S)-3-hydroxy-4-methyl-6-phenylhexyl)-5-oxopyrrolidin-1-yl)propyl)benzoic acid;

methyl 7-((R)-2-((3S,4S,E)-3-hydroxy-4-methyl-7-phenylhept-1-en-1-yl)-5-oxopyrrolidin-1-yl)heptanoate;

methyl 7-((R)-2-((3S,4R,E)-3-hydroxy-4-methyl-7-phenylhept-1-en-1-yl)-5-oxopyrrolidin-1-yl)heptanoate;

(Z)-methyl 7-((R)-2-((3S,4S,E)-3-hydroxy-4-methyl-7-phenylhept-1-en-1-yl)-5-oxopyrrolidin-1-yl)hept-5-enoate;

methyl 4-((2-((R)-2-((3S,4S,E)-3-hydroxy-4-methyl-7-phenylhept-1-en-1-yl)-5-oxopyrrolidin-1-yl)ethyl)thio)butanoate;

methyl 5-(3-((R)-2-((3S,4S,E)-3-hydroxy-4-methyl-7-phenylhept-1-en-1-yl)-5-oxopyrrolidin-1-yl)propyl)thiophene-2-carboxylate;

methyl 5-(3-((R)-2-((3S,4S,E)-3-hydroxy-4-methyl-7-phenylhept-1-en-1-yl)-5-oxopyrrolidin-1-yl)prop-1-yn-1-yl)thiophene-2-carboxylate;

methyl 5-((Z)-3-((R)-2-((3S,4S,E)-3-hydroxy-4-methyl-7-phenylhept-1-en-1-yl)-5-oxopyrrolidin-1-yl)prop-1-en-1-yl)thiophene-2-carboxylate;

methyl 4-(2-((R)-2-((3S,4S,E)-3-hydroxy-4-methyl-7-phenylhept-1-en-1-yl)-5-oxopyrrolidin-1-yl)ethyl)benzoate;

methyl 3-(3-((R)-2-((3S,4S,E)-3-hydroxy-4-methyl-7-phenylhept-1-en-1-yl)-5-oxopyrrolidin-1-yl)propyl)benzoate;

7-((R)-2-((3S,4S,E)-3-hydroxy-4-methyl-7-phenylhept-1-en-1-yl)-5-oxopyrrolidin-1-yl)heptanoic acid;

7-((R)-2-((3S,4R,E)-3-hydroxy-4-methyl-7-phenylhept-1-en-1-yl)-5-oxopyrrolidin-1-yl)heptanoic acid;

(Z)-7-((R)-2-((3S,4S,E)-3-hydroxy-4-methyl-7-phenylhept-1-en-1-yl)-5-oxopyrrolidin-1-yl)hept-5-enoic acid;

4-((2-((R)-2-((3S,4S,E)-3-hydroxy-4-methyl-7-phenylhept-1-en-1-yl)-5-oxopyrrolidin-1-yl)ethyl)thio)butanoic acid;

5-(3-((R)-2-((3S,4S,E)-3-hydroxy-4-methyl-7-phenylhept-1-en-1-yl)-5-oxopyrrolidin-1-yl)propyl)thiophene-2-carboxylic acid;

5-(3-((R)-2-((3S,4S,E)-3-hydroxy-4-methyl-7-phenylhept-1-en-1-yl)-5-oxopyrrolidin-1-yl)prop-1-yn-1-yl)thiophene-2-carboxylic acid;

5-((Z)-3-((R)-2-((3S,4S,E)-3-hydroxy-4-methyl-7-phenylhept-1-en-1-yl)-5-oxopyrrolidin-1-yl)prop-1-en-1-yl)thiophene-2-carboxylic acid;

4-(2-((R)-2-((3S,4S,E)-3-hydroxy-4-methyl-7-phenylhept-1-en-1-yl)-5-oxopyrrolidin-1-yl)ethyl)benzoic acid;

3-(3-((R)-2-((3S,4S,E)-3-hydroxy-4-methyl-7-phenyl-hept-1-en-1-yl)-5-oxopyrrolidin-1-yl)propyl)benzoic acid;
methyl 7-((S)-2-((3R,4S)-3-hydroxy-4-methyl-7-phenyl-heptyl)-5-oxopyrrolidin-1-yl)heptanoate;
methyl 7-((S)-2-((3R,4R)-3-hydroxy-4-methyl-7-phenyl-heptyl)-5-oxopyrrolidin-1-yl)heptanoate;
(Z)-methyl 7-((S)-2-((3R,4S)-3-hydroxy-4-methyl-7-phenylheptyl)-5-oxopyrrolidin-1-yl)hept-5-enoate;
methyl 4-((2-((S)-2-((3R,4S)-3-hydroxy-4-methyl-7-phenylheptyl)-5-oxopyrrolidin-1-yl)ethyl)thio)butanoate;
methyl 5-(3-((S)-2-((3R,4S)-3-hydroxy-4-methyl-7-phenylheptyl)-5-oxopyrrolidin-1-yl)propyl)thiophene-2-carboxylate;
methyl 5-(3-((S)-2-((3R,4S)-3-hydroxy-4-methyl-7-phenylheptyl)-5-oxopyrrolidin-1-yl)prop-1-yn-1-yl)thiophene-2-carboxylate;
methyl 5-((Z)-3-((S)-2-((3R,4S)-3-hydroxy-4-methyl-7-phenylheptyl)-5-oxopyrrolidin-1-yl)prop-1-en-1-yl)thiophene-2-carboxylate;
methyl 4-(2-((S)-2-((3R,4S)-3-hydroxy-4-methyl-7-phenylheptyl)-5-oxopyrrolidin-1-yl)ethyl)benzoate;
methyl 3-(3-((S)-2-((3R,4S)-3-hydroxy-4-methyl-7-phenylheptyl)-5-oxopyrrolidin-1-yl)propyl)benzoate;
7-((S)-2-((3R,4S)-3-hydroxy-4-methyl-7-phenylheptyl)-5-oxopyrrolidin-1-yl)heptanoic acid;
7-((S)-2-((3R,4R)-3-hydroxy-4-methyl-7-phenylheptyl)-5-oxopyrrolidin-1-yl)heptanoic acid;
(Z)-7-((S)-2-((3R,4S)-3-hydroxy-4-methyl-7-phenylheptyl)-5-oxopyrrolidin-1-yl)hept-5-enoic acid;
4-((2-((S)-2-((3R,4S)-3-hydroxy-4-methyl-7-phenylheptyl)-5-oxopyrrolidin-1-yl)ethyl)thio)butanoic acid;
5-(3-((S)-2-((3R,4S)-3-hydroxy-4-methyl-7-phenylheptyl)-5-oxopyrrolidin-1-yl)propyl)thiophene-2-carboxylic acid;
5-(3-((S)-2-((3R,4S)-3-hydroxy-4-methyl-7-phenylheptyl)-5-oxopyrrolidin-1-yl)prop-1-yn-1-yl)thiophene-2-carboxylic acid;
5-((Z)-3-((S)-2-((3R,4S)-3-hydroxy-4-methyl-7-phenylheptyl)-5-oxopyrrolidin-1-yl)prop-1-en-1-yl)thiophene-2-carboxylic acid;
4-(2-((S)-2-((3R,4S)-3-hydroxy-4-methyl-7-phenylheptyl)-5-oxopyrrolidin-1-yl)ethyl)benzoic acid;
3-(3-((S)-2-((3R,4S)-3-hydroxy-4-methyl-7-phenylheptyl)-5-oxopyrrolidin-1-yl)propyl)benzoic acid;
methyl 7-((R)-2-((3S,4S,E)-3-hydroxy-4-methyl-8-phenyloct-1-en-1-yl)-5-oxopyrrolidin-1-yl)heptanoate;
(Z)-methyl 7-((R)-2-((3S,4S,E)-3-hydroxy-4-methyl-8-phenyloct-1-en-1-yl)-5-oxopyrrolidin-1-yl)hept-5-enoate;
methyl 4-((2-((R)-2-((3S,4S,E)-3-hydroxy-4-methyl-8-phenyloct-1-en-1-yl)-5-oxopyrrolidin-1-yl)ethyl)thio)butanoate;
methyl 5-(3-((R)-2-((3S,4S,E)-3-hydroxy-4-methyl-8-phenyloct-1-en-1-yl)-5-oxopyrrolidin-1-yl)propyl)thiophene-2-carboxylate;
methyl 5-(3-((R)-2-((3S,4S,E)-3-hydroxy-4-methyl-8-phenyloct-1-en-1-yl)-5-oxopyrrolidin-1-yl)prop-1-yn-1-yl)thiophene-2-carboxylate;
methyl 5-((Z)-3-((R)-2-((3S,4S,E)-3-hydroxy-4-methyl-8-phenyloct-1-en-1-yl)-5-oxopyrrolidin-1-yl)prop-1-en-1-yl)thiophene-2-carboxylate;
methyl 4-(2-((R)-2-((3S,4S,E)-3-hydroxy-4-methyl-8-phenyloct-1-en-1-yl)-5-oxopyrrolidin-1-yl)ethyl)benzoate;
methyl 3-(3-((R)-2-((3S,4S,E)-3-hydroxy-4-methyl-8-phenyloct-1-en-1-yl)-5-oxopyrrolidin-1-yl)propyl)benzoate;
7-((R)-2-((3S,4S,E)-3-hydroxy-4-methyl-8-phenyloct-1-en-1-yl)-5-oxopyrrolidin-1-yl)heptanoic acid;
(Z)-7-((R)-2-((3S,4S,E)-3-hydroxy-4-methyl-8-phenyloct-1-en-1-yl)-5-oxopyrrolidin-1-yl)hept-5-enoic acid;
4-((2-((R)-2-((3S,4S,E)-3-hydroxy-4-methyl-8-phenyloct-1-en-1-yl)-5-oxopyrrolidin-1-yl)ethyl)thio)butanoic acid;
5-(3-((R)-2-((3S,4S,E)-3-hydroxy-4-methyl-8-phenyloct-1-en-1-yl)-5-oxopyrrolidin-1-yl)propyl)thiophene-2-carboxylic acid;
5-(3-((R)-2-((3S,4S,E)-3-hydroxy-4-methyl-8-phenyloct-1-en-1-yl)-5-oxopyrrolidin-1-yl)prop-1-yn-1-yl)thiophene-2-carboxylic acid;
5-((Z)-3-((R)-2-((3S,4S,E)-3-hydroxy-4-methyl-8-phenyloct-1-en-1-yl)-5-oxopyrrolidin-1-yl)prop-1-en-1-yl)thiophene-2-carboxylic acid;
4-(2-((R)-2-((3S,4S,E)-3-hydroxy-4-methyl-8-phenyloct-1-en-1-yl)-5-oxopyrrolidin-1-yl)ethyl)benzoic acid;
3-(3-((R)-2-((3S,4S,E)-3-hydroxy-4-methyl-8-phenyloct-1-en-1-yl)-5-oxopyrrolidin-1-yl)propyl)benzoic acid;
methyl 7-((S)-2-((3R,4S)-3-hydroxy-4-methyl-8-phenyloctyl)-5-oxopyrrolidin-1-yl)heptanoate;
(Z)-methyl 7-((S)-2-((3R,4S)-3-hydroxy-4-methyl-8-phenyloctyl)-5-oxopyrrolidin-1-yl)hept-5-enoate;
methyl 4-((2-((S)-2-((3R,4S)-3-hydroxy-4-methyl-8-phenyloctyl)-5-oxopyrrolidin-1-yl)ethyl)thio)butanoate;
methyl 5-(3-((S)-2-((3R,4S)-3-hydroxy-4-methyl-8-phenyloctyl)-5-oxopyrrolidin-1-yl)propyl)thiophene-2-carboxylate;
methyl 5-(3-((S)-2-((3R,4S)-3-hydroxy-4-methyl-8-phenyl octyl)-5-oxopyrrolidin-1-yl)prop-1-yn-1-yl)thiophene-2-carboxylate;
methyl 5-((Z)-3-((S)-2-((3R,4S)-3-hydroxy-4-methyl-8-phenyloctyl)-5-oxopyrrolidin-1-yl)prop-1-en-1-yl)thiophene-2-carboxylate;
methyl 4-(2-((S)-2-((3R,4S)-3-hydroxy-4-methyl-8-phenyloctyl)-5-oxopyrrolidin-1-yl)ethyl)benzoate;
methyl 3-(3-((S)-2-((3R,4S)-3-hydroxy-4-methyl-8-phenyloctyl)-5-oxopyrrolidin-1-yl)propyl)benzoate;
7-((S)-2-((3R,4S)-3-hydroxy-4-methyl-8-phenyloctyl)-5-oxopyrrolidin-1-yl)heptanoic acid;
(Z)-7-((S)-2-((3R,4S)-3-hydroxy-4-methyl-8-phenyl octyl)-5-oxopyrrolidin-1-yl)hept-5-enoic acid;
4-((2-((S)-2-((3R,4S)-3-hydroxy-4-methyl-8-phenyloctyl)-5-oxopyrrolidin-1-yl)ethyl)thio)butanoic acid;
5-(3-((S)-2-((3R,4S)-3-hydroxy-4-methyl-8-phenyloctyl)-5-oxopyrrolidin-1-yl)propyl)thiophene-2-carboxylic acid;
5-(3-((S)-2-((3R,4S)-3-hydroxy-4-methyl-8-phenyloctyl)-5-oxopyrrolidin-1-yl)prop-1-yn-1-yl)thiophene-2-carboxylic acid;
5-((Z)-3-((S)-2-((3R,4S)-3-hydroxy-4-methyl-8-phenyl octyl)-5-oxopyrrolidin-1-yl)prop-1-en-1-yl)thiophene-2-carboxylic acid;
4-(2-((S)-2-((3R,4S)-3-hydroxy-4-methyl-8-phenyloctyl)-5-oxopyrrolidin-1-yl)ethyl)benzoic acid;
3-(3-((S)-2-((3R,4S)-3-hydroxy-4-methyl-8-phenyloctyl)-5-oxopyrrolidin-1-yl)propyl)benzoic acid;
methyl 7-((R)-2-((3S,4S,E)-3-hydroxy-4-methyl-7-phenylhept-1-en-1-yl)-5-oxopyrrolidin-1-yl)hept-5-ynoate; and
7-((R)-2-((3S,4S,E)-3-hydroxy-4-methyl-7-phenylhept-1-en-1-yl)-5-oxopyrrolidin-1-yl)hept-5-ynoic acid.

19. A pharmaceutical composition comprising the compound of claim 1, or pharmaceutically acceptable salts thereof, and a pharmaceutically acceptable carrier.

20. A method of treating glaucoma, osteoporosis, bone fracture, or bone loss due to periodontal disease, comprising administering a therapeutically effective amount of the compound of claim 1 to a patient in need thereof.

21. A method of stimulating bone formation in a tooth socket having undergone implantation, a joint that is to undergo or that has undergone orthopedic implantation, or vertebrae that have undergone spinal fusion comprising administering a therapeutically effective amount of the compound of claim 1 to a patient in need thereof.

22. A method of treating glaucoma, alopecia, or neuropathic pain comprising administering a therapeutically effective amount of the compound of claim 1 to a patient in need thereof.

23. The compound of claim 18 selected from:
7-((R)-2-((3S,4S,E)-3-hydroxy-4-methyl-7-phenylhept-1-en-1-yl)-5-oxopyrrolidin-1-yl)heptanoic acid, or a pharmaceutically acceptable salt thereof.

24. The compound of claim 18 selected from:
5-(3-((R)-2-((3S,4S,E)-3-hydroxy-4-methyl-7-phenyl-hept-1-en-1-yl)-5-oxopyrrolidin-1-yl)propyl)thiophene-2-carboxylic acid, or a pharmaceutically acceptable salt thereof.

* * * * *